United States Patent
Conlon et al.

(10) Patent No.: US 10,154,852 B2
(45) Date of Patent: Dec. 18, 2018

(54) ULTRASONIC SURGICAL BLADE WITH IMPROVED CUTTING AND COAGULATION FEATURES

(71) Applicant: Ethicon Endo-Surgery, LLC, Guaynabo, PR (US)

(72) Inventors: Sean P. Conlon, Loveland, OH (US); Jacob S. Gee, Cincinnati, OH (US); Foster B. Stulen, Mason, OH (US); William D. Dannaher, Cincinnati, OH (US); William A. Olson, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 341 days.

(21) Appl. No.: 14/789,744

(22) Filed: Jul. 1, 2015

(65) Prior Publication Data
US 2017/0000513 A1    Jan. 5, 2017

(51) Int. Cl.
*A61B 17/32* (2006.01)
*A61B 17/00* (2006.01)

(52) U.S. Cl.
CPC ............. *A61B 17/320068* (2013.01); *A61B 2017/00424* (2013.01); *A61B 2017/320072* (2013.01); *A61B 2017/320075* (2017.08); *A61B 2017/320078* (2017.08)

(58) Field of Classification Search
CPC ........... A61B 17/320068; A61B 2017/320072; A61B 2018/1422
USPC ...................................................... 606/169
See application file for complete search history.

(56) References Cited

U.S. PATENT DOCUMENTS

| | | | |
|---|---|---|---|
| 969,528 | A | 9/1910 | Disbrow |
| 1,570,025 | A | 1/1926 | Young |
| 1,813,902 | A | 7/1931 | Bovie |
| 2,188,497 | A | 1/1940 | Calva |
| 2,366,274 | A | 1/1945 | Luth et al. |
| 2,425,245 | A | 8/1947 | Johnson |
| 2,442,966 | A | 6/1948 | Wallace |
| 2,458,152 | A | 1/1949 | Eakins |
| 2,510,693 | A | 6/1950 | Green |

(Continued)

FOREIGN PATENT DOCUMENTS

| | | |
|---|---|---|
| AU | 2003241752 A1 | 9/2003 |
| CA | 2535467 A1 | 4/1993 |

(Continued)

OTHER PUBLICATIONS

Written Opinion of the International Searching Authority for PCT/US2016/040377, dated Jan. 9, 2017.*

(Continued)

*Primary Examiner* — Katherine M Shi

(57) ABSTRACT

An ultrasonic surgical blade with improved cutting and coagulation features is disclosed. The blade includes a solid body, a longitudinal portion having a proximal end configured to couple to an ultrasonic transmission waveguide and a transverse portion extending crosswise from the distal end of the longitudinal portion. At least one dissection edge and at least one hemostasis surface is provided on the blade. The transverse portion defines a hook having a free end configured to pull and dissect tissue. Also disclosed is an ultrasonic surgical blade that also includes a sharp central ridge and an end mass for acoustic balance.

14 Claims, 48 Drawing Sheets

(56) References Cited

U.S. PATENT DOCUMENTS

| | | |
|---|---|---|
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,707 A | 8/1991 | Taheri |
| 5,061,269 A | 10/1991 | Muller |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |

(56) References Cited

U.S. PATENT DOCUMENTS

| | | |
|---|---|---|
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,443,463 A | 8/1995 | Stern et al. |
| 5,445,638 A | 8/1995 | Rydell et al. |
| 5,445,639 A | 8/1995 | Kuslich et al. |
| 5,449,370 A | 9/1995 | Vaitekunas |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |

(56) References Cited

U.S. PATENT DOCUMENTS

| | | |
|---|---|---|
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,155 A | 7/1998 | Beaupre et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,959 A | 8/1998 | Castro et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |

(56) References Cited

U.S. PATENT DOCUMENTS

| | | |
|---|---|---|
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,142 B1 | 10/2002 | Faller et al. |
| 6,464,689 B1 | 10/2002 | Qin et al. |
| 6,464,702 B2 | 10/2002 | Schulze et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |

(56) References Cited

U.S. PATENT DOCUMENTS

| | | |
|---|---|---|
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Muller et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| D511,145 S | 11/2005 | Donofrio et al. |
| 6,974,450 B2 | 12/2005 | Weber et al. |

(56) References Cited

U.S. PATENT DOCUMENTS

| | | |
|---|---|---|
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |

(56) References Cited

U.S. PATENT DOCUMENTS

| | | |
|---|---|---|
| D578,645 S | 10/2008 | Shumer et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,455,208 B2 | 11/2008 | Wales et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |

(56) References Cited

U.S. PATENT DOCUMENTS

| | | | |
|---|---|---|---|
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,871,392 B2 | 1/2011 | Sartor |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |
| 8,105,323 B2 | 1/2012 | Buysse et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,415 B2 | 7/2012 | Francischelli |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |

(56) References Cited

U.S. PATENT DOCUMENTS

| | | |
|---|---|---|
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,880 B2 | 1/2013 | Messerly et al. |
| 8,348,967 B2 | 1/2013 | Stulen |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,640,788 B2 | 2/2014 | Dachs, II et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |

(56) References Cited

U.S. PATENT DOCUMENTS

| | | |
|---|---|---|
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,023,071 B2 | 5/2015 | Miller et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,179,912 B2 | 11/2015 | Yates et al. |
| 9,186,204 B2 | 11/2015 | Nishimura et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |

(56) References Cited

U.S. PATENT DOCUMENTS

| | | |
|---|---|---|
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban et al. |
| 9,265,926 B2 | 2/2016 | Strobl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,232 B2 | 6/2016 | Hunt et al. |
| 9,375,267 B2 | 6/2016 | Kerr et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,486,236 B2 | 11/2016 | Price et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,907,563 B2 | 3/2018 | Germain et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2003/0014053 A1 | 1/2003 | Nguyen et al. |

(56) References Cited

U.S. PATENT DOCUMENTS

| | | |
|---|---|---|
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1* | 11/2006 | Yoshimine ....... A61B 17/32006 601/2 |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |

(56) References Cited

U.S. PATENT DOCUMENTS

| | | |
|---|---|---|
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143799 A1 | 6/2009 | Smith et al. |
| 2009/0143800 A1 | 6/2009 | Deville et al. |
| 2009/0143806 A1 | 6/2009 | Witt et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0036370 A1 | 2/2010 | Mirel et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1* | 4/2010 | Yoshimine ....... A61B 17/32006 606/169 |
| 2010/0158307 A1 | 6/2010 | Kubota et al. |
| 2010/0168741 A1 | 7/2010 | Sanai et al. |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0274278 A1 | 10/2010 | Fleenor et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0087220 A1 | 4/2011 | Felder et al. |
| 2011/0125151 A1 | 5/2011 | Strauss et al. |
| 2011/0276049 A1 | 11/2011 | Gerhardt |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0059289 A1 | 3/2012 | Nield et al. |
| 2012/0071863 A1 | 3/2012 | Lee et al. |
| 2012/0078139 A1 | 3/2012 | Aldridge et al. |
| 2012/0078244 A1 | 3/2012 | Worrell et al. |
| 2012/0101495 A1 | 4/2012 | Young et al. |
| 2012/0109186 A1 | 5/2012 | Parrott et al. |
| 2012/0116265 A1 | 5/2012 | Houser et al. |
| 2012/0143211 A1 | 6/2012 | Kishi |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0103065 A1 | 4/2013 | Timm et al. |
| 2013/0116717 A1* | 5/2013 | Balek ............... A61B 17/32006 606/169 |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0217967 A1 | 8/2013 | Mohr et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005656 A1 | 1/2014 | Mucilli et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0114327 A1 | 4/2014 | Boudreaux et al. |
| 2014/0121569 A1 | 5/2014 | Schafer et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0257284 A1 | 9/2014 | Artale |
| 2014/0276970 A1 | 9/2014 | Messerly et al. |
| 2014/0330271 A1 | 11/2014 | Dietz et al. |
| 2014/0371735 A1 | 12/2014 | Long |
| 2015/0080876 A1 | 3/2015 | Worrell et al. |
| 2015/0088178 A1 | 3/2015 | Stulen et al. |
| 2015/0112335 A1 | 4/2015 | Boudreaux et al. |
| 2015/0148830 A1 | 5/2015 | Stulen et al. |
| 2015/0148832 A1 | 5/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182276 A1 | 7/2015 | Wiener et al. |
| 2015/0182277 A1 | 7/2015 | Wiener et al. |
| 2015/0230853 A1 | 8/2015 | Johnson et al. |
| 2015/0230861 A1 | 8/2015 | Woloszko et al. |
| 2015/0250495 A1 | 9/2015 | Robertson et al. |
| 2015/0257780 A1 | 9/2015 | Houser |
| 2015/0272602 A1 | 10/2015 | Boudreaux et al. |
| 2015/0272659 A1 | 10/2015 | Boudreaux et al. |
| 2015/0272660 A1 | 10/2015 | Boudreaux et al. |
| 2015/0327883 A1 | 11/2015 | Messerly et al. |
| 2015/0328484 A1 | 11/2015 | Messerly et al. |
| 2015/0340586 A1 | 11/2015 | Wiener et al. |
| 2015/0351792 A1 | 12/2015 | Houser et al. |
| 2016/0030076 A1 | 2/2016 | Faller et al. |
| 2016/0045248 A1 | 2/2016 | Unger et al. |
| 2016/0051316 A1 | 2/2016 | Boudreaux |

(56) References Cited

U.S. PATENT DOCUMENTS

| | | |
|---|---|---|
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0144204 A1 | 5/2016 | Akagane |
| 2016/0157927 A1 | 6/2016 | Corbett et al. |
| 2016/0175024 A1 | 6/2016 | Yates et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0206342 A1 | 7/2016 | Robertson et al. |
| 2016/0213395 A1 | 7/2016 | Anim |
| 2016/0228171 A1 | 8/2016 | Boudreaux |
| 2016/0262786 A1 | 9/2016 | Madan et al. |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296249 A1 | 10/2016 | Robertson |
| 2016/0296250 A1 | 10/2016 | Olson et al. |
| 2016/0296251 A1 | 10/2016 | Olson et al. |
| 2016/0296252 A1 | 10/2016 | Olson et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317217 A1 | 11/2016 | Batross et al. |
| 2016/0338726 A1 | 11/2016 | Stulen et al. |
| 2016/0346001 A1 | 12/2016 | Vakharia et al. |
| 2016/0361084 A1 | 12/2016 | Weisenburgh, II et al. |
| 2016/0367273 A1 | 12/2016 | Robertson et al. |
| 2016/0367281 A1 | 12/2016 | Gee et al. |
| 2016/0374708 A1 | 12/2016 | Wiener et al. |
| 2016/0374709 A1 | 12/2016 | Timm et al. |
| 2016/0374712 A1 | 12/2016 | Stulen et al. |
| 2017/0000512 A1 | 1/2017 | Conlon et al. |
| 2017/0000541 A1 | 1/2017 | Yates et al. |
| 2017/0000552 A1 | 1/2017 | Asher et al. |
| 2017/0056056 A1 | 3/2017 | Wiener et al. |
| 2017/0056058 A1 | 3/2017 | Voegele et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0090507 A1 | 3/2017 | Wiener et al. |
| 2017/0095267 A1 | 4/2017 | Messerly et al. |
| 2017/0105757 A1 | 4/2017 | Weir et al. |
| 2017/0105786 A1 | 4/2017 | Scheib et al. |
| 2017/0105791 A1 | 4/2017 | Yates et al. |
| 2017/0143371 A1 | 5/2017 | Witt et al. |
| 2017/0143877 A1 | 5/2017 | Witt et al. |
| 2017/0164972 A1 | 6/2017 | Johnson et al. |
| 2017/0172700 A1 | 6/2017 | Denzinger et al. |
| 2017/0189095 A1 | 7/2017 | Danziger et al. |
| 2017/0189096 A1 | 7/2017 | Danziger et al. |
| 2017/0189101 A1 | 7/2017 | Yates et al. |
| 2017/0196586 A1 | 7/2017 | Witt et al. |
| 2017/0196587 A1 | 7/2017 | Witt et al. |
| 2017/0202570 A1 | 7/2017 | Shelton, IV et al. |
| 2017/0202571 A1 | 7/2017 | Shelton, IV et al. |
| 2017/0202572 A1 | 7/2017 | Shelton, IV et al. |
| 2017/0202573 A1 | 7/2017 | Witt et al. |
| 2017/0202591 A1 | 7/2017 | Shelton, IV et al. |
| 2017/0202592 A1 | 7/2017 | Shelton, IV et al. |
| 2017/0202593 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2018/0014845 A1 | 1/2018 | Dannaher |
| 2018/0014846 A1 | 1/2018 | Rhee et al. |
| 2018/0014848 A1 | 1/2018 | Messerly et al. |
| 2018/0042634 A1 | 2/2018 | Conlon et al. |
| 2018/0049767 A1 | 2/2018 | Gee et al. |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0056095 A1 | 3/2018 | Messerly et al. |
| 2018/0078268 A1 | 3/2018 | Messerly et al. |
| 2018/0092660 A1 | 4/2018 | Houser et al. |
| 2018/0146975 A1 | 5/2018 | Zhang |

FOREIGN PATENT DOCUMENTS

| | | |
|---|---|---|
| CN | 1233944 A | 11/1999 |
| CN | 1253485 A | 5/2000 |
| CN | 2460047 Y | 11/2001 |
| CN | 1634601 A | 7/2005 |
| CN | 1640365 A | 7/2005 |
| CN | 1694649 A | 11/2005 |
| CN | 1775323 A | 5/2006 |
| CN | 1922563 A | 2/2007 |
| CN | 2868227 Y | 2/2007 |
| CN | 1951333 A | 4/2007 |
| CN | 101035482 A | 9/2007 |
| CN | 101040799 A | 9/2007 |
| CN | 101396300 A | 4/2009 |
| CN | 101467917 A | 7/2009 |
| CN | 101674782 A | 3/2010 |
| CN | 101883531 A | 11/2010 |
| CN | 102160045 A | 8/2011 |
| CN | 202027624 U | 11/2011 |
| CN | 102834069 A | 12/2012 |
| CN | 101313865 B | 1/2013 |
| DE | 3904558 A1 | 8/1990 |
| DE | 4300307 A1 | 7/1994 |
| DE | 4323585 A1 | 1/1995 |
| DE | 19608716 C1 | 4/1997 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0342448 A1 | 11/1989 |
| EP | 0443256 A1 | 8/1991 |
| EP | 0456470 A1 | 11/1991 |
| EP | 0238667 B1 | 2/1993 |
| EP | 0340803 B1 | 8/1993 |
| EP | 0598976 A2 | 6/1994 |
| EP | 0630612 A1 | 12/1994 |
| EP | 0424685 B1 | 5/1995 |
| EP | 0677275 A2 | 10/1995 |
| EP | 0482195 B1 | 1/1996 |
| EP | 0695535 A1 | 2/1996 |
| EP | 0705571 A1 | 4/1996 |
| EP | 0741996 B1 | 11/1996 |
| EP | 0612570 B1 | 6/1997 |
| EP | 0557806 B1 | 5/1998 |
| EP | 0640317 B1 | 9/1999 |
| EP | 1108394 A2 | 6/2001 |
| EP | 1138264 A1 | 10/2001 |
| EP | 0908148 B1 | 1/2002 |

(56) References Cited

FOREIGN PATENT DOCUMENTS

| | | |
|---|---|---|
| EP | 1229515 A2 | 8/2002 |
| EP | 0722696 B1 | 12/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1293172 B1 | 4/2006 |
| EP | 0875209 B1 | 5/2006 |
| EP | 1433425 B1 | 6/2006 |
| EP | 1256323 B1 | 8/2006 |
| EP | 1698289 A2 | 9/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1815950 A1 | 8/2007 |
| EP | 1839599 A1 | 10/2007 |
| EP | 1844720 A1 | 10/2007 |
| EP | 1862133 A1 | 12/2007 |
| EP | 1875875 A1 | 1/2008 |
| EP | 1878399 A1 | 1/2008 |
| EP | 1915953 A1 | 4/2008 |
| EP | 1532933 B1 | 5/2008 |
| EP | 1199045 B1 | 6/2008 |
| EP | 1707143 B1 | 6/2008 |
| EP | 1943957 A2 | 7/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1477104 B1 | 1/2009 |
| EP | 2014218 A2 | 1/2009 |
| EP | 1849424 B1 | 4/2009 |
| EP | 2042112 A2 | 4/2009 |
| EP | 2042117 A1 | 4/2009 |
| EP | 2060238 A1 | 5/2009 |
| EP | 1832259 B1 | 6/2009 |
| EP | 2074959 A1 | 7/2009 |
| EP | 1810625 B1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 2106758 A1 | 10/2009 |
| EP | 2111813 A1 | 10/2009 |
| EP | 1769766 B1 | 2/2010 |
| EP | 2151204 A1 | 2/2010 |
| EP | 2153791 A1 | 2/2010 |
| EP | 2200145 A1 | 6/2010 |
| EP | 1214913 B1 | 7/2010 |
| EP | 2238938 A1 | 10/2010 |
| EP | 2243439 A1 | 10/2010 |
| EP | 2298154 A2 | 3/2011 |
| EP | 2305144 A1 | 4/2011 |
| EP | 1510178 B1 | 6/2011 |
| EP | 1946708 B1 | 6/2011 |
| EP | 2335630 A1 | 6/2011 |
| EP | 1502551 B1 | 7/2011 |
| EP | 1728475 B1 | 8/2011 |
| EP | 2353518 A1 | 8/2011 |
| EP | 2361562 A1 | 8/2011 |
| EP | 2365608 A2 | 9/2011 |
| EP | 2420197 A2 | 2/2012 |
| EP | 2422721 A2 | 2/2012 |
| EP | 1927321 B1 | 4/2012 |
| EP | 2529681 A1 | 12/2012 |
| EP | 1767164 B1 | 1/2013 |
| EP | 2316359 B1 | 3/2013 |
| EP | 2090238 B1 | 4/2013 |
| EP | 2578172 A2 | 4/2013 |
| EP | 1586275 B1 | 5/2013 |
| EP | 1616529 B1 | 9/2013 |
| EP | 1997438 B1 | 11/2013 |
| EP | 2508143 B1 | 2/2014 |
| EP | 2583633 B1 | 10/2014 |
| EP | 2113210 B1 | 3/2016 |
| EP | 2510891 B1 | 6/2016 |
| EP | 2227155 B1 | 7/2016 |
| EP | 2859858 B1 | 12/2016 |
| GB | 1482943 A | 8/1977 |
| GB | 2032221 A | 4/1980 |
| GB | 2317566 A | 4/1998 |
| GB | 2379878 B | 11/2004 |
| GB | 2425480 A | 11/2006 |
| GB | 2472216 A | 2/2011 |
| GB | 2447767 B | 8/2011 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04150847 A | 5/1992 |
| JP | H04152942 A | 5/1992 |
| JP | H0595955 A | 4/1993 |
| JP | H05115490 A | 5/1993 |
| JP | H0670938 A | 3/1994 |
| JP | H06104503 A | 4/1994 |
| JP | H06217988 A | 8/1994 |
| JP | H06507081 A | 8/1994 |
| JP | H07308323 A | 11/1995 |
| JP | H0824266 A | 1/1996 |
| JP | H08229050 A | 9/1996 |
| JP | H08275951 A | 10/1996 |
| JP | H08299351 A | 11/1996 |
| JP | H08336544 A | 12/1996 |
| JP | H08336545 A | 12/1996 |
| JP | H09135553 A | 5/1997 |
| JP | H09140722 A | 6/1997 |
| JP | H105237 A | 1/1998 |
| JP | H10295700 A | 11/1998 |
| JP | H11501543 A | 2/1999 |
| JP | H11128238 A | 5/1999 |
| JP | H11192235 A | 7/1999 |
| JP | H11253451 A | 9/1999 |
| JP | H11318918 A | 11/1999 |
| JP | 2000041991 A | 2/2000 |
| JP | 2000070279 A | 3/2000 |
| JP | 2000210299 A | 8/2000 |
| JP | 2000271145 A | 10/2000 |
| JP | 2000287987 A | 10/2000 |
| JP | 2001029353 A | 2/2001 |
| JP | 2001502216 A | 2/2001 |
| JP | 2001309925 A | 11/2001 |
| JP | 2002177295 A | 6/2002 |
| JP | 2002186901 A | 7/2002 |
| JP | 2002204808 A | 7/2002 |
| JP | 2002238919 A | 8/2002 |
| JP | 2002263579 A | 9/2002 |
| JP | 2002301086 A | 10/2002 |
| JP | 2002306504 A | 10/2002 |
| JP | 2002330977 A | 11/2002 |
| JP | 2002542690 A | 12/2002 |
| JP | 2003000612 A | 1/2003 |

(56) References Cited

FOREIGN PATENT DOCUMENTS

| | | |
|---|---|---|
| JP | 2003010201 A | 1/2003 |
| JP | 2003510158 A | 3/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003530921 A | 10/2003 |
| JP | 2003310627 A | 11/2003 |
| JP | 2003339730 A | 12/2003 |
| JP | 2004129871 A | 4/2004 |
| JP | 2004147701 A | 5/2004 |
| JP | 2005027026 A | 1/2005 |
| JP | 2005040222 A | 2/2005 |
| JP | 2005066316 A | 3/2005 |
| JP | 2005074088 A | 3/2005 |
| JP | 2005507679 A | 3/2005 |
| JP | 2005534451 A | 11/2005 |
| JP | 2006006410 A | 1/2006 |
| JP | 2006512149 A | 4/2006 |
| JP | 2006116194 A | 5/2006 |
| JP | 2006158525 A | 6/2006 |
| JP | 2006217716 A | 8/2006 |
| JP | 2006218296 A | 8/2006 |
| JP | 2006288431 A | 10/2006 |
| JP | 2007050181 A | 3/2007 |
| JP | 2007-524459 A | 8/2007 |
| JP | 2007229454 A | 9/2007 |
| JP | 2007527747 A | 10/2007 |
| JP | 2007296369 A | 11/2007 |
| JP | 2008018226 A | 1/2008 |
| JP | 2008036390 A | 2/2008 |
| JP | 2008508065 A | 3/2008 |
| JP | 2008119250 A | 5/2008 |
| JP | 2008515562 A | 5/2008 |
| JP | 2008521503 A | 6/2008 |
| JP | D1339835 S | 8/2008 |
| JP | 2008212679 A | 9/2008 |
| JP | 2008536562 A | 9/2008 |
| JP | 2008284374 A | 11/2008 |
| JP | 2009511206 A | 3/2009 |
| JP | 2009082711 A | 4/2009 |
| JP | 2009517181 A | 4/2009 |
| JP | 4262923 B2 | 5/2009 |
| JP | 2009523567 A | 6/2009 |
| JP | 2009148557 A | 7/2009 |
| JP | 2009236177 A | 10/2009 |
| JP | 2009254819 A | 11/2009 |
| JP | 2010000336 A | 1/2010 |
| JP | 2010009686 A | 1/2010 |
| JP | 2010514923 A | 5/2010 |
| JP | 2010121865 A | 6/2010 |
| JP | 2010534522 A | 11/2010 |
| JP | 2010540186 A | 12/2010 |
| JP | 2011505198 A | 2/2011 |
| JP | 2012/075899 A | 4/2012 |
| JP | 2012235658 A | 11/2012 |
| JP | 5208761 B2 | 6/2013 |
| JP | 5714508 B2 | 5/2015 |
| JP | 2015515339 A | 5/2015 |
| JP | 5836543 B1 | 12/2015 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2304934 C2 | 8/2007 |
| RU | 2405603 C1 | 12/2010 |
| SU | 850068 A1 | 7/1981 |
| WO | WO-8103272 A1 | 11/1981 |
| WO | WO-9222259 A2 | 12/1992 |
| WO | WO-9307817 A1 | 4/1993 |
| WO | WO-9308757 A1 | 5/1993 |
| WO | WO-9314708 A1 | 8/1993 |
| WO | WO-9316646 A1 | 9/1993 |
| WO | WO-9320877 A1 | 10/1993 |
| WO | WO-9322973 A1 | 11/1993 |
| WO | WO-9400059 A1 | 1/1994 |
| WO | WO-9421183 A1 | 9/1994 |
| WO | WO-9424949 A1 | 11/1994 |
| WO | WO-9509572 A1 | 4/1995 |
| WO | WO-9510978 A1 | 4/1995 |
| WO | WO-9534259 A1 | 12/1995 |
| WO | WO-9630885 A1 | 10/1996 |
| WO | WO-9635382 A1 | 11/1996 |
| WO | WO-9639086 A1 | 12/1996 |
| WO | WO-9710764 A1 | 3/1997 |
| WO | WO-9800069 A1 | 1/1998 |
| WO | WO-9816156 A1 | 4/1998 |
| WO | WO-9826739 A1 | 6/1998 |
| WO | WO-9835621 A1 | 8/1998 |
| WO | WO-9837815 A1 | 9/1998 |
| WO | WO-9840020 A1 | 9/1998 |
| WO | WO-9847436 A1 | 10/1998 |
| WO | WO-9857588 A1 | 12/1998 |
| WO | WO-9920213 A1 | 4/1999 |
| WO | WO-9923960 A1 | 5/1999 |
| WO | WO-9940857 A1 | 8/1999 |
| WO | WO-9940861 A1 | 8/1999 |
| WO | WO-9952489 A1 | 10/1999 |
| WO | WO-0024330 A1 | 5/2000 |
| WO | WO-0024331 A1 | 5/2000 |
| WO | WO-0025691 A1 | 5/2000 |
| WO | WO-0064358 A2 | 11/2000 |
| WO | WO-0074585 A2 | 12/2000 |
| WO | WO-0124713 A1 | 4/2001 |
| WO | WO-0128444 A1 | 4/2001 |
| WO | WO-0154590 A1 | 8/2001 |
| WO | WO-0167970 A1 | 9/2001 |
| WO | WO-0195810 A2 | 12/2001 |
| WO | WO-0224080 A2 | 3/2002 |
| WO | WO-0238057 A1 | 5/2002 |
| WO | WO-02062241 A1 | 8/2002 |
| WO | WO-02080797 A1 | 10/2002 |
| WO | WO-03001986 A2 | 1/2003 |
| WO | WO-03013374 A1 | 2/2003 |
| WO | WO-03020339 A2 | 3/2003 |
| WO | WO-03028541 A2 | 4/2003 |
| WO | WO-03030708 A2 | 4/2003 |
| WO | WO-03068046 A2 | 8/2003 |
| WO | WO-03082133 A2 | 10/2003 |
| WO | WO-2004011037 A2 | 2/2004 |
| WO | WO-2004012615 A1 | 2/2004 |
| WO | WO-2004026104 A2 | 4/2004 |
| WO | WO-2004032754 A2 | 4/2004 |
| WO | WO-2004032762 A1 | 4/2004 |
| WO | WO-2004032763 A2 | 4/2004 |
| WO | WO-2004037095 A2 | 5/2004 |
| WO | WO-2004060141 A2 | 7/2004 |
| WO | WO-2004078051 A2 | 9/2004 |
| WO | WO-2004098426 A1 | 11/2004 |
| WO | WO-2004112618 A2 | 12/2004 |
| WO | WO-2005052959 A2 | 6/2005 |
| WO | WO-2005117735 A2 | 12/2005 |
| WO | WO-2005122917 A1 | 12/2005 |
| WO | WO-2006012797 A1 | 2/2006 |
| WO | WO-2006021269 A1 | 3/2006 |
| WO | WO-2006036706 A1 | 4/2006 |
| WO | WO-2006042210 A1 | 4/2006 |
| WO | WO-2006055166 A2 | 5/2006 |
| WO | WO-2006058223 A2 | 6/2006 |
| WO | WO-2006063199 A2 | 6/2006 |
| WO | WO-2006083988 A1 | 8/2006 |
| WO | WO-2006101661 A2 | 9/2006 |
| WO | WO-2006119139 A2 | 11/2006 |
| WO | WO-2006119376 A2 | 11/2006 |
| WO | WO-2006129465 A1 | 12/2006 |
| WO | WO-2007008703 A2 | 1/2007 |
| WO | WO-2007008710 A2 | 1/2007 |
| WO | WO-2007038538 A1 | 4/2007 |
| WO | WO-2007040818 A1 | 4/2007 |
| WO | WO-2007047380 A2 | 4/2007 |
| WO | WO-2007047531 A2 | 4/2007 |
| WO | WO-2007056590 A1 | 5/2007 |
| WO | WO-2007087272 A2 | 8/2007 |
| WO | WO-2007089724 A2 | 8/2007 |

(56) References Cited

FOREIGN PATENT DOCUMENTS

| WO | WO-2007143665 | A2 | 12/2007 |
|---|---|---|---|
| WO | WO-2008016886 | A2 | 2/2008 |
| WO | WO-2008020964 | A2 | 2/2008 |
| WO | WO-2008042021 | A1 | 4/2008 |
| WO | WO-2008045348 | A2 | 4/2008 |
| WO | WO-2008049084 | A2 | 4/2008 |
| WO | WO-2008051764 | A2 | 5/2008 |
| WO | WO-2008089174 | A2 | 7/2008 |
| WO | WO-2008099529 | A1 | 8/2008 |
| WO | WO-2008101356 | A1 | 8/2008 |
| WO | WO-2008118709 | A1 | 10/2008 |
| WO | WO-2008130793 | A1 | 10/2008 |
| WO | WO-2009010565 | A1 | 1/2009 |
| WO | WO-2009018067 | A1 | 2/2009 |
| WO | WO-2009018406 | A2 | 2/2009 |
| WO | WO-2009022614 | A1 | 2/2009 |
| WO | WO-2009027065 | A1 | 3/2009 |
| WO | WO-2009036818 | A1 | 3/2009 |
| WO | WO-2009039179 | A1 | 3/2009 |
| WO | WO-2009046234 | A2 | 4/2009 |
| WO | WO-2009059741 | A1 | 5/2009 |
| WO | WO-2009073402 | A2 | 6/2009 |
| WO | WO-2009082477 | A2 | 7/2009 |
| WO | WO-2009088550 | A2 | 7/2009 |
| WO | WO-2009120992 | A2 | 10/2009 |
| WO | WO-2009141616 | A1 | 11/2009 |
| WO | WO-2009149234 | A1 | 12/2009 |
| WO | WO-2010017149 | A1 | 2/2010 |
| WO | WO-2010017266 | A1 | 2/2010 |
| WO | WO-2010068783 | A1 | 6/2010 |
| WO | WO-2010104755 | A1 | 9/2010 |
| WO | WO-2011008672 | A2 | 1/2011 |
| WO | WO-2011/044338 | A2 | 4/2011 |
| WO | WO-2011052939 | A2 | 5/2011 |
| WO | WO-2011060031 | A1 | 5/2011 |
| WO | WO-2011084768 | A1 | 7/2011 |
| WO | WO-2011089717 | A1 | 7/2011 |
| WO | WO-2011100321 | A2 | 8/2011 |
| WO | WO-2011144911 | A1 | 11/2011 |
| WO | WO-2012044597 | A1 | 4/2012 |
| WO | WO-2012044606 | A2 | 4/2012 |
| WO | WO-2012061722 | A2 | 5/2012 |
| WO | WO-2012128362 | A1 | 9/2012 |
| WO | WO-2012135705 | A1 | 10/2012 |
| WO | WO-2012135721 | A1 | 10/2012 |
| WO | WO-2012166510 | A1 | 12/2012 |
| WO | WO-2013018934 | A1 | 2/2013 |
| WO | WO-2013034629 | A1 | 3/2013 |
| WO | WO-2013062978 | A2 | 5/2013 |
| WO | WO-2013102602 | A2 | 7/2013 |
| WO | WO-2013154157 | A1 | 10/2013 |
| WO | WO-2014092108 | A1 | 6/2014 |
| WO | WO-2015197395 | A8 | 12/2015 |
| WO | WO-2016009921 | A1 | 1/2016 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
AST Products, Inc., "Principles of Video Contact Angle Analysis," 20 pages, (2006).
Campbell et al, "Thermal Imaging in Surgery," p. 19-3, in Medical Infrared Imaging, N. A. Diakides and J. D. Bronzino, Eds. (2008).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Heat-induced changes in the mechanics of a collagenous tissue: pseudoelastic behavior at 37° C," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Covidien 501 (k) Summary Sonicision, dated Feb. 24, 2011 (7 pages).
Covidien Brochure, [Value Analysis Brief], LigaSure Advance™ Pistol Grip, dated Rev. Apr. 2010 (7 pages).
Covidien Brochure, LigaSure Atlas™ Hand Switching Instruments, dated Dec. 2008 (2 pages).
Covidien Brochure, LigaSure Impact™ Instrument LF4318, dated Feb. 2013 (3 pages).
Covidien Brochure, The LigaSure Precise™ Instrument, dated Mar. 2011 (2 pages).
Covidien Brochure, The LigaSure™ 5 mm Blunt Tip Sealer/Divider Family, dated Apr. 2013 (2 pages).
Douglas, S.C. "Introduction to Adaptive Filter". Digital Signal Processing Handbook. Ed. Vijay K. Madisetti and Douglas B. Williams. Boca Raton: CRC Press LLC, 1999.
Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.
F. A. Duck, "Optical Properties of Tissue Including Ultraviolet and Infrared Radiation," pp. 43-71 in Physical Properties of Tissue (1990).
Fowler, K.R., "A Programmable, Arbitrary Waveform Electrosurgical Device," IEEE Engineering in Medicine and Biology Society 10th Annual International Conference, pp. 1324, 1325 (1988).
Gerhard, Glen C., "Surgical Electrotechnology: Quo Vadis?," IEEE Transactions on Biomedical Engineering, vol. BME-31, No. 12, pp. 787-792, Dec. 1984.
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Glaser and Subak-Sharpe, Integrated Circuit Engineering, Addison-Wesley Publishing, Reading, MA (1979). (book--not attached).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Graff, K.F., "Elastic Wave Propagation in a Curved Sonic Transmission Line," IEEE Transactions on Sonics and Ultrasonics, SU-17(1), 1-6 (1970).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Henriques. F.C., "Studies in thermal injury V. The predictability and the significance of thermally induced rate processes leading to irreversible epidermal injury." Archives of Pathology, 434, pp. 489-502 (1947).
http://www.4-traders.com/JOHNSON-JOHNSON-4832/news/Johnson-Johnson-Ethicon-E . . . .
http://www.apicalinstr.com/generators.htm.
http://www.dotmed.com/listing/electrosurical-unit/ethicon/ultracision-g110-/1466724.
http://www.medicalexpo.com/medical-manufacturer/electrosurgical-generator-6951.html.
http://www.megadyne.com/es_generator.php.
http://www.valleylab.com/product/es/generators/index.html.
http:/www.ethicon.com/gb-en/healthcare-professionals/products/energy-devices/capital//ge . . . .
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

(56) References Cited

OTHER PUBLICATIONS

Humphrey, J.D., "Continuum Thermomechanics and the Clinical Treatment of Disease and Injury," Appl. Mech. Rev., vol. 56, No. 2 pp. 231-260 (Mar. 2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book--not attached).
Jang, J. et al. "Neuro-fuzzy and Soft Computing." Prentice Hall, 1997, pp. 13-89, 199-293, 335-393, 453-496, 535-549.
Kurt Gieck & Reiner Gieck, *Engineering Formulas* § Z.7 (7th ed. 1997).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Lee et al., "A multi-sample denaturation temperature tester for collagenous biomaterials," Med. Eng. Phy., vol. 17, No. 2, pp. 115-121 (Mar. 1995).
Leonard I. Malis, M.D., "The Value of Irrigation During Bipolar Coagulation," 1989.
Lim et al., "A Review of Mechanism Used in Laparoscopic Surgical Instruments," Mechanism and Machine Theory, vol. 38, pp. 1133-1147, (2003).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Moran et al., "Thermally Induced Shrinkage of Joint Capsule," Clinical Orthopaedics and Related Research, No. 281, pp. 248-255 (Dec. 2000).
Morley, L. S. D., "Elastic Waves in a Naturally Curved Rod," Quarterly Journal of Mechanics and Applied Mathematics, 14: 155-172 (1961).
National Semiconductors Temperature Sensor Handbook—http://www.national.com/appinfo/tempsensors/files/temphb.pdf; accessed online: Apr. 1, 2011.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Technology Overview, printed from www.harmonicscalpel.com, Internet site, website accessed on Jun. 13, 2007, (3 pages).
Wall et al., "Thermal modification of collagen," J Shoulder Elbow Surg, No. 8, pp. 339-344 (Jul./Aug. 1999).
Walsh, S. J., White, R. G., "Vibrational Power Transmission in Curved Beams," Journal of Sound and Vibration, 233(3), 455-488 (2000).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Wright, et al., "Time-Temperature Equivalence of Heat-Induced Changes in Cells and Proteins," Feb. 1998. ASME Journal of Biomechanical Engineering, vol. 120, pp. 22-26.

\* cited by examiner

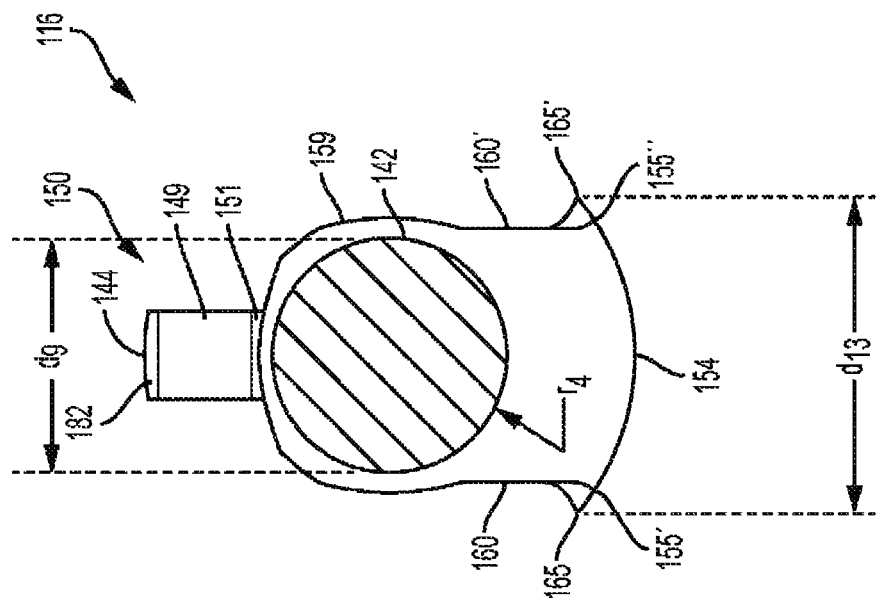

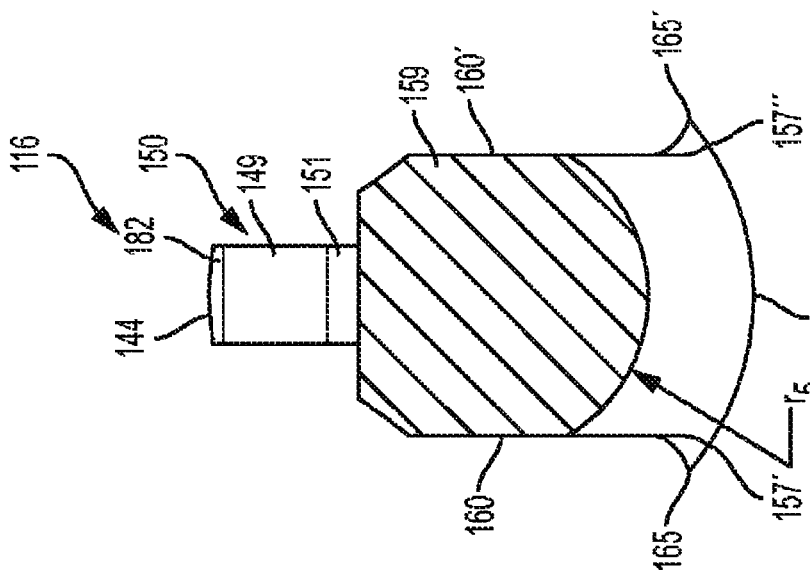
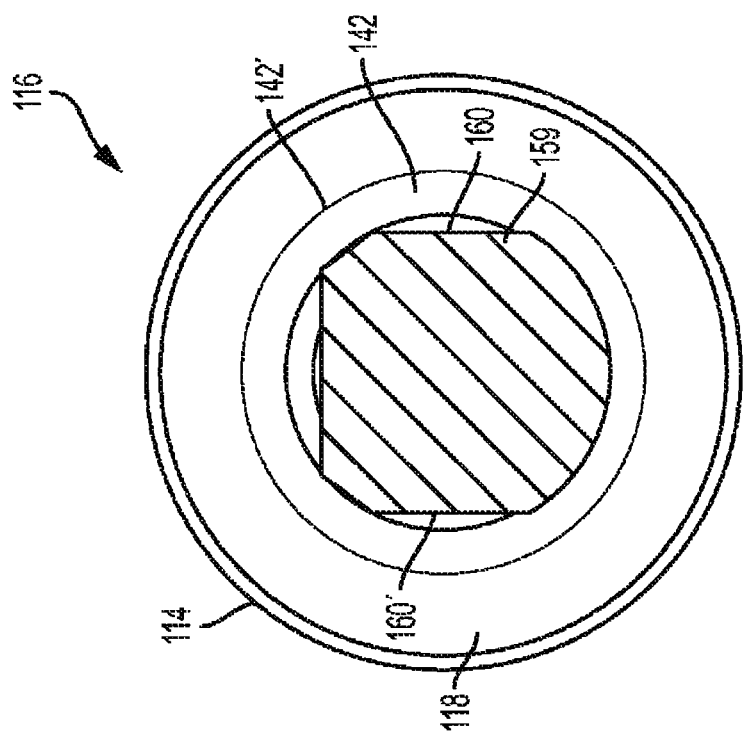

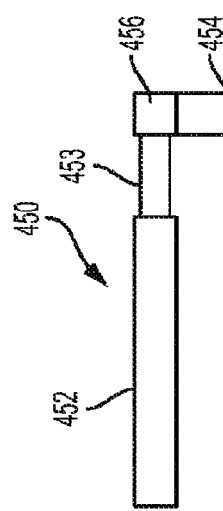
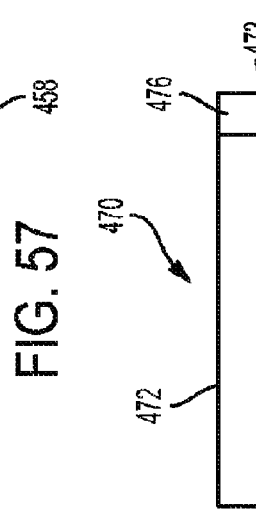
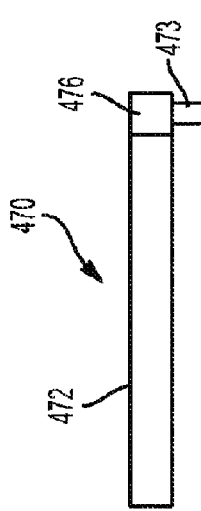
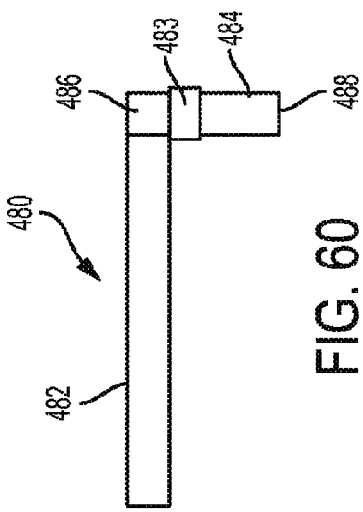

ULTRASONIC SURGICAL BLADE WITH IMPROVED CUTTING AND COAGULATION FEATURES

INTRODUCTION

The present disclosure is related generally to ultrasonic blades for use in surgical instruments. In particular, the present disclosure is related to ultrasonic surgical blades for use in surgical instruments and, more particularly, to an ultrasonic surgical blade with improved cutting and coagulation features.

BACKGROUND

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic instruments utilizing solid core technology are particularly advantageous because of the amount of ultrasonic energy that may be transmitted from the ultrasonic transducer, through the waveguide, to the surgical end-effector. Such instruments may be used for open procedures or minimally invasive procedures, such as endoscopic or laparoscopic procedures, wherein the end-effector is passed through a trocar to reach the surgical site.

Activating the end-effector (e.g., cutting blade) of such instruments at ultrasonic frequencies induces longitudinal vibratory movement that generates localized heat within adjacent tissue, facilitating both cutting and coagulation. Because of the nature of ultrasonic instruments, a particular ultrasonically actuated end-effector may be designed to perform numerous functions, including, for example, cutting and coagulation. The structural stress induced in such end-effectors by vibrating the blade at ultrasonic frequencies may have a number of undesirable effects. Such undesirable effects may include, for example, transverse motion in the instrument waveguide that may lead to, for example, excess heat generation in the waveguide or premature stress failure.

Although ultrasonic surgical instruments have been eminently successful, some areas of improvement still remain. For example, it would be desirable for improved ultrasonic blades to remove the gall bladder from the liver bed and for coagulation to facilitate the procedure. An ultrasonic blade that enables efficient dissection of the gall bladder from the liver bed using proximal and distal surfaces facilitates the surgical technique. An ultrasonic blade which has a hook or right angle or near right angle bend near the distal end would provide advantages for access and visibility. The challenges to providing such a configuration have been stress and balance related. An ultrasonic blade with such a configuration must be behave in a balanced manner and be sufficiently strong to endure the added stresses. It would, therefore, be desirable to design an improved ultrasonic surgical blade. It would further be advantageous to provide an ultrasonic surgical blade that cuts faster, while maintaining hemostasis desired by the surgeon. It would also be advantageous to provide an ultrasonic surgical blade that is more controllable and precise, to providing cutting where needed with significant control. An ultrasonic surgical instrument is described with improved cutting and coagulation features to provide these advantages and overcome the disadvantages of previous instruments.

SUMMARY

Various embodiments of ultrasonic surgical blades are disclosed.

1. In one example, an ultrasonic surgical blade comprises a solid body; a longitudinal portion having a proximal end configured to couple to an ultrasonic transmission waveguide and a distal end configured to dissect and coagulate tissue, the longitudinal portion comprising: a substantially planar longitudinal surface; and a distal hemostasis surface located opposite of the substantially planar longitudinal surface; a transverse portion extending crosswise from the distal end of the longitudinal portion, the transverse portion defining a hook having a free end configured to pull and dissect tissue, the transverse portion comprising: a curved section extending from a distal end of the substantially planar longitudinal surface; a tip surface defined at the free end; a substantially planar proximal inner surface extending from the curved surface to the tip surface; and an outer concave distal surface extending from the tip surface to the distal hemostasis surface; and a distal dissection edge defined at a surface inflection of the outer concave distal surface and the distal hemostasis surface.

2. In another example, the ultrasonic surgical blade of example 1 is disclosed, wherein the longitudinal portion comprises a proximal hemostasis surface located opposite of the substantially planar longitudinal surface.

3. In another example, the ultrasonic surgical blade of example 2 is disclosed, comprising first and second lateral surfaces extending from the body to the proximal hemostasis surface defining first and second cutting edges defined at first and second surface inflections between the first and second lateral surfaces and the proximal hemostasis surface.

4. In another example, the ultrasonic surgical blade of example 2 is disclosed, wherein the distal hemostasis surface has a surface area S1 selected form a range of 3.226 mm$^2$ to 6.45 mm$^2$ (0.005 in$^2$ to 0.01 in$^2$).

5. In another example, the ultrasonic surgical blade of example 1 is disclosed, further comprising a beveled edge defined between the tip surface and the substantially planar proximal inner surface.

6. In another example, the ultrasonic surgical blade of example 1 is disclosed, further comprising an oblique tip surface extending from the tip surface to the outer concave distal surface.

7. In another example, the ultrasonic surgical blade of example 1 is disclosed, wherein the depth of the transverse portion measured from the tip surface to the proximal hemostasis surface is selected from a range of 1.8 mm to 3.0 mm (0.071 in to 0.118 in).

8. In another example, the ultrasonic surgical blade of example 1 is disclosed, wherein the proximal hemostasis surface has a surface area S2 selected form a range of 6.45 mm$^2$ to 12.90 mm$^2$ (0.01 in$^2$ to 0.02 in$^2$).

9. In one example, an ultrasonic surgical blade comprises a solid body; a longitudinal portion having a proximal end and a distal end, the longitudinal portion comprising: a substantially planar longitudinal surface; and a distal hemostasis surface located opposite of the substantially planar longitudinal surface; a transverse portion extending crosswise from the distal end of the longitudinal portion, the transverse portion defining a hook having a free end, the transverse portion comprising: a curved section extending from a distal end of the substantially planar longitudinal surface; a tip surface defined at the free end; a proximal inner surface extending from the curved surface to the tip surface; and an outer convex distal surface extending from the tip surface to the distal hemostasis surface.

10. In another example, the ultrasonic surgical blade of example 9 is disclosed, wherein the longitudinal portion comprises a proximal hemostasis surface located opposite of the substantially planar longitudinal surface.

11. In another example, the ultrasonic surgical blade of example 10 is disclosed, comprising first and second lateral surfaces extending from the body to the proximal hemostasis surface defining first and second cutting edges defined at first and second surface inflections between the first and second lateral surfaces and the proximal hemostasis surface.

12. In another example, the ultrasonic surgical blade of example 10 is disclosed, wherein the distal hemostasis surface has a surface area S1 selected form a range of 0.005 in$^2$ to 0.01 in$^2$ (3.226 mm$^2$ to 6.45 mm$^2$).

13. In another example, the ultrasonic surgical blade of example 9 is disclosed, wherein the depth of the transverse portion measured from the tip surface to the proximal hemostasis surface is selected from a range of 1.8 mm to 3.0 mm (0.071 in to 0.118 in).

14. In another example, the ultrasonic surgical blade of example 9 is disclosed, wherein the proximal hemostasis surface has a surface area S2 selected form a range of 0.01 in$^2$ to 0.02 in$^2$ (6.45 mm$^2$ to 12.90 mm$^2$).

15. In one example, an ultrasonic surgical blade comprises a solid body; a longitudinal portion having a proximal end and a distal end, the longitudinal portion comprising: a sharp central ridge; a distal hemostasis surface located opposite of the substantially planar longitudinal surface; and an end mass located at the distal end of the longitudinal portion; and a transverse portion extending crosswise from the distal end of the longitudinal portion and located opposite of the end mass, the transverse portion defining a hook having a free end, the transverse portion comprising a tip surface defined at the free end.

16. In another example, the ultrasonic surgical blade of example 15 is disclosed, wherein the sharp central ridge comprise at least two segments extending from a neck portion of the body to the tip surface of the hook.

17. In another example, the ultrasonic surgical blade of example 16 is disclosed, wherein the sharp central ridge comprises a proximal segment, an intermediate arcuate segment, and a distal linear segment.

18. In another example, the ultrasonic surgical blade of example 16 is disclosed, wherein the proximal segment is defined by a junction of two proximal oblique surfaces that extend downwardly and outwardly from the proximal segment, the intermediate arcuate segment is defined by a junction of intermediate arcuate oblique surfaces that extend downwardly and outwardly from the intermediate arcuate segment, and the distal linear segment is defined by a junction of distal oblique surfaces that extend distally and outwardly from the distal linear segment.

19. In another example, the ultrasonic surgical blade of example 15 is disclosed, wherein the depth of the transverse portion measured from the tip surface to the proximal hemostasis surface is selected from a range of 1.8 mm to 3.0 mm (0.071 in to 0.118 in).

20. In another example, the ultrasonic surgical instrument of example 15 is disclosed, where in the hemostasis surface is located on a surface portion of the end mass.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 17 is a sectional view of the ultrasonic surgical blade shown in FIG. 16 taken along section line 17-17, according to one embodiment.

FIG. 18 is a sectional view of the ultrasonic surgical blade shown in FIG. 16 taken along section line 18-18, according to one embodiment.

FIG. 19 is a sectional view of the ultrasonic surgical blade shown in FIG. 16 taken along section line 19-19, according to one embodiment.

FIG. 20 is a sectional view of the ultrasonic surgical blade shown in FIG. 16 taken along section line 20-20, according to one embodiment.

Figure 53:
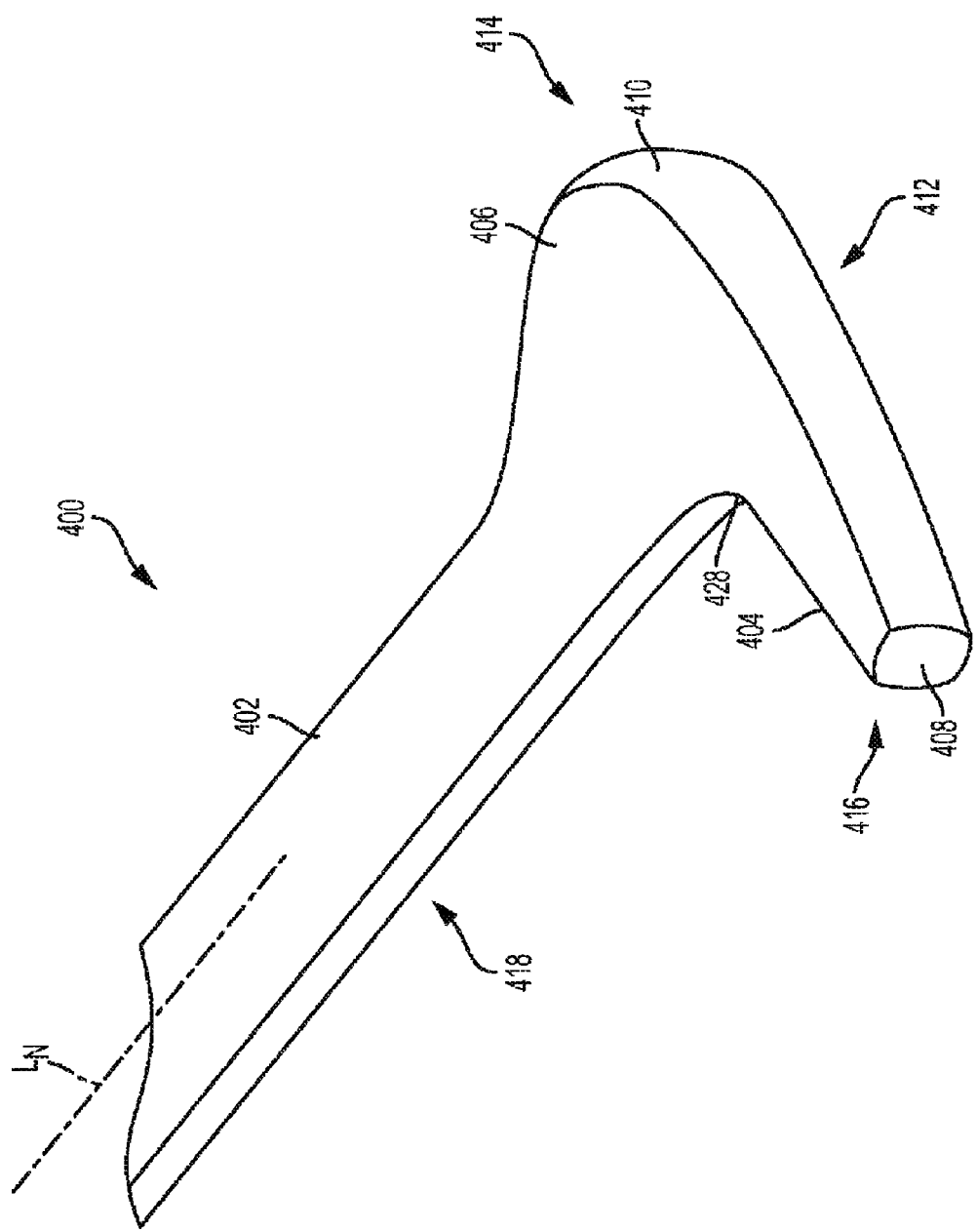

FIG. 53. Illustrates one embodiment of a right angle balance blade.

Figure 54:
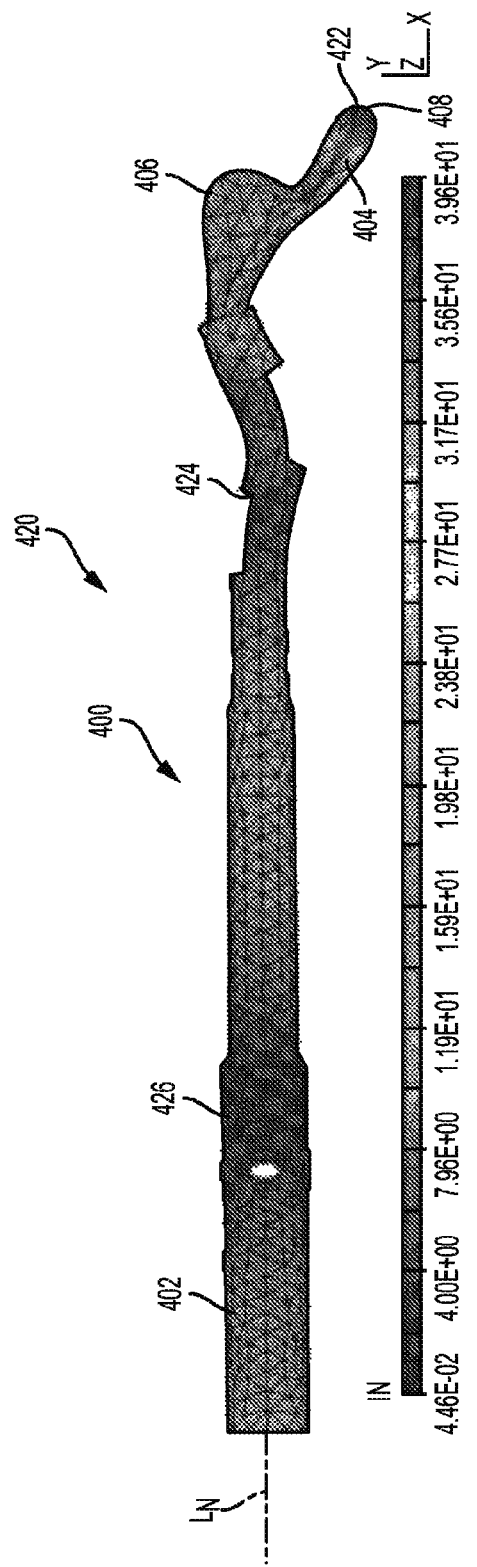

FIG. 54 is an illustration of a balanced displacement plot of a right angle balanced blade, similar to the blade shown FIG. 53, in a maximum displacement state, according to one embodiment.

Figure 55:
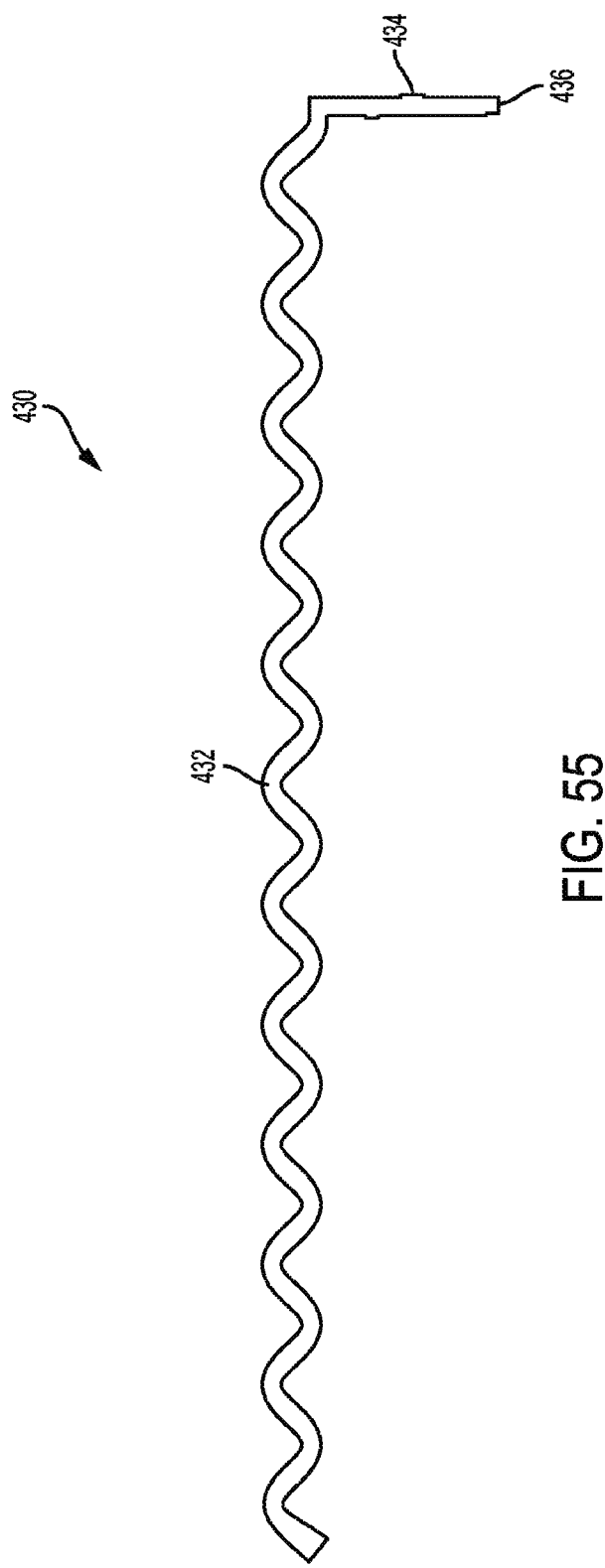

FIG. 55 illustrates a right angle balanced ultrasonic blade driven in transverse mode to produce longitudinal motion at an end effector section, according to one embodiment.

FIG. 56 illustrates one configuration of a right angle balanced ultrasonic surgical blade.

FIG. 57 illustrates one configuration of a right angle balanced ultrasonic surgical blade.

FIG. 58 illustrates one configuration of a right angle balanced ultrasonic surgical blade.

FIG. 59 illustrates one configuration of a right angle balanced ultrasonic surgical blade.

FIG. 60 illustrates one configuration of a right angle balanced ultrasonic surgical blade.

DESCRIPTION

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

Figure 1:
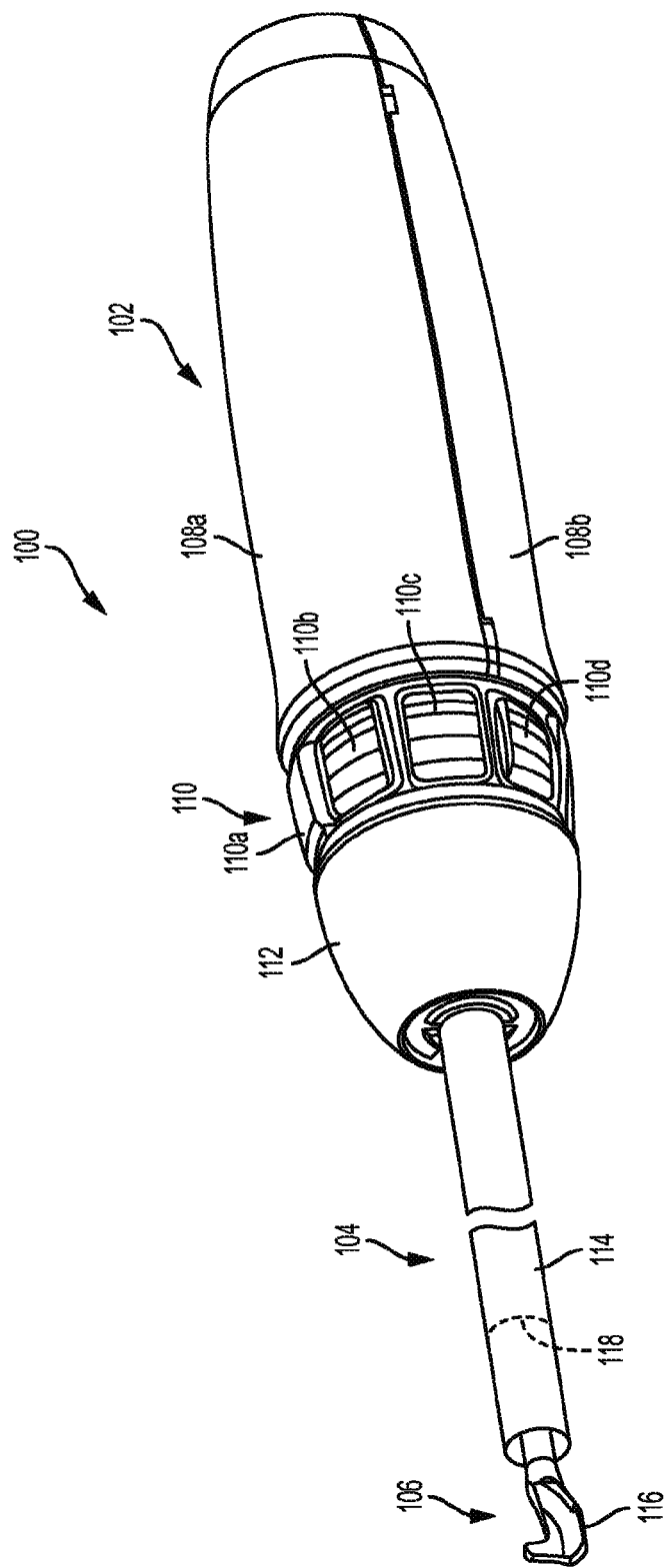
FIG. 1 is an illustration of an ultrasonic instrument according to one embodiment.
Figure 5:
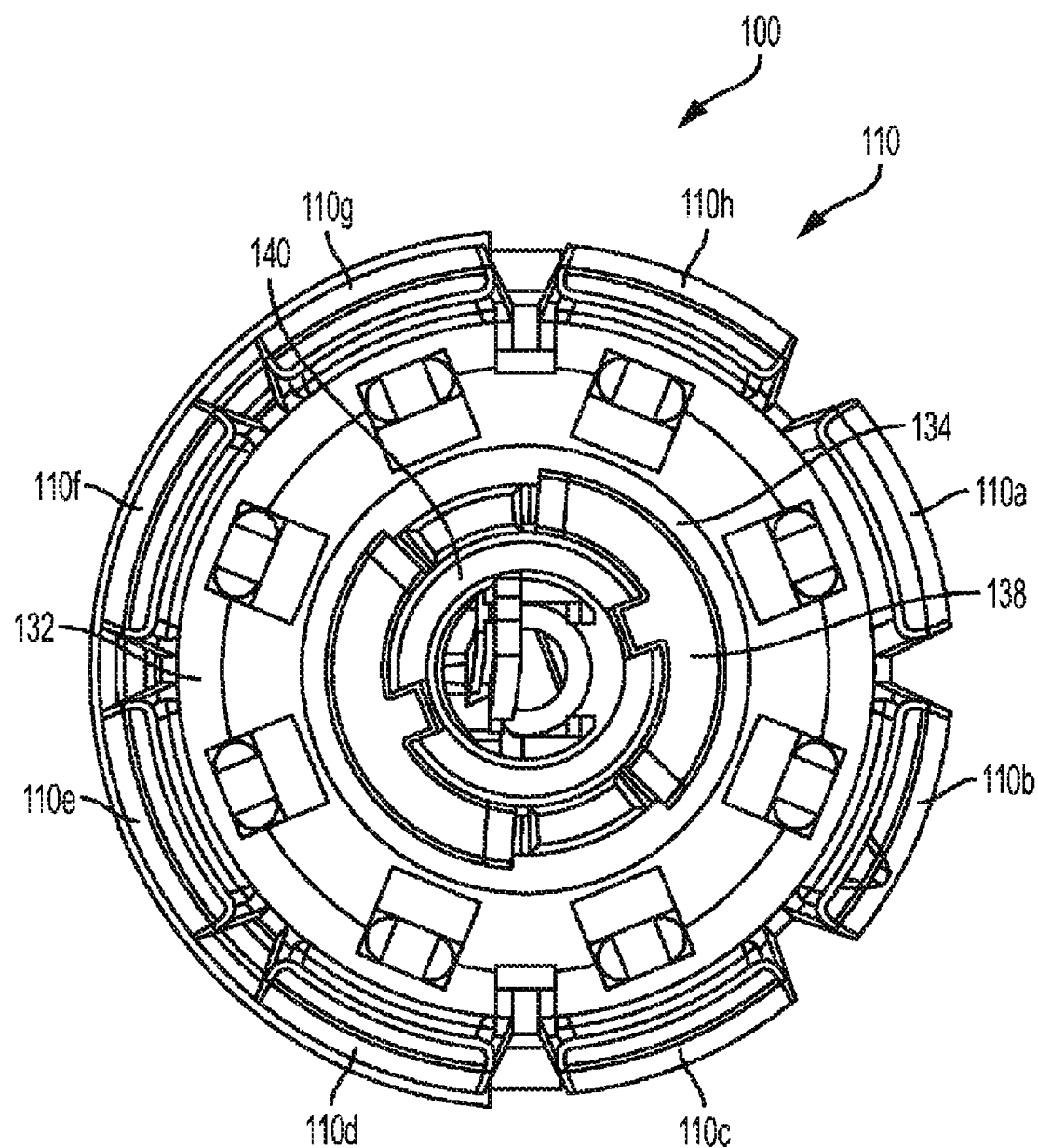
FIG. 5 is a front view of the ultrasonic surgical instrument shown in FIG. 1 with the nose cone removed to show the underlying activation button assembly, the clutch plate, retainer, and support bushing.

The present disclosure provides an ultrasonic instrument comprising an ultrasonic blade with improved cutting and coagulation features. FIG. 1 is an illustration of an ultrasonic instrument 100 according to one embodiment. The ultrasonic instrument 100 comprises a handle assembly 102, a shaft assembly 104, and a surgical end-effector 106. The handle assembly 102 comprises right and left shrouds 108a, 108b, an activation button assembly 110, and a nose cone 112. The activation button assembly 110 comprises a plurality of activation buttons. Turning briefly to FIG. 5, which is a front view of the ultrasonic instrument, it can be seen that in one embodiment, the activation button assembly 110 comprises eight activation buttons 110a, 110b, 110c, 110d, 110e, 110f, 110g, 110h distributed about the handle assembly 102. Turning back to FIG. 1, the shaft assembly 104 comprises an outer sheath 114. The surgical end-effector 106 comprises an ultrasonic surgical blade 116 with improved cutting and coagulation features. The ultrasonic surgical blade 116 and ultrasonic transmission waveguide is isolated from the outer sheath 114 with multiple isolation spacers 118, which can be overmolded over the ultrasonic transmission waveguide.

The handle assembly 102 also comprises an ultrasonic transducer acoustically coupled to an ultrasonic transmission waveguide which is acoustically coupled to the surgical end-effector 106. The handle assembly 102 is electrically connected to an ultrasonic energy generator, which can be activated by one of the plurality of activation buttons 110a-110h, for example the activation button 110a. Depressing the activation button 110a activates the ultrasonic generator, and delivers electrical energy to an ultrasonic transducer located in the handle assembly 102. The ultrasonic transducer in the handle assembly 102 converts the electrical energy to ultrasonic motion, which is acoustically coupled to the ultrasonic transmission assembly and the treatment region of the surgical end-effector 106. The treatment region vibrates at an excursion magnitude of 20 micrometers to 150 micrometers, and at a frequency of approximately 55.5 kilohertz, although other frequencies may be employed, without departing from the scope of the present disclosure.

Figure 2:
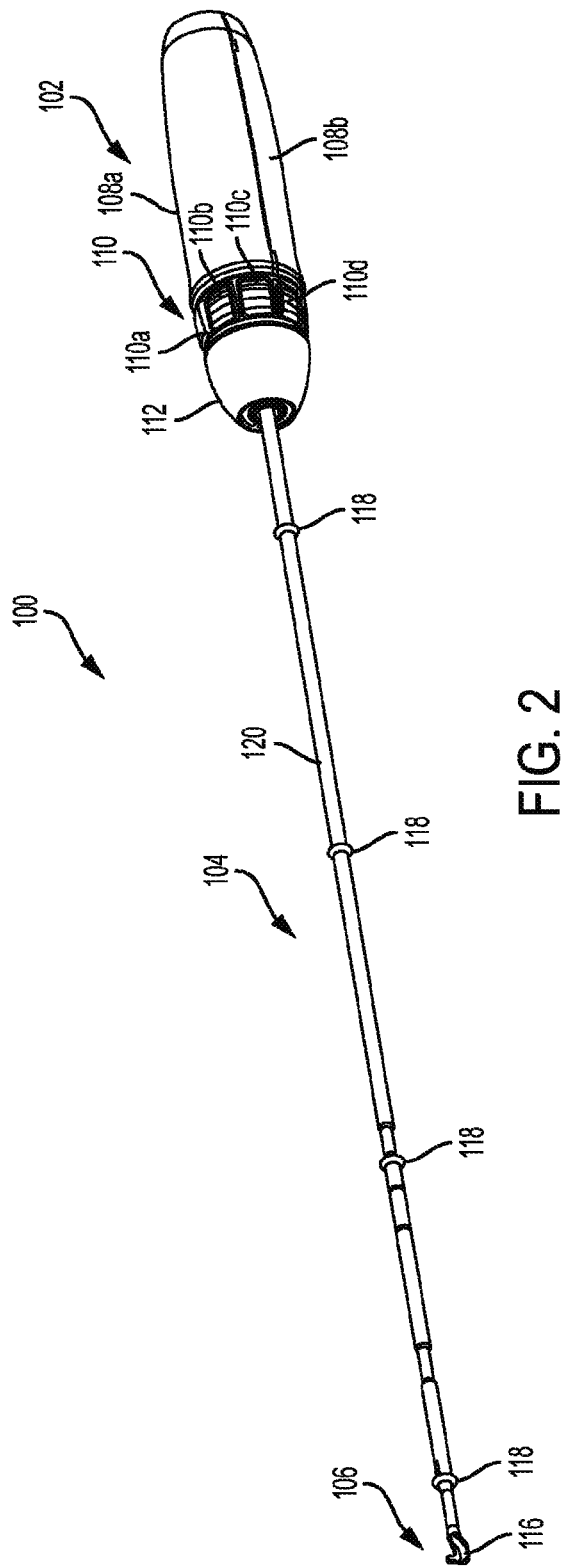
FIG. 2 is an illustration of the ultrasonic instrument shown in FIG. 1, with the outer sheath removed to reveal the underlying ultrasonic transmission waveguide.

FIG. 2 is an illustration of the ultrasonic instrument 100 shown in FIG. 1, with the outer sheath 114 (FIG. 1) removed to reveal the underlying ultrasonic transmission waveguide 120. As shown, isolation spacers 118 are disposed over the ultrasonic transmission waveguide 120 to acoustically isolate the outer sheath 114 from the ultrasonic transmission waveguide 120. Accordingly, the plurality of isolation spacers 118 are located on respective nodes along the ultrasonic transmission waveguide 120 to minimize the vibrations acoustically coupled to the outer sheath 114. In one embodiment, the isolation spacers 118 may be overmolded over the ultrasonic transmission waveguide 120.

Figure 3:
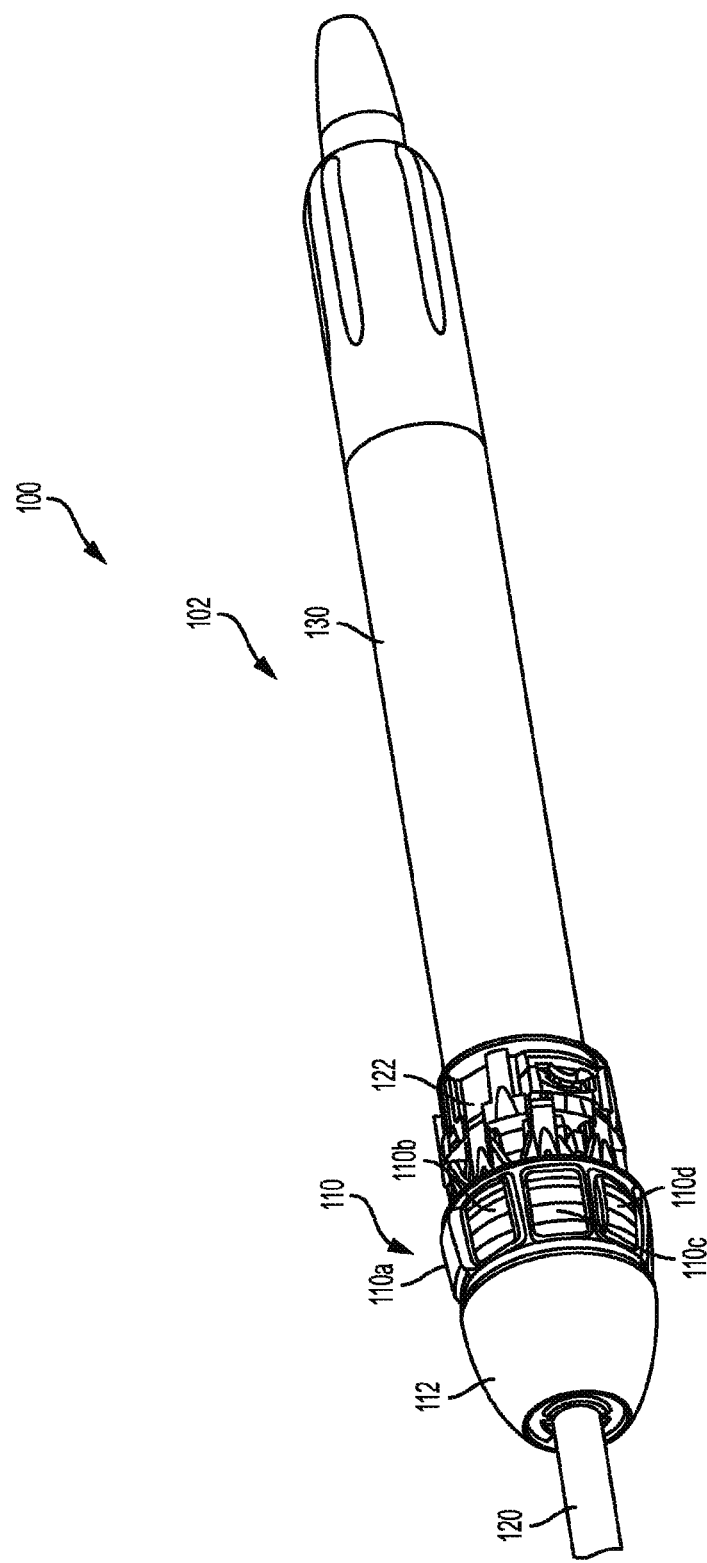
FIG. 3 is an illustration of the ultrasonic surgical instrument shown in FIG. 1 with the right and left shrouds removed.

FIG. 3 is an illustration of the ultrasonic surgical instrument 100 shown in FIG. 1 with the right and left shrouds 108a, 108b removed. The handle assembly 102 includes a support base 122 located proximal to the activation button assembly 110.

Figure 4:
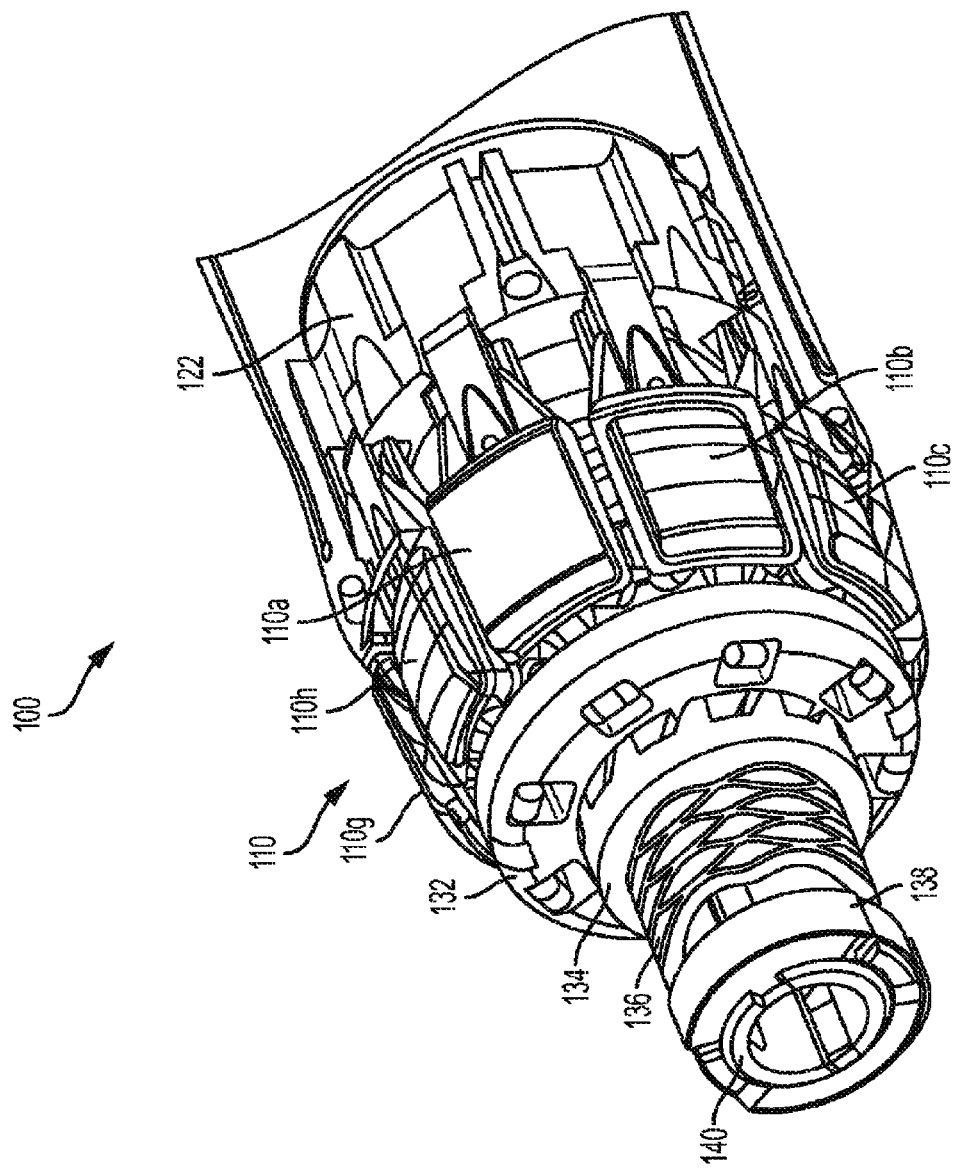
FIG. 4 is an illustration of the handle assembly of the ultrasonic surgical instrument shown in FIG. 1 with the left shroud, the shaft assembly, and the nose cone removed.

FIG. 4 is an illustration of the handle assembly 102 of the ultrasonic surgical instrument 100 shown in FIG. 1 with the left shroud 108b (FIG. 1), the shaft assembly 102 (FIG. 1), and the nose cone 112 removed. As shown in FIG. 4, below the nose cone 112 is a bridge guide 132 operatively coupled to the activation button assembly 110. A clutch plate 134 and clutch spring 136 are disposed between the bridge guide 132 and a retainer 138. A support bushing 140 supports the shaft assembly 102.

FIG. 5 is a front view of the ultrasonic surgical instrument 100 shown in FIG. 1 with the nose cone 112 removed to show the underlying activation button assembly 110, the clutch plate 134, retainer 138, and support bushing 140. The activation button assembly 110 comprises a plurality activation buttons 110a-110h, that are individually programmable to perform a particular function. For example, the activation 110a is electrically coupled to the ultrasonic generator and is used to energize the ultrasonic transducer to activate the surgical end-effector 106.

Having described one embodiment of an ultrasonic surgical instrument 100 (FIGS. 1-5) that can be configured to operate a surgical end-effector 106, the present disclosure now turns to a description of one embodiment of a surgical end-effector 106 in connection with FIGS. 6-32.

Ultrasonic Blade for Tissue Dissection and Hemostasis (Embodiment 1)

FIGS. 6-32 illustrate one embodiment of the ultrasonic surgical blade 116 configured with edges and surfaces to optimize hemostasis and dissection. In one use, the distal portion allows access to surface tissue, such as the liver bed, for efficient hemostasis. Sharp edges disposed on the distal portion of the ultrasonic surgical blade 116 deliver quick dissection. Accordingly, the disclosed ultrasonic blade 116 enables efficient dissection of the gall bladder from the liver bed using proximal and distal surfaces for ease of surgeon technique.

Figure 6:
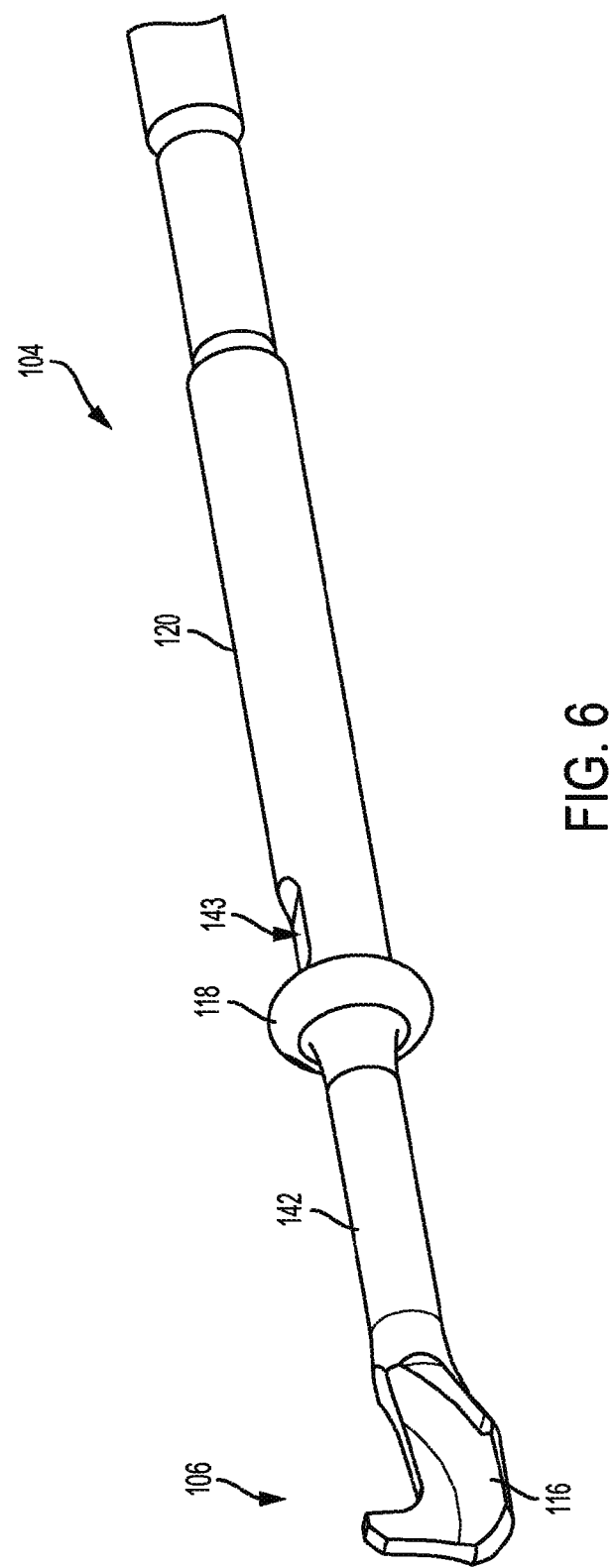
FIG. 6 illustrates one embodiment of a surgical end-effector integrally formed with an ultrasonic transmission waveguide.

FIG. 6 illustrates one embodiment of a surgical end-effector 106 integrally formed with an ultrasonic transmission waveguide 120. The surgical end-effector 106 comprises an ultrasonic surgical blade 116 having a neck 142 coupled to the ultrasonic transmission waveguide 120. The ultrasonic transmission waveguide 120 is a component of the shaft assembly 104 and is acoustically isolated from other components of the shaft assembly 104, such as the outer sheath 114 (FIG. 1), by the isolation spacer 118. The ultrasonic surgical blade 116 is configured to vibrate in response to ultrasonic energy applied thereto via the ultrasonic transmission waveguide 120. A balance feature 143 is defined as a cutout section in the ultrasonic transmission waveguide 120 to facilitate the expansion and contraction of the ultrasonic transmission waveguide 120 during the vibratory process.

Figure 7:
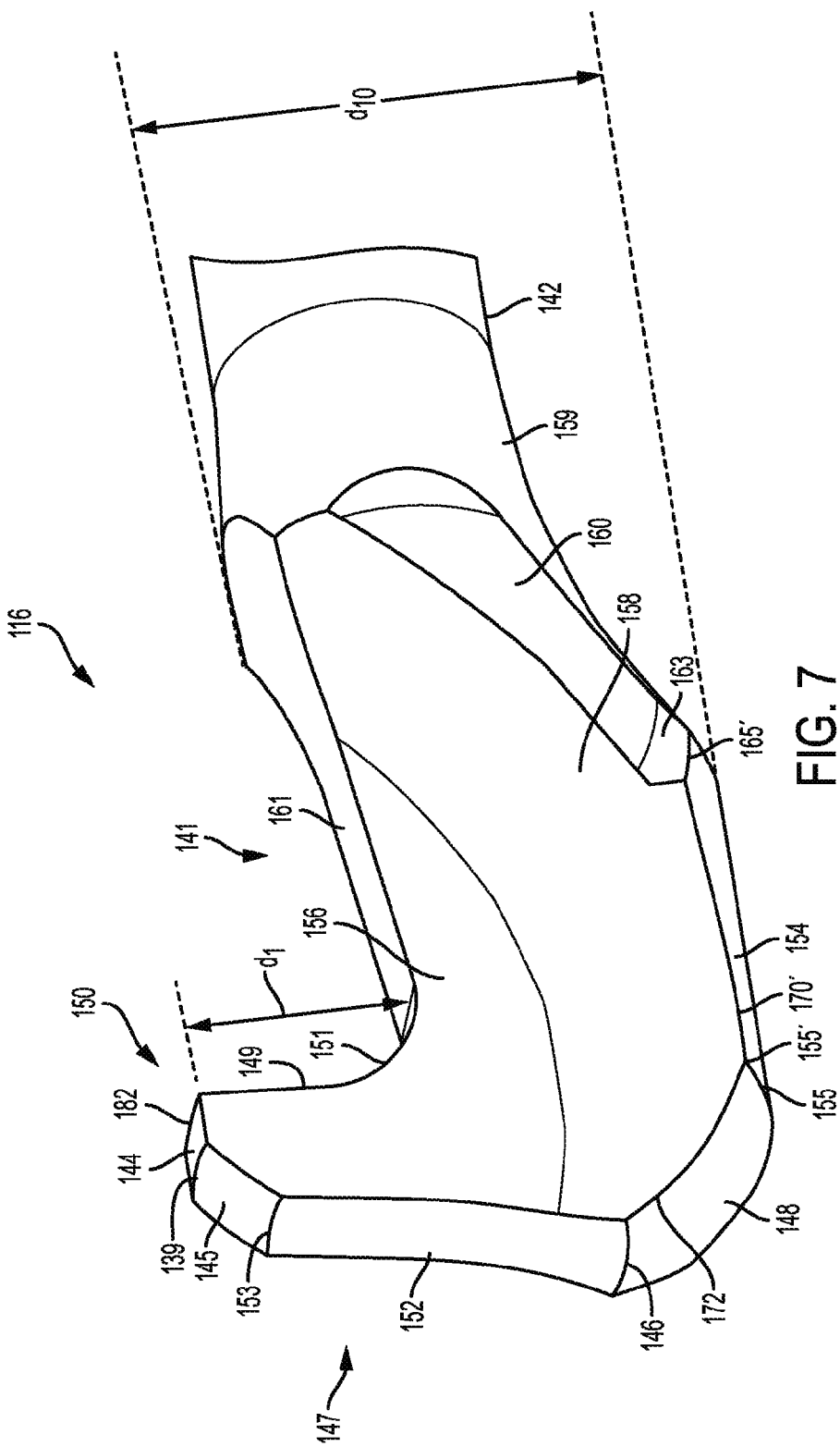
FIG. 7 is a perspective view of an ultrasonic surgical blade according to one embodiment.

FIG. 7 is a perspective view of an ultrasonic surgical blade 116 according to one embodiment. The distal portion of the ultrasonic surgical blade 116 has a curved or angular shape that defines a blade hook 150 having a free end configured for pulling and cutting tissue during use. The ultrasonic surgical blade 116 comprises a longitudinal portion 141 extending distally from the neck 142, where it couples to ultrasonic vibrations and a transverse portion 147 extending from a distal end of the longitudinal portion 141. The transverse portion 147 of the ultrasonic surgical blade 116 defines the blade hook 150. At the end of the transverse portion, the blade hook 150 defines a tip surface 144 optimized to access tissue planes. From the tip surface 144, extending outwardly and towards the longitudinal portion 141, the tip surface 144 transitions at a surface inflection 139 to an oblique tip surface 145 having a convex radius of curvature. Extending from the oblique tip surface 145, at another surface inflection 153, the blade hook 150 defines an outer distal surface 152 on a distal side of the blade hook 150, where the outer distal surface 152 defines a contour profile configured to facilitate access to tissue planes. The distal surface 152 has a concave radius of curvature that defines a reduced size contour profile to facilitate better access to tissue planes. An angle $\theta_1$ is defined by the tip surface 144 and the oblique tip surface.

Extending from the outer distal surface 152 through yet another surface inflection is a distal hemostasis surface 148 defining a larger surface area. The distal hemostasis surface 148 has a convex radius of curvature. A dissection edge 146 is defined at the surface inflection between the outer distal surface 152 and the distal hemostasis surface 148. The dissection edge 146 is configured to improve the dissection or cutting speed. The contour profile of the outer distal surface 152 extends distally at the surface inflection defining the dissection edge 146 such that the transverse portion 147 of the hook 150 is tapered from the dissection edge 146 to the oblique tip surface 145. From the surface inflection 153, the oblique tip surface 145 extends at an angle to the tip surface 144. The proximal end of the tip surface 144 defines a beveled edge 182. The inner, proximal, portion of the blade hook 150 defines a substantially planar inner surface 149 on the proximal side of the blade hook 150 that extends along the transverse portion 147 from the beveled edge 182 of the tip surface 144 to a curved surface 151 having a concave radius of curvature $r_1$. The depth $d_1$ of the transverse portion 147 measured from the tip surface 144 to the planar longitudinal surface 161 may be optimized to pull tissue of various types. A proximal hemostasis surface 154 is provided on the longitudinal portion 141 of the ultrasonic surgical blade 116 and is sized to deliver suitable hemostasis while minimizing mass.

The ultrasonic surgical blade 116 also may comprise additional surfaces designed to acoustically balance the ultrasonic surgical blade 116. These surfaces include a first lateral surface 156, a second lateral surface 158, and a third lateral surface 160 located on one side of the ultrasonic surgical blade 116 and corresponding lateral surfaces on the other side of the ultrasonic surgical blade 116, which are labeled by a prime ('). The lateral surfaces 160, 160' are oblique and extend from a proximal body portion 159 of the blade 116 to the proximal hemostasis surface 154. Cutting edges 165, 165' are defined at the surface inflections of the proximal hemostasis surface 154 and the oblique lateral surfaces 160, 160'. The lateral surfaces 156, 156' 158, 158', 160, 160' are produced by removing mass from the blade body 159 and are contoured to balance the ultrasonic surgical blade 116 to provide stable ultrasonic vibrations when energized. The substantially planar longitudinal surface 161 is part of the longitudinal portion 141 of the ultrasonic surgical blade 116 extending from the neck 142 towards the curved surface 151 of the transverse portion 147 of the blade hook 150.

Figure 8:
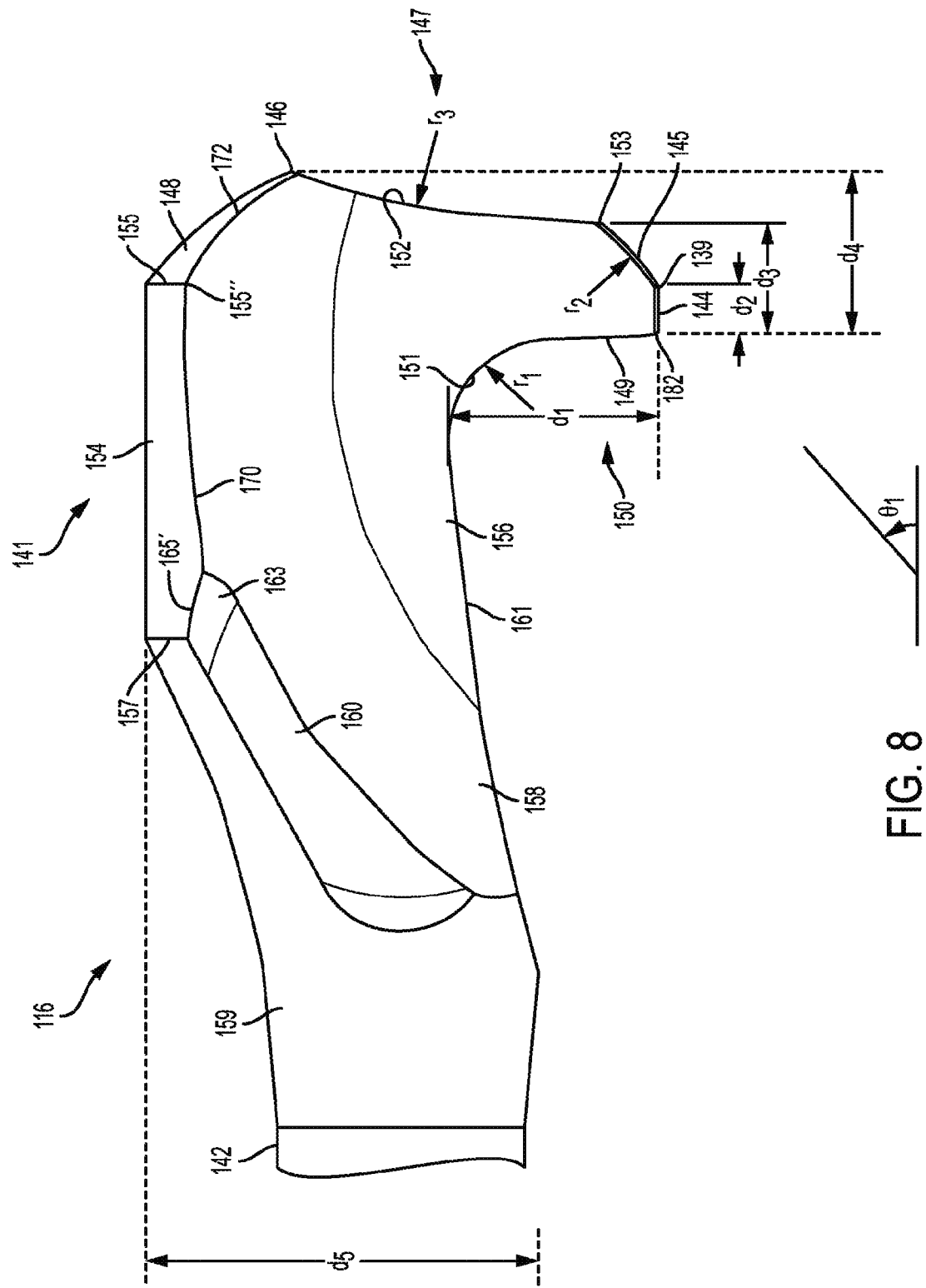
FIG. 8 is a side view of the ultrasonic surgical blade shown in FIG. 7, according to one embodiment.

FIG. 8 is a side view of the ultrasonic surgical blade 116 shown in FIG. 7, according to one embodiment. As described in connection with FIG. 7, the depth $d_1$ of the hook 150 is optimized to pull tissue. The dimension $d_1$ is the depth of the hook 150 from the upper tip 144 to the substantially planar longitudinal surface 161. The depth $d_1$ is approximately 2.4 mm and may vary between 1.8 mm to 3.0 mm, without departing from the scope of the present disclosure. A cutting edge 165 is defined by a surface inflection between the proximal hemostasis surface 154 and the cutting surface 163. The upper tip surface 144 defines a beveled edge 182. The upper tip 144 surface has a slight convexity.

The dimension $r_1$ is the radius of curvature of the curved surface 151 that joins the lower section of the flat inner surface 149 to the substantially planar longitudinal surface 161. The radius of curvature $r_1$ is approximately 0.823 mm and may vary between 0.635 mm to 1.010 mm, without departing from the scope of the present disclosure.

The dimension $d_2$ is the width of the upper surface 144 extending from the inner surface 149 to the juncture of the upper surface 144 and the oblique tip surface 145 may vary based on the particular configuration of this embodiment. The dimension $d_2$ is approximately 0.5075 mm and may vary from 0.38 mm to 0.635 mm, but the embodiment is not limited in this context.

The dimension $d_3$ is the distance from the planar inner surface 149 to the juncture of the oblique tip surface 145 and the distal surface 152. The juncture of the of the distal surface 152 is the minimum length of the distal surface 152, which flares out distally at a radius of curvature $r_3$ to the juncture with the dissection edged 146. The dimension of $d_3$ is approximately 1.08 mm and may vary between 0.89 mm to 1.27 mm, without departing from the scope of the present disclosure. The dimension of $r_3$ given the same centerline is approximately 8.57 mm and may vary between 8.38 mm to 8.76 mm, without departing from the scope of the present disclosure.

The dimension $r_2$ is the radius of curvature of the oblique tip surface 145, which has a convex curvature. The radius of curvature $r_2$ is approximately 2.985 mm and may vary between 2.8 mm to 3.17 mm, without departing from the scope of the present disclosure.

The distance from the juncture of the tip surface 144 and the oblique tip surface 145 defines the degree of obliqueness of the oblique tip surface 145. This dimension may vary depending on the particular configuration of this embodiment.

The length extending orthogonally from a point where the curved surface 151 meets the longitudinal flat surface 161 to a point on the distal surface 152 defines the base of the transverse portion 147. This dimension may vary depending on the particular configuration of this embodiment.

The dimension $d_4$ is the length from the juncture of the tip surface 144 and the planar inner surface 149 to the most distal point defined by the dissection edge 146. The dimension of $d_4$ is approximately 1.58 mm may vary between 1.39 mm to 1.77 mm, without departing from the scope of the present disclosure.

The length of the distal surface 152 extends from the juncture with the oblique tip surface 145 to the juncture of the distal surface 152 and the dissection edge 146 at a radius of curvature of $r_3$. This dimension may vary depending on the particular configuration of this embodiment. The radius of curvature of the distal hemostasis surface 148, may vary depending on the particular configuration of this embodiment.

The length of the longitudinal hemostasis surface 154 extends from the surface inflection 155 between the proximal hemostasis surface 148 and the distal hemostasis surface 154 and the surface inflection 157 between the distal hemostasis surface 154 and the blade body 159. This dimension may vary depending on the particular configuration of this embodiment.

The dimension $d_5$ is the distance from the longitudinal surface 154 to the surface inflection between the blade body 159 and the substantially planar longitudinal surface 161. The dimension of $d_5$ is approximately 4.375 mm and can vary from 3.75 mm to 5.00 mm, without departing from the scope of the present disclosure.

Figure 9:
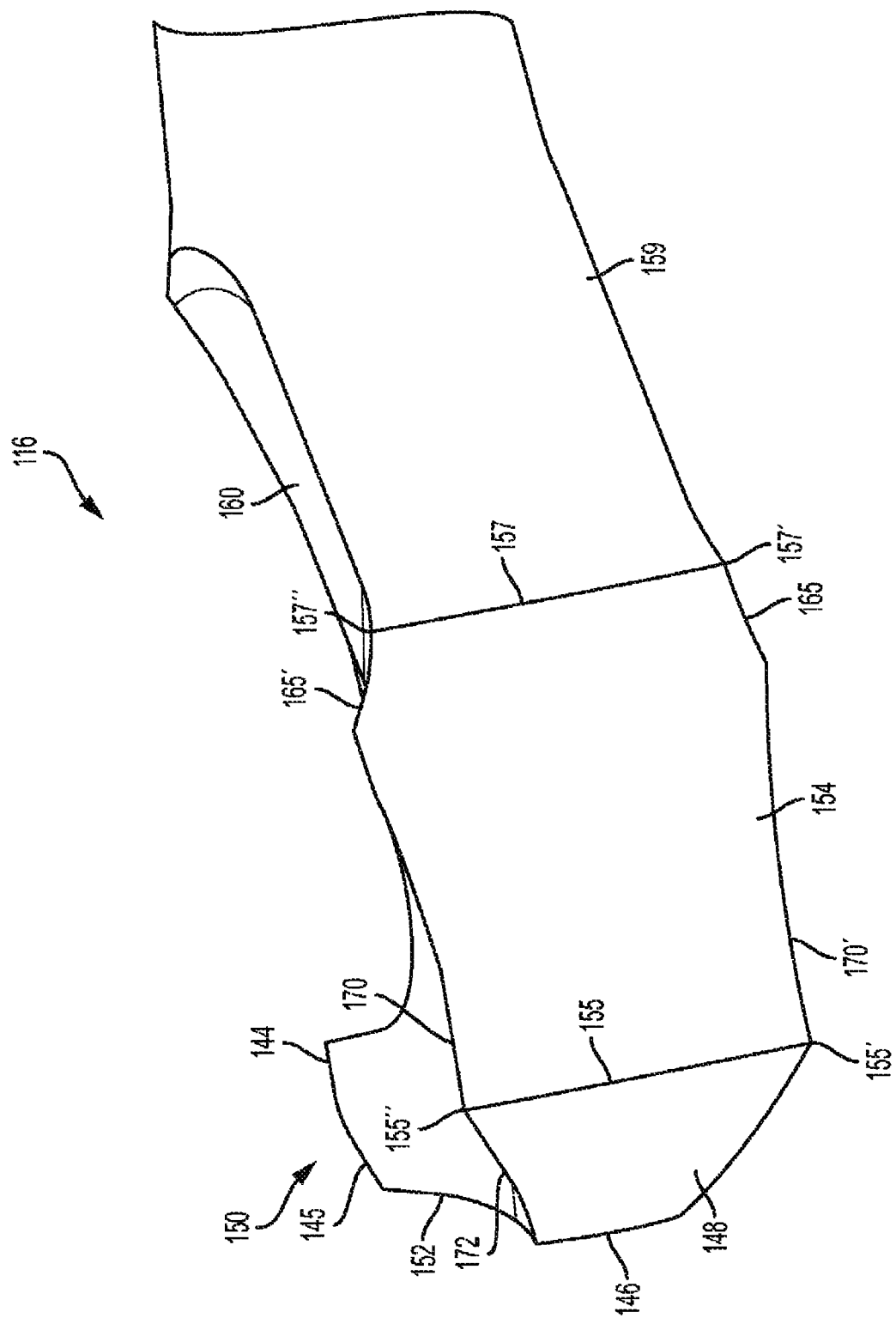
FIG. 9 is a perspective view of the ultrasonic surgical blade according to one embodiment.

FIG. 9 is a perspective view of the ultrasonic surgical blade 116 according to one embodiment. The view illustrated in FIG. 9 shows the width of the junctures 155, 157 of the distal and proximal hemostasis surfaces 148, 154, respectively, and the surface areas of each surface 148, 154. The sizes of the distal and proximal hemostasis surfaces 148, 154 are dimensioned to deliver suitable hemostasis while minimizing mass.

Figure 10:
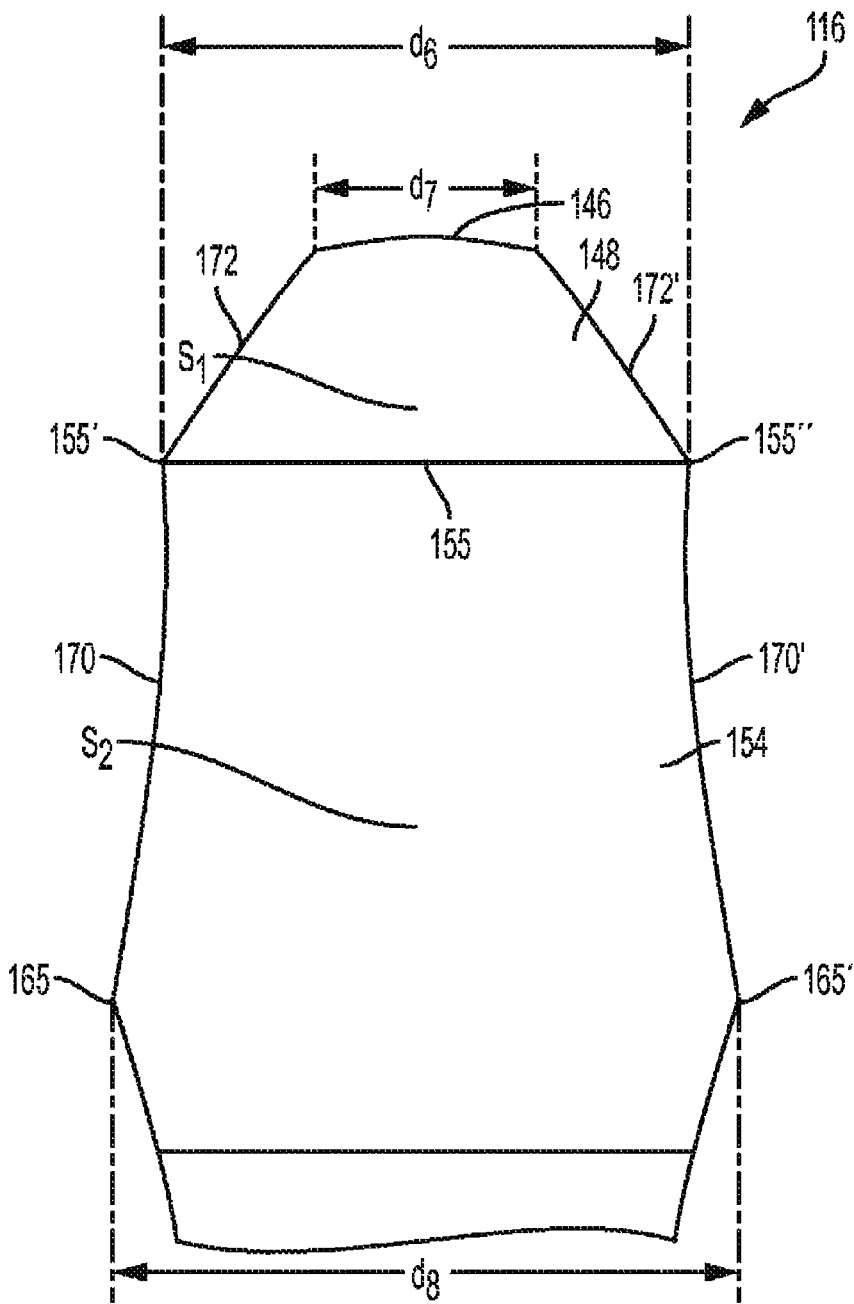
FIG. 10 is an illustration of the distal and proximal hemostasis surface of the ultrasonic surgical blade shown in FIGS. 7-9, according to one embodiment.

FIG. 10 is an illustration of the distal and proximal hemostasis surface 148, 154 of the ultrasonic surgical blade 116 shown in FIGS. 7-9, according to one embodiment. The distal hemostasis surface 148 defines a distal dissection edge 146 and lateral sharp cutting edges 172, 172'. The dimension $d_6$ is the maximum width of the distal hemostasis surface 148 and dimension $d_7$ is the minimum width of the distal hemostasis surface 148 and the minimum width of the proximal hemostasis surface 154. The dimension of $d_6$ may vary according to the particular configuration of this embodiment. The distal hemostasis surface 148 has an effective surface area 51 of approximately 4.838 mm² and may vary over a range of 3.226 mm² to 6.45 mm² (0.005 in² to 0.01 in²). The proximal hemostasis surface 154 defines lateral sharp cutting edges 170, 170'. The dimension $d_7$ is the minimum width of the proximal hemostasis surface 154. The dimension $d_8$ is the maximum width of the proximal hemostasis surface 154. The dimension of $d_8$ may vary according to the particular configuration of this embodiment. The proximal hemostasis surface 154 has an effective surface area S2 of approximately 9.675 mm² and may vary over a range of 6.45 mm² to 12.90 mm² (0.01 in² to 0.02 in²).

Figure 11:
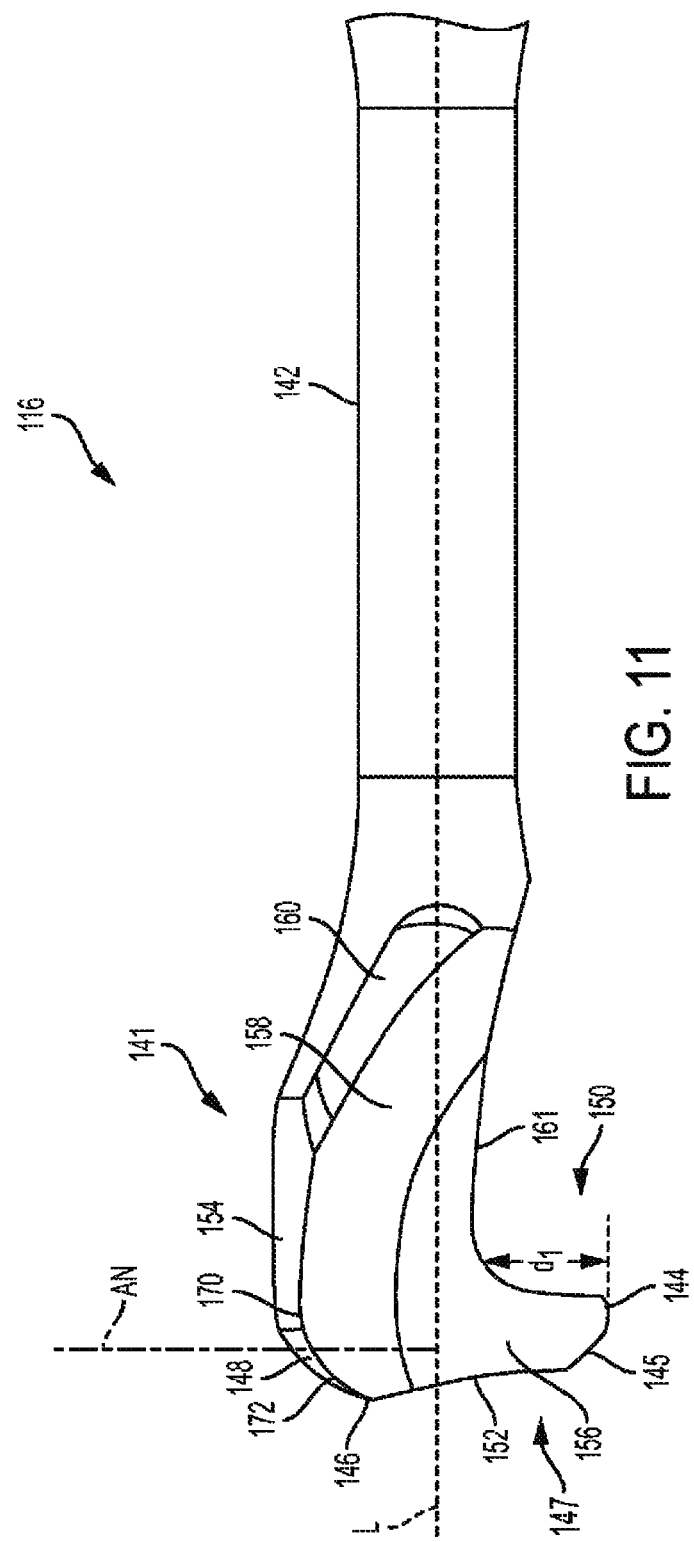
FIG. 11 is a side view of the ultrasonic surgical blade in a neutral position illustrating the location of the distal antinode AN and the longitudinal axis L, according to one embodiment.

FIG. 11 is a side view of the ultrasonic surgical blade 116 in a neutral position illustrating the location of the distal antinode AN and the longitudinal axis L, according to one embodiment. It is well known that a standing wave that set up in the ultrasonic waveguide defines nodes and antinodes, where the nodes represent regions of minimal or no displacement and the antinodes represent regions of maximum displacement. The nodes and antinodes occur periodically based on the driving frequency of approximately 55.5 kilohertz, for example. The nodes and antinodes are located at one quarter wavelength apart. Accordingly, the transverse portion 147 of the blade hook 150 is located at the antinode AN, thus is located at a point of maximum displacement.

Figure 12:
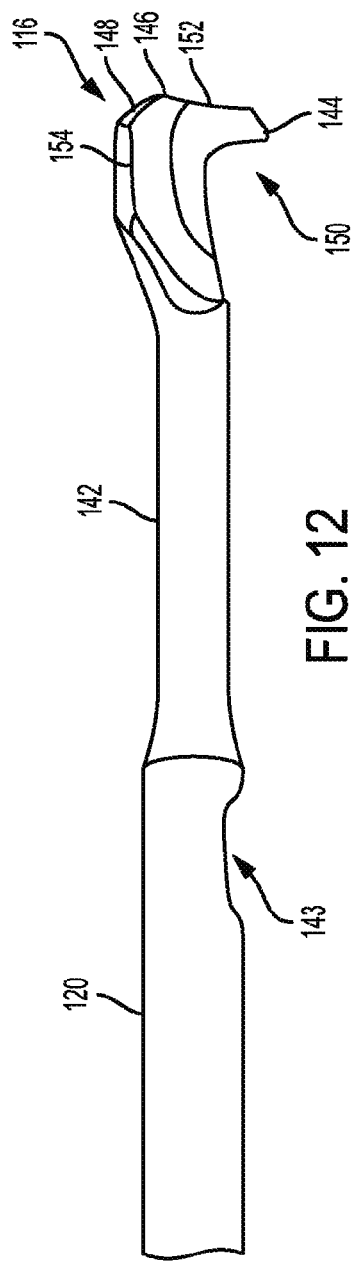
FIG. 12 is an illustration of the ultrasonic surgical blade shown in FIG. 11 in an intermediate position with no displacement.
Figure 13:
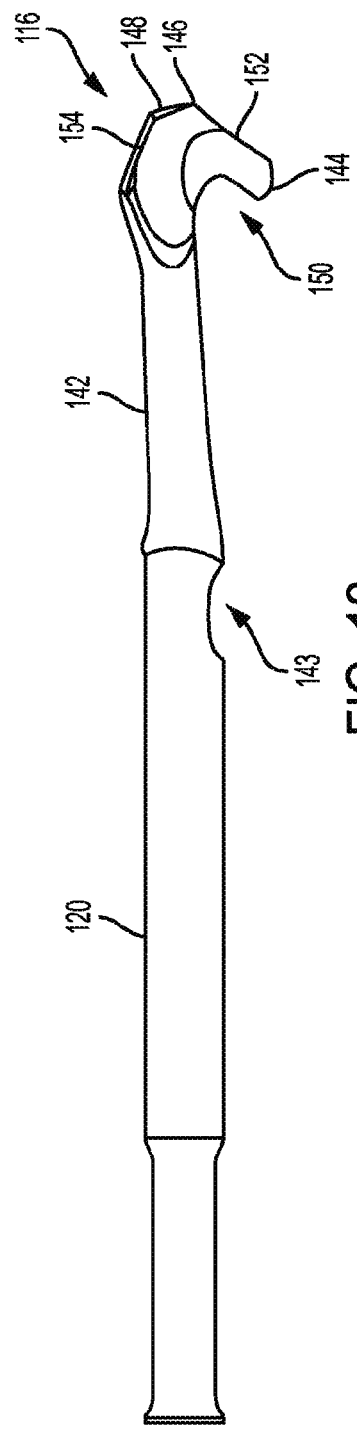
FIG. 13 is an illustration of the ultrasonic surgical blade shown in FIG. 11 in a maximum proximal displacement.
Figure 14:
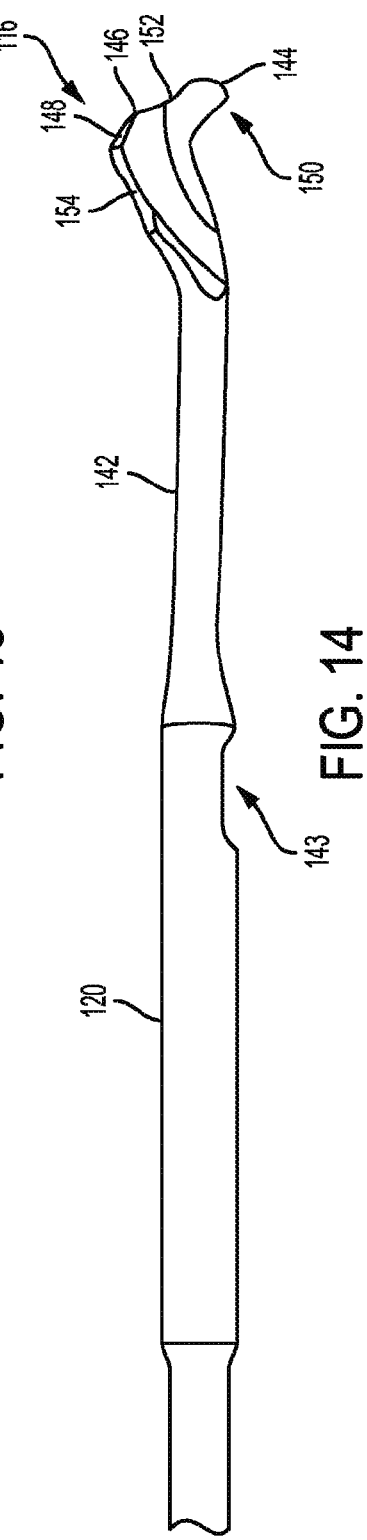
FIG. 14 is an illustration of the ultrasonic surgical blade shown in FIG. 11 in a maximum distal displacement.

FIGS. 12-14 illustrate the ultrasonic surgical blade 116 in three states of motions, where FIG. 12 is an illustration of the ultrasonic surgical blade 116 shown in FIG. 11 in an intermediate position with no displacement, FIG. 13 is an illustration of the ultrasonic surgical blade 116 shown in FIG. 11 in a maximum proximal displacement, and FIG. 14 is an illustration of the ultrasonic surgical blade 116. FIG. 11 in a maximum distal displacement. Accordingly, with reference to FIGS. 12-14, the ultrasonic surgical blade 116 moves between maximum and minimum displacement as the handle assembly 102 (FIG. 1) converts electrical energy into ultrasonic motion of ultrasonic transmission assembly 120 and the treatment region of the surgical ultrasonic surgical blade 116. The ultrasonic surgical blade 116 vibrates at an excursion magnitude of 20 micrometers to 150 micrometers, and at a frequency of approximately 55.5 kilohertz. As shown in FIGS. 13 and 14 the maximum displacement is represented by the tip surface 144 of the hook 150. Also, the balance feature 143 portion assists the ultrasonic transmission waveguide 120 to flex during the vibration process.

Figure 15:
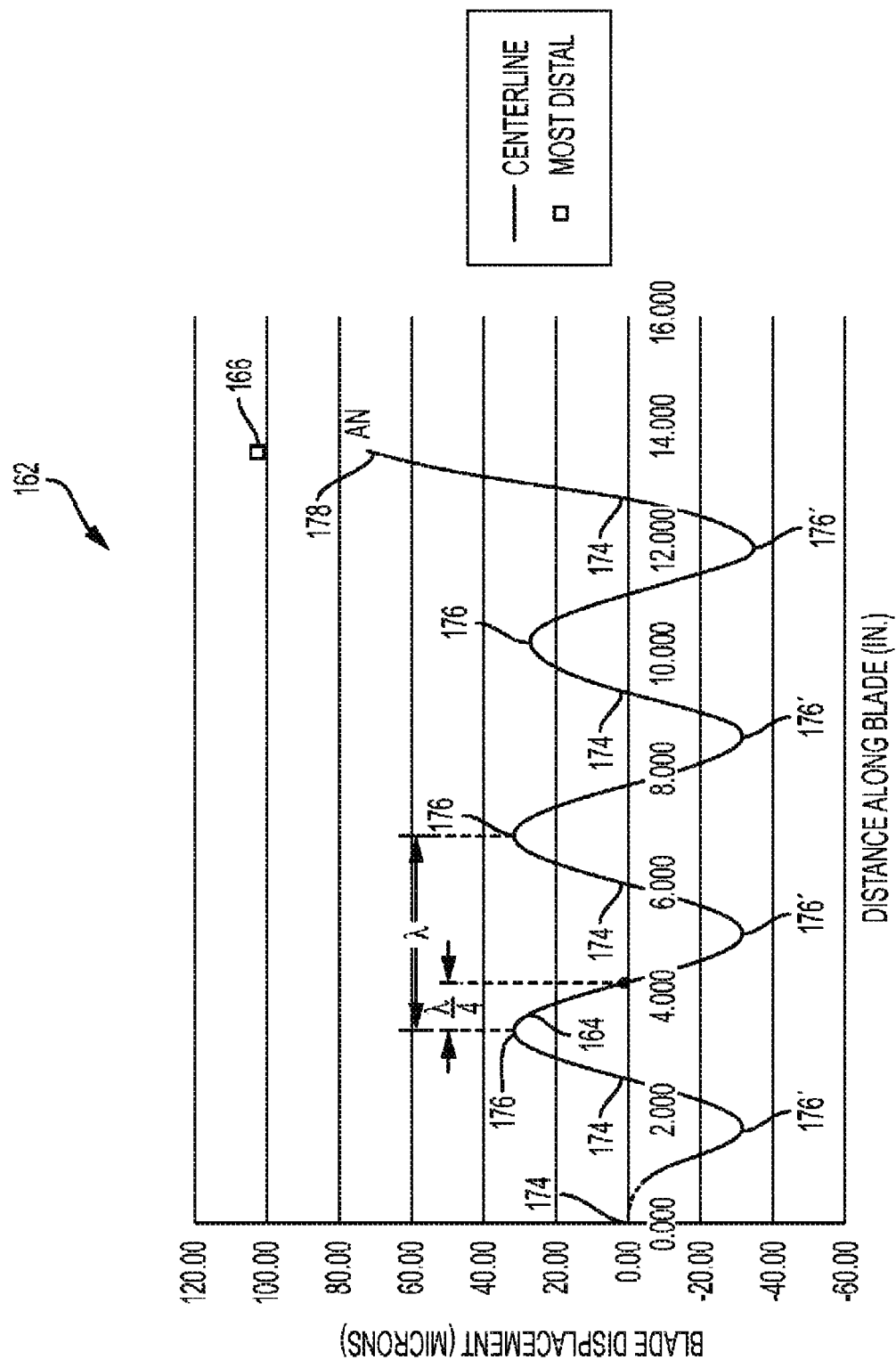
FIG. 15 is a graphical representation of displacement (microns) along the vertical axis of the ultrasonic surgical blade shown in FIGS. 12-14 versus distance (in) along the ultrasonic surgical blade along the horizontal axis, according to one embodiment.

FIG. 15 is a graphical representation of displacement (microns) along the vertical axis of the ultrasonic surgical blade 116 shown in FIGS. 12-14 versus distance (in) along the ultrasonic surgical blade 116 along the horizontal axis, according to one embodiment. The distance along the blade indicated as 0.000 in. corresponds to the most proximal location where the ultrasonic transmission waveguide 120 and the distance along the blade indicated as 14.000 in. corresponds to the most distal location where the ultrasonic tip 144 of the ultrasonic surgical blade 116 is displaced. With reference now also to FIG. 11, the blade displacement waveform 164 represented by the solid line is a standing waveform set up in the ultrasonic transmission waveguide and end effector ultrasonic surgical blade 116 along the longitudinal axil L as shown in FIG. 11. The displacement waveform 164 includes periodic nodes 174 and antinodes 176, 176' at locations along the longitudinal axis L. The nodes 174 are locations along the standing waveform 164 where there is no displacement and antinodes 176 are locations where displacement is maximum positive, and antinodes 176' where displacement is maximum negative. In accordance with the periodic nature of the ultrasonic vibrations and the properties of a standing wave 164, the nodes 174 and antinodes 176, 176' are located at a distance equal to one quarter wavelength λ/4, where the wavelength λ proportional to the frequency of vibrations $f_0$ and the speed c of sound in the material of the transmission waveguide and the ultrasonic surgical blade 116 according to the following relationship $f_0 = 2\pi\lambda/c$. Due to the design of the ultrasonic surgical blade 116, it can be seen that the absolute maximum displacement occurs at the distal antinode 178, which corresponds to the location of the antinode AN in FIG. 11.

Figure 16:
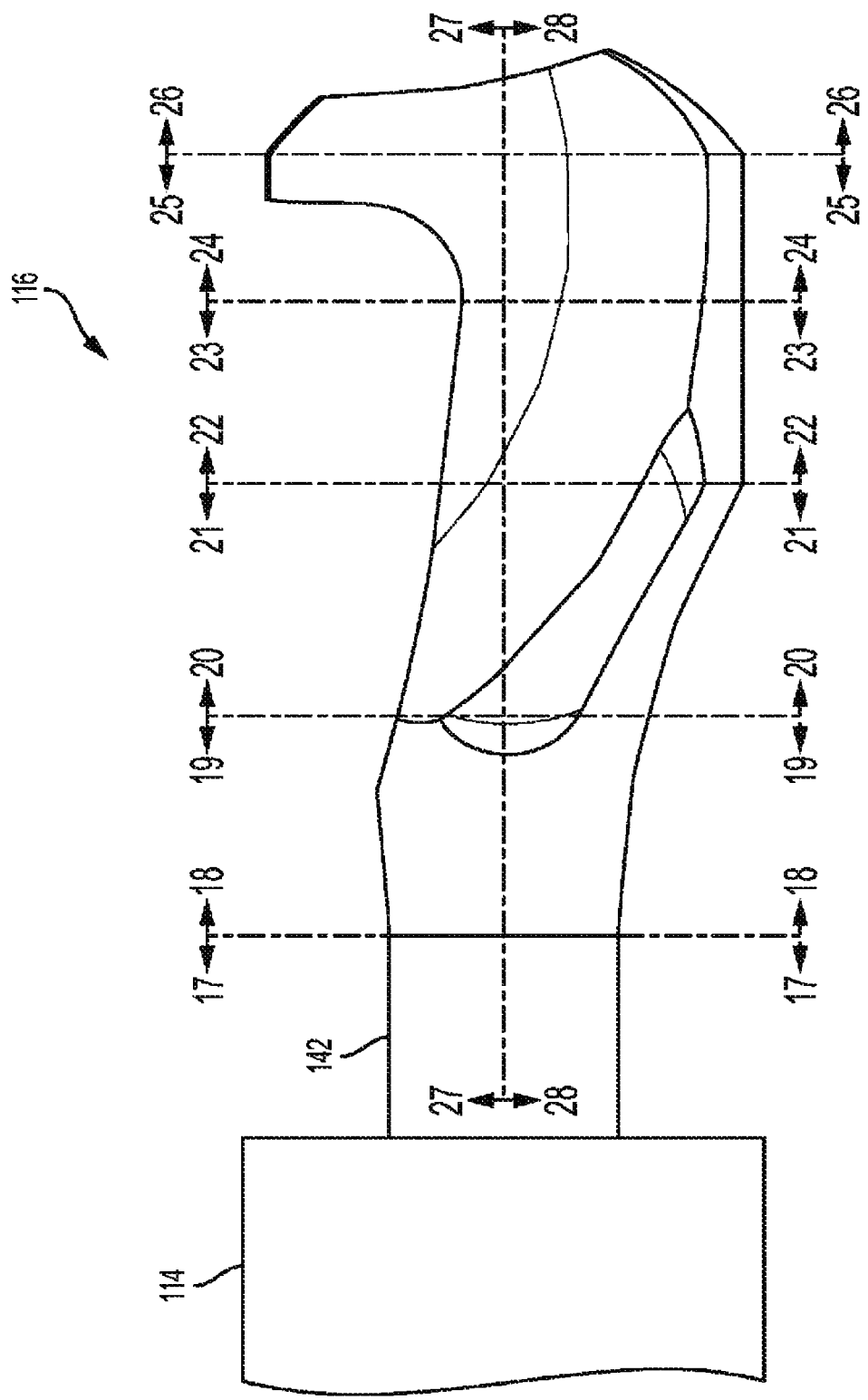
FIG. 16 is a side of the ultrasonic surgical blade shown in FIG. 7 illustrating the position of several sectional views shown in FIGS. 17-29, according to one embodiment.

FIG. 16 is a side of the ultrasonic surgical blade 116 shown in FIG. 7 illustrating the position of several sectional views shown in FIGS. 17-29, according to one embodiment.

FIG. 17 is a sectional view of the ultrasonic surgical blade 116 shown in FIG. 16 taken along section line 17-17, according to one embodiment. The sectional view shows the cross-section of the neck 142. The diameter of the neck 142 increases from an initial diameter $d_9$ to a final diameter $d_{10}$. The isolation spacer 118 is disposed about the proximal neck 142' portion of the neck 142 to isolate the ultrasonic surgical blade 116 from the outer sheath 114. The isolation spacer 118 is located at a node of the ultrasonic transmission waveguide. The outer diameter $d_{11}$ of the outer sheath 114 is sized to be slidably received within a trocar. The ultrasonic surgical blade 116 is sized to fit within the inner diameter $d_{12}$ of the outer sheath 114.

FIG. 18 is a sectional view of the ultrasonic surgical blade 116 shown in FIG. 16 taken along section line 18-18, according to one embodiment. As shown in the view of FIG. 18, the ultrasonic surgical blade 116 has an overall dimension to fit within the outer sheath 114. The junctures 157, 157' of the distal hemostasis surfaces 154, 154' and the cutting surface 163 section of the lateral surface 160 define din the blade body 159 define sharp edges that can be used to assist in dissection. The overall width $d_{16}$ of the ultrasonic surgical blade 116 is defined as the distance between the cutting edges 165, 165'. The lateral surface 160, 160' also are shown as straight surfaces in FIG. 18. The radius of curvature of the neck 142 is defined as $r_4$.

FIG. 19 is a sectional view of the ultrasonic surgical blade 116 shown in FIG. 16 taken along section line 19-19, according to one embodiment. As shown, the blade body 159 widens and defines flat sidewall portions of the lateral surfaces 160, 160'.

FIG. 20 is a sectional view of the ultrasonic surgical blade 116 shown in FIG. 16 taken along section line 20-20, according to one embodiment. The radius of curvature of the blade body 159 at section 20-20 is defined as $r_5$.

Figure 21:
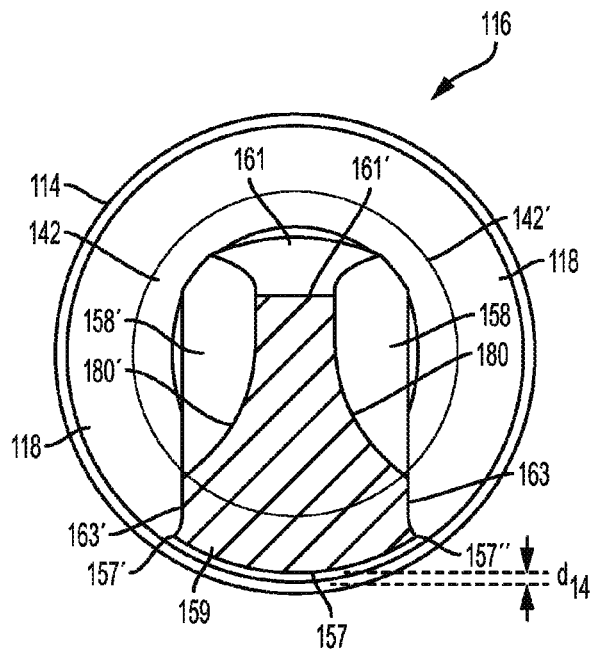
FIG. 21 is a sectional view of the ultrasonic surgical blade shown in FIG. 16 taken along section line 21-21, according to one embodiment.

FIG. 21 is a sectional view of the ultrasonic surgical blade 116 shown in FIG. 16 taken along section line 21-21, according to one embodiment. At section line 21-21, the cross sectional are of the blade body 159 is less than the cross sectional are shown in FIGS. 19 and 20. This is due to the lateral surfaces 158, 158' that are defined by the blade body 159 to balance the ultrasonic vibrations of the ultrasonic surgical blade 116. As shown, the lateral surfaces 158, 158' are contoured and define contoured lateral walls 180, 180' cut, ground, or otherwise formed in the blade body 159. Also, a gap $d_{14}$ is defined between the proximal hemostasis surface 154 and the inner diameter of the outer sheath 114. The gap $d_{14}$ enables the knife 116 to be slidably received and move within the outer sheath 114 as desired, and to fit within the diameter of a trocar. The flat portion 161' of the longitudinal surface 161 is also shown. The bottom surface 154 is the proximal hemostasis surface.

Figure 22:
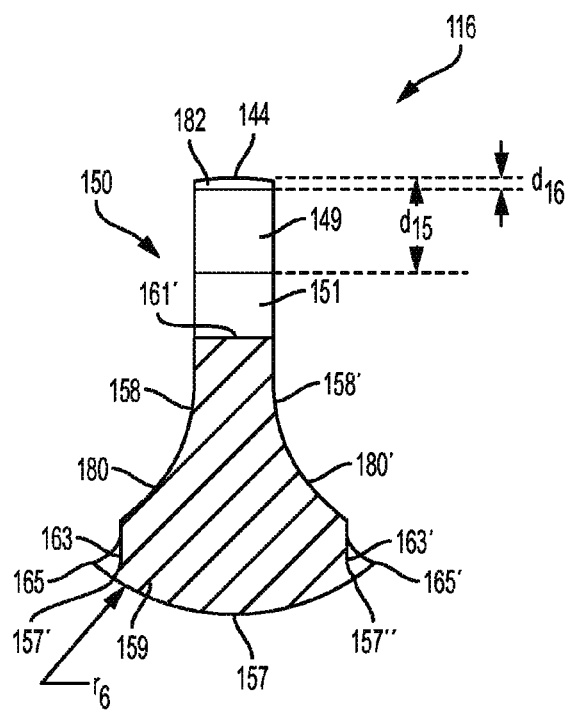
FIG. 22 is a sectional view of the ultrasonic surgical blade shown in FIG. 16 taken along section line 22-22, according to one embodiment.

FIG. 22 is a sectional view of the ultrasonic surgical blade 116 shown in FIG. 16 taken along section line 22-22, according to one embodiment. This sectional view illustrates the contoured lateral walls 180, 180' of the respective lateral surfaces 158, 158' defined in the blade body 159. This view also shows the cutting surfaces 163, 163' that extend from the contoured lateral walls 180, 180' of the respective lateral surfaces 158, 158'. This view also shows the length of the dimension $d_{15}$ of the planar inner surface 149 that extends from the tip surface 144 to the beginning of the curved surface 151 having a concave radius of curvature. This view also shows the dimension $d_{16}$ of the beveled edge 182 defined in the upper tip 144. The dimension of $d_{15}$ and the dimension of $d_{16}$ may vary according to the particular configuration of this embodiment. The flat dimension of the planar longitudinal surface 161 is also shown. The bottom surface 154 is the proximal hemostasis surface.

Figure 23:
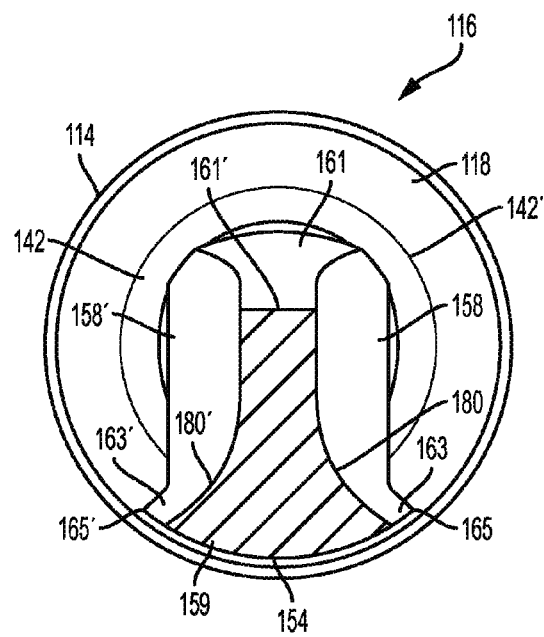
FIG. 23 is a sectional view of the ultrasonic surgical blade shown in FIG. 16 taken along section line 23-23, according to one embodiment.

FIG. 23 is a sectional view of the ultrasonic surgical blade 116 shown in FIG. 16 taken along section line 23-23, according to one embodiment. FIG. 23 shows the flat portion 161' of the longitudinal surface 161, the lateral surfaces 158, 158', and the contoured lateral walls 180, 180' of the lateral surfaces 158, 158'. The cutting surfaces 163, 163' flare out laterally from the blade body 159 to a surface inflection that defines cutting edges 165, 165'. The bottom surface 154 is the proximal hemostasis surface.

Figure 24:
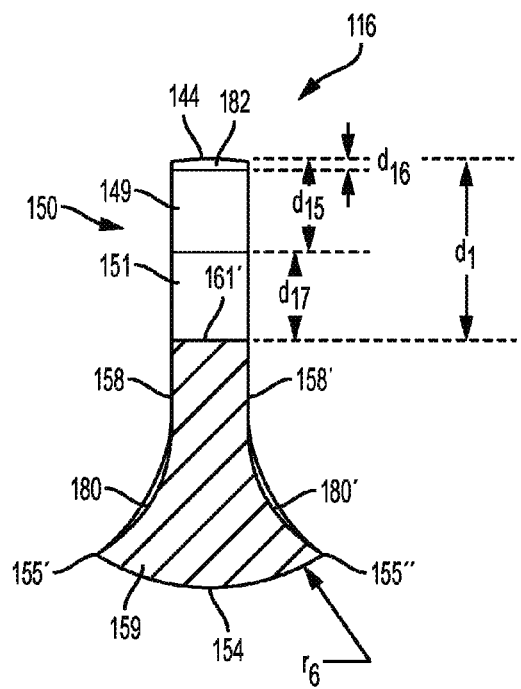
FIG. 24 is a sectional view of the ultrasonic surgical blade shown in FIG. 16 taken along section line 24-24, according to one embodiment.

FIG. 24 is a sectional view of the ultrasonic surgical blade 116 shown in FIG. 16 taken along section line 24-24, according to one embodiment. The section line 24-24 is taken to show the full dimension $d_{19}$ of the curved surface 151 portion of the blade hook 150. Also, shown is the full dimension $d_{15}$ of the inner surface 149 portion of the blade hook 150 as well as the dimension $d_{16}$ of the beveled edge 182 of the tip surface 144. This view also shows the flat portion 161' of the longitudinal surface 161, the straight lateral sidewalls of the blade hook 150 defined by the sidewalls of the beveled edge 182, the inner surface 149, and the curved surface 151. In this view, the dimension of the curved surface 151 is given by $d_{17}$. Extending below the flat portion 161' of the longitudinal surface 161 is the sectional view of the blade body 159 that defines the sidewalls of the lateral surfaces 158, 158' and the contoured lateral sidewalls 180, 180' of the lateral surfaces 158, 158' defined by the body 159. The bottom surface 154 is the proximal hemostasis surface. As previously discussed, the depth of the hook 150 is given by dimension $d_1$.

Figure 25:
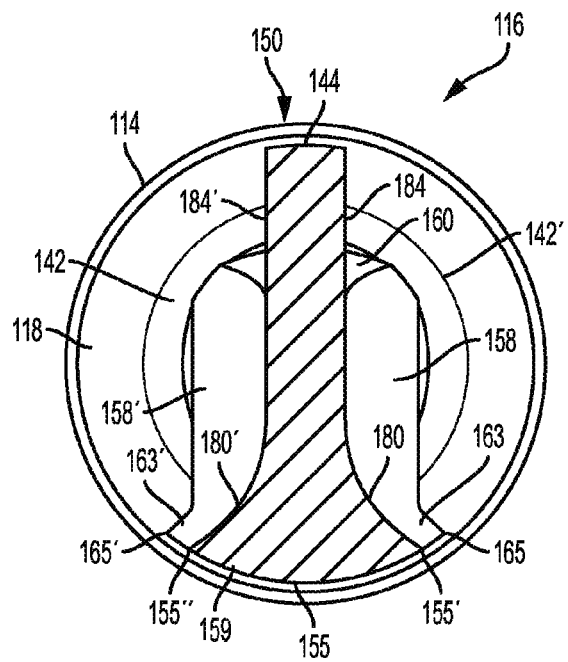
FIG. 25 is a sectional view of the ultrasonic surgical blade shown in FIG. 16 taken along section line 25-25, according to one embodiment.

FIG. 25 is a sectional view of the ultrasonic surgical blade 116 shown in FIG. 16 taken along section line 25-25, according to one embodiment. The section view 25-25 is taken at the transition between the tip surface 144 and the oblique tip surface 145. This view shows the full dimension of the ultrasonic surgical blade 116 located within the outer tube/sheath 114. The straight sidewalls 184, 184' of the blade hook 150 and the contoured lateral sidewalls 180, 180' of the lateral surfaces 158, 158' defined by the body 159. The contoured lateral sidewalls 180, 180' define the juncture 155 of the distal and proximal hemostasis surfaces 148, 154. Also shown is the distal hemostasis bottom surface 148 relative to the straight sidewall 184, 184' of the blade hook 150.

Figure 26:
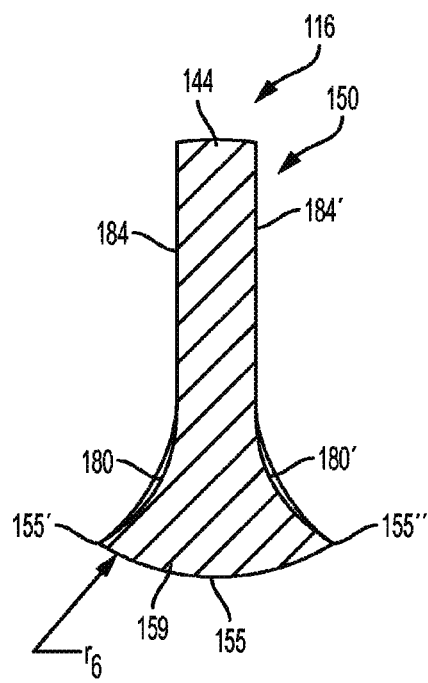
FIG. 26 is a sectional view of the ultrasonic surgical blade shown in FIG. 16 taken along section line 26-26, according to one embodiment.

FIG. 26 is a sectional view of the ultrasonic surgical blade 116 shown in FIG. 16 taken along section line 26-26, according to one embodiment. This view shows the straight sidewalls 184, 184' of the blade hook 150 which extends into the contoured lateral walls 180, 180' defined by the body 159. The contoured lateral walls 180, 180' define the juncture 155 of the distal and proximal hemostasis surfaces 148, 154. The distal hemostasis bottom surface 148 has a radius of curvature of $r_6$.

Figure 27:
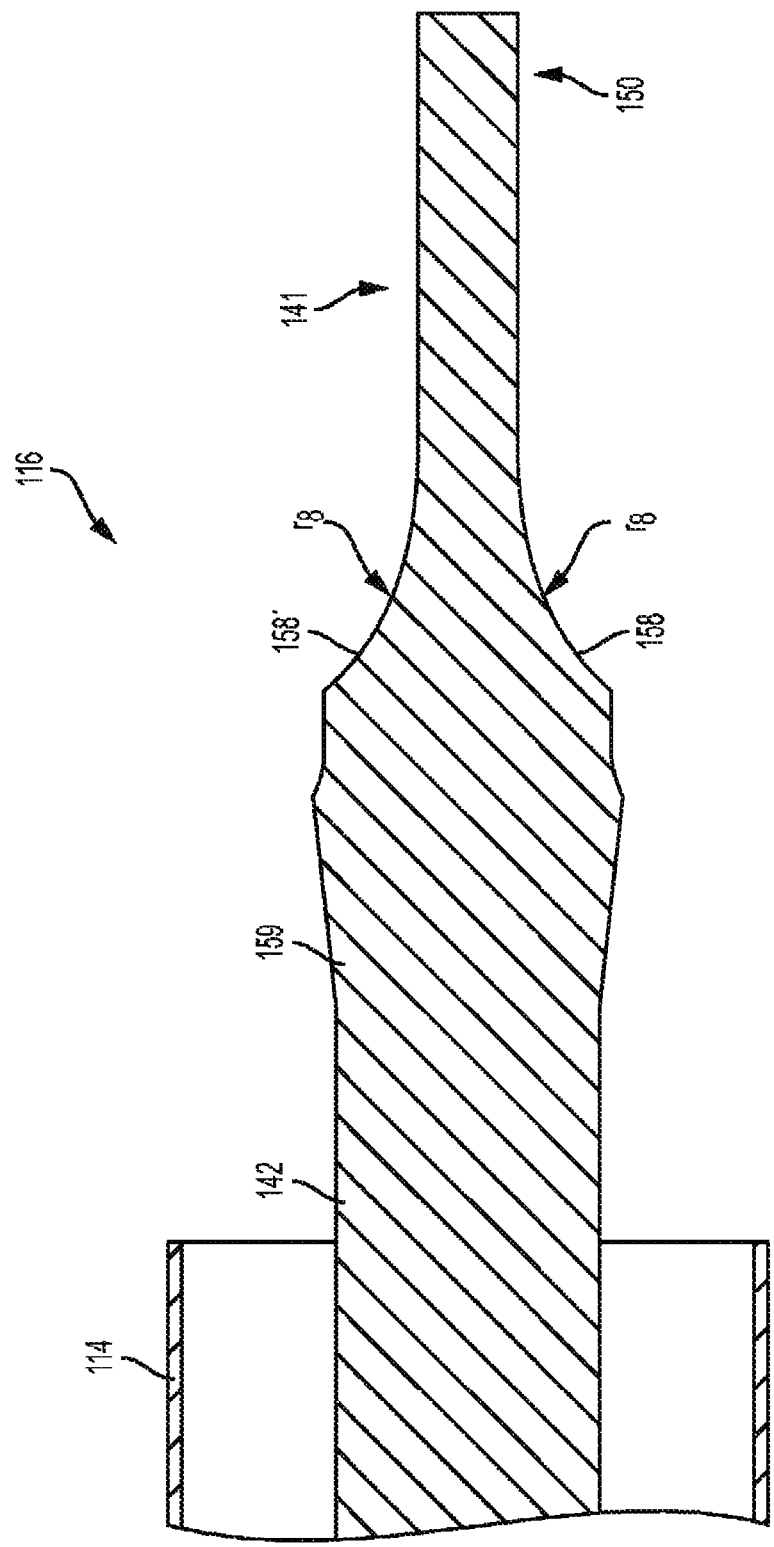
FIG. 27 is a sectional view of the ultrasonic surgical blade shown in FIG. 16 taken along section line 27-27, according to one embodiment.

FIG. 27 is a sectional view of the ultrasonic surgical blade 116 shown in FIG. 16 taken along section line 27-27, according to one embodiment. As illustrated in the sectional view shown in FIG. 27, the lateral surfaces 158, 158' have a radius of curvature of $r_8$. The radius of curvature of $r_8$ may vary according to the particular configuration of this embodiment. Also shown is the longitudinal extending portion 141 of the blade hook 150.

Figure 28:
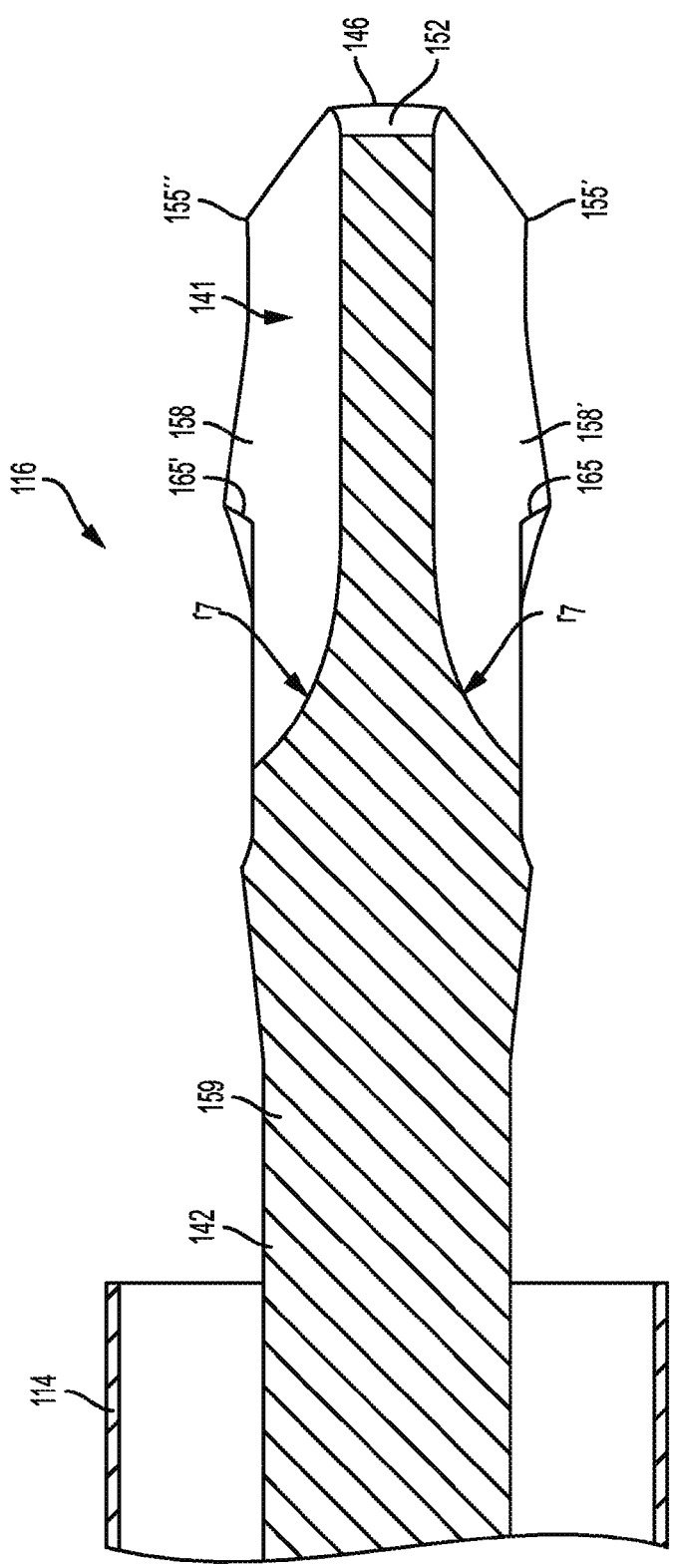
FIG. 28 is a sectional view of the ultrasonic surgical blade shown in FIG. 16 taken along section line 28-28, according to one embodiment.

FIG. 28 is a sectional view of the ultrasonic surgical blade 116 shown in FIG. 16 taken along section line 28-28, according to one embodiment. This view also shows the radius of curvature $r_7$ of the lateral surfaces 158, 158' and the cutting edges 165, 165' defined by the surface inflection between the proximal hemostasis surface 154 and the cutting surface 163 (FIG. 8).

Figure 29:
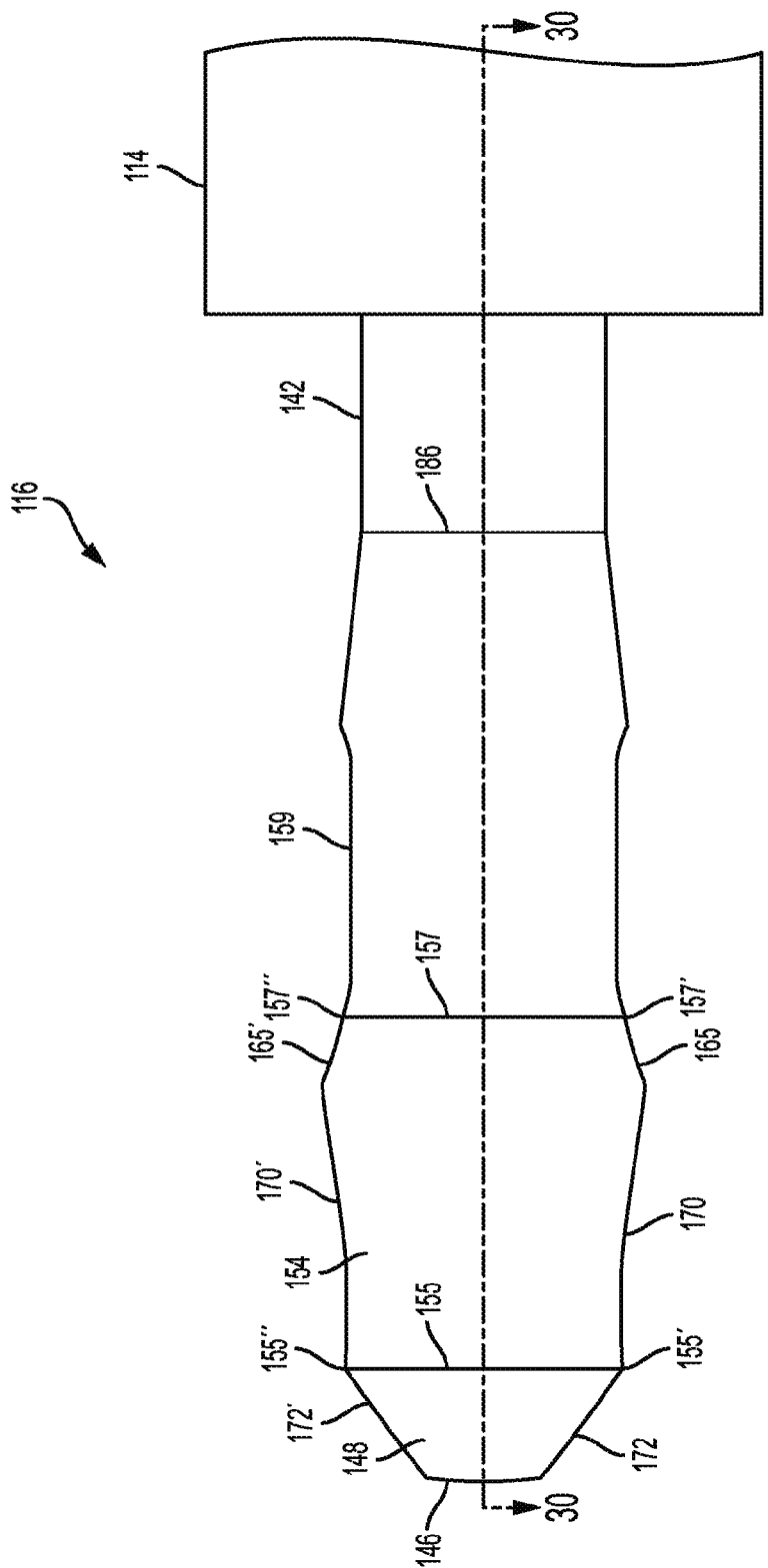
FIG. 29 is an illustration of a bottom view of the ultrasonic surgical blade shown in FIG. 7 showing the distal and proximal hemostasis surfaces and lateral cutting edges.

FIGS. 29-32 provide additional views of the ultrasonic surgical blade 116 shown in FIG. 7, according to one embodiment. FIG. 29 is an illustration of a bottom view of the ultrasonic surgical blade 116 shown in FIG. 7 showing the distal and proximal hemostasis surfaces 148, 154 and lateral cutting edges 172, 172", 170, 170'. This view also shows the edges 155', 155" defined by the surface inflection 155 between the distal and proximal hemostasis surfaces 148, 154. The most distal portion of the distal hemostasis surface 148 defines the dissection edge 146, which is defined as the surface inflection between the distal hemostasis surface 148 and the distal surface 152 (FIG. 8). Another surface inflection 157 between the proximal hemostasis surface 154 and the blade body 159 defines edges 157', 157" from which the cutting edges 165, 165' extend until they meet the lateral cutting edges 170, 170'. The blade body 159 transitions to the ultrasonic transmission waveguide 142 through surface loft 186. For completeness, the ultrasonic transmission waveguide 142 is shown extending proximally into the outer tube/sheath 114.

Figure 30:
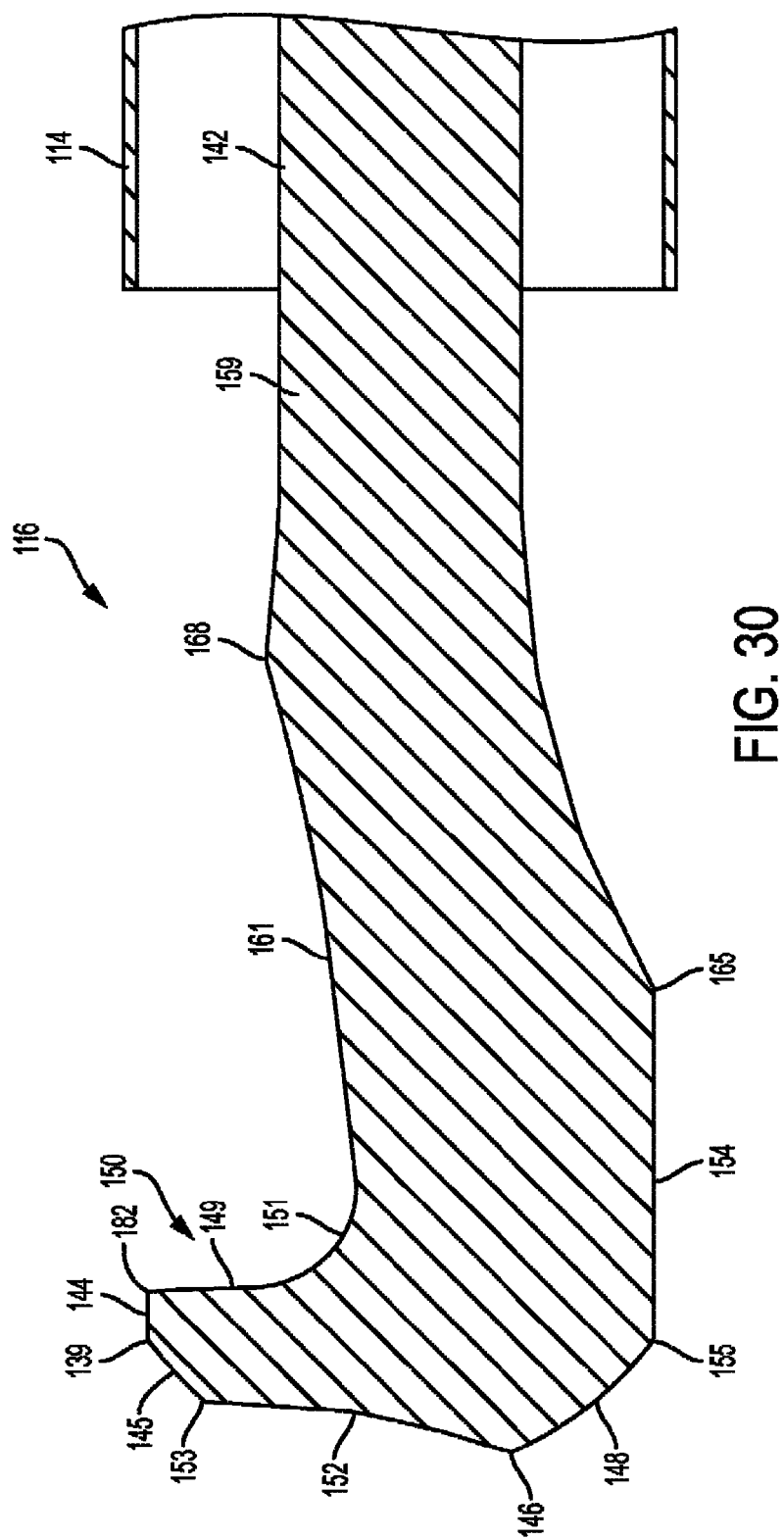
FIG. 30 is a sectional view of the ultrasonic surgical blade shown in FIG. 29 taken along section line 30-30, according to one embodiment.

FIG. 30 is a sectional view of the ultrasonic surgical blade 116 shown in FIG. 29 taken along section line 30-30, according to one embodiment. This sectional view is taken along the longitudinal centerline to show the relevant features of the ultrasonic surgical blade 116 previously described. From right to left, as the blade body 159 extends from the blade neck 142, the ultrasonic surgical blade 116 defines a first surface inflection 168 between the blade body 159 and the planar longitudinal surface 161. The hook portion 150 is defined in part by the curved surface 151 and the inner surface 149 up to the beveled surface 182. The tip surface 144 transitions to the oblique tip surface 145 at surface inflection 139. The oblique tip surface 145 transitions to the distal surface 152 at surface inflection 153 and the distal surface 152 transitions to the distal hemostasis surface 148 at surface inflection 146, which also defines the dissection edge 146. For purposes of the present disclosure, the surface inflection 146 and the dissection edge 146 refer to the same elements. The distal hemostasis surface 148 transitions to the proximal hemostasis surface 154 at surface inflection 155. Moving to the right from there, the proximal hemostasis surface 154 transitions to the blade body 159 at surface inflection 165.

Figure 31:
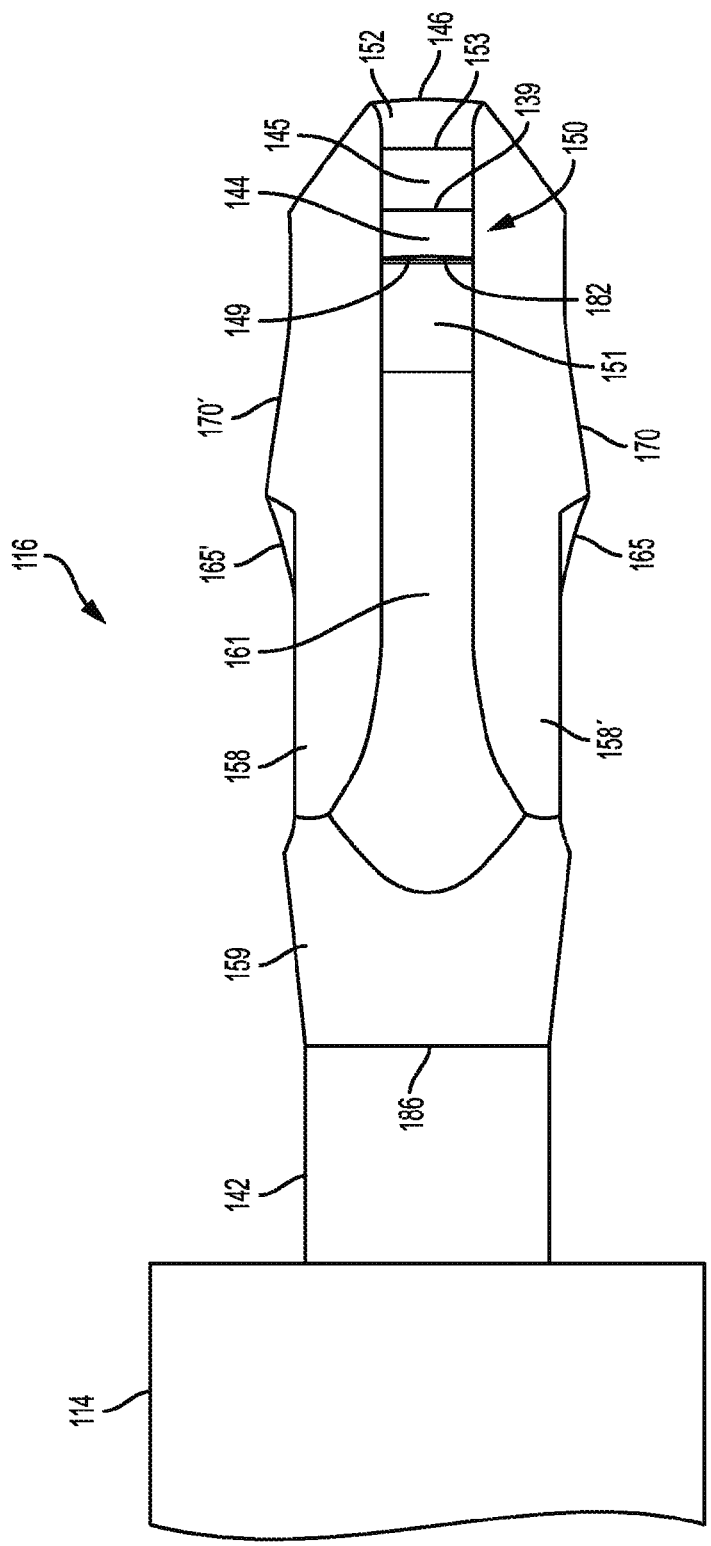
FIG. 31 is a top view of the ultrasonic surgical blade shown in FIG. 29, according to one embodiment.

FIG. 31 is a top view of the ultrasonic surgical blade 116 shown in FIG. 29, according to one embodiment. The top view of FIG. 31 is the opposite of the bottom view of FIG. 29. From left to right, the ultrasonic transmission waveguide 142 extends distally from the outer tube/sheath 114 and transitions into the blade body 159 portion at surface inflection 186. The blade body 159 defines several surfaces for cutting and/or pulling tissue, applying hemostasis to the tissue, and/or acoustically balancing the ultrasonic surgical blade 116. The planar longitudinal surface 161 extends from a proximal end of the blade body 159 to the curved surface 151 of the blade hook 150. The inner surface 149 of the blade hook 150 extends from the curved surface 151 to the beveled surface 182 of the tip surface 144. The tip surface 144 transitions to the oblique tip surface 145 at surface inflection 139. The oblique tip surface 145 transitions to the distal surface 152 at surface inflection 153. The most distal portion of the distal surface 152 defines the dissection edge 146, which is also the surface inflection between the distal surface 152 and the distal hemostasis surface 148 (FIG. 29). The top view of FIG. 31 also shows the lateral surfaces 158, 158' and the cutting edges 165, 165' defined by the surface inflection between the proximal hemostasis surface 154 and the lateral surfaces 160, 160'. The cutting edges 170, 170' are defined by the surface inflection of the proximal hemostasis surface 154 and the lateral surfaces 158, 158'.

Figure 32:
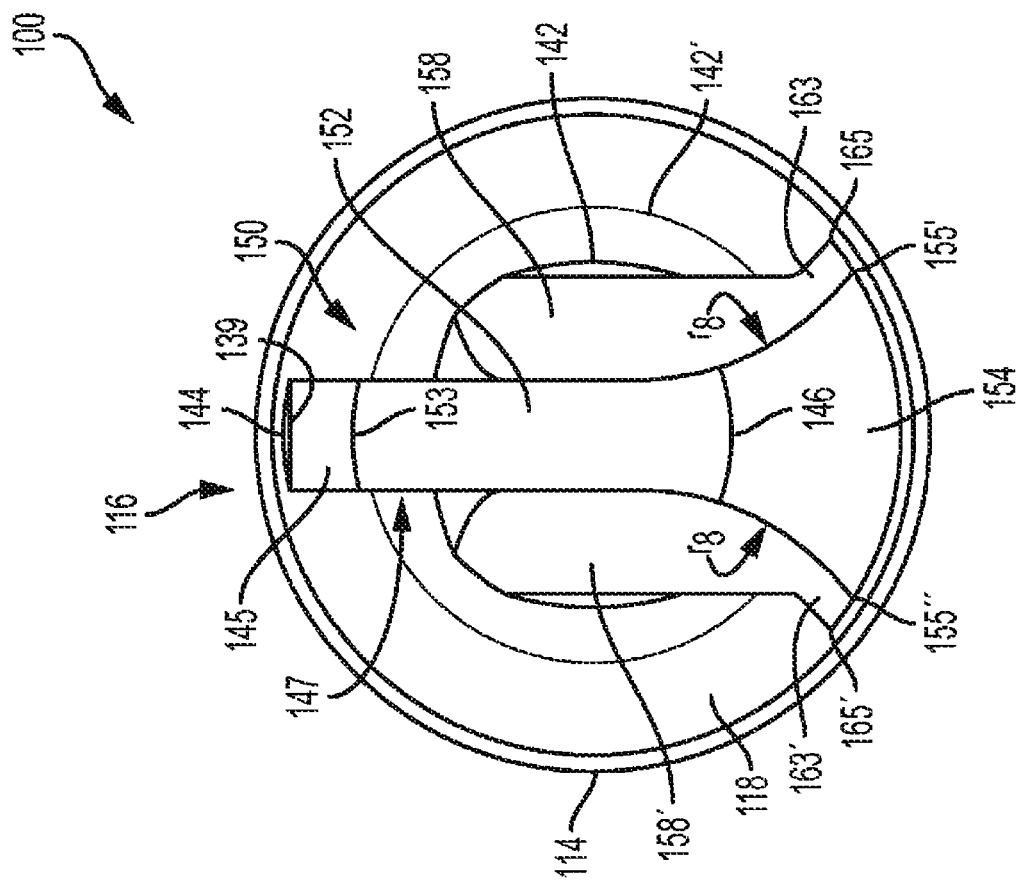
FIG. 32 is an end view of the ultrasonic surgical instrument showing the ultrasonic surgical blade and the outer tube/sheath, according to one embodiment.

FIG. 32 is an end view of the ultrasonic surgical instrument 100 showing the ultrasonic surgical blade 116 and the outer tube/sheath 114, according to one embodiment. As shown, the transverse portion 147 of the ultrasonic surgical blade 116 comprises a tip surface 144 that transitions into an oblique tip surface 145 at surface inflection 139. The distal surface 152 extends from the oblique tip surface 145 at surface inflection 153. The distal surface 152 defines the dissection edge 146 between the distal hemostasis surface 154 and the distal surface 152. The lateral surfaces 158, 158' extend proximally from the blade hook 150 and the walls define a radius of curvature $r_8$ on each side. The cutting edges 155', 155" are defined by the surface inflection 155 between the distal and proximal hemostasis surfaces 148, 154. The cutting edges 165. 165' are defined by the surface inflection between the proximal hemostasis surface 154 and the lateral surfaces 160, 160'. The lateral surfaces 160, 160' also define cutting surface 163, 163'. The ultrasonic surgical blade 116 extends distally from the outer tube/sheath 114. The isolation spacer 118 isolates the ultrasonic surgical blade 116 from the outer tube/sheath 114. The isolation spacer 118 is disposed about the proximal neck 142' portion of the ultrasonic surgical blade 116.

Ultrasonic Blade for Tissue Dissection and Hemostasis (Embodiment 2)

FIGS. 33-38 illustrate one embodiment of an ultrasonic surgical blade 200 configured with edges and surfaces to optimize hemostasis and dissection. In one use, the distal portion allows access to the surface of tissue, such as the liver bed, for efficient hemostasis. Sharp edges disposed on the distal portion of the ultrasonic surgical blade 200 deliver quick dissection. Accordingly, the disclosed ultrasonic blade 200 enables efficient dissection of the gall bladder from the liver bed using proximal and distal surfaces for ease of surgeon technique.

Figure 33:
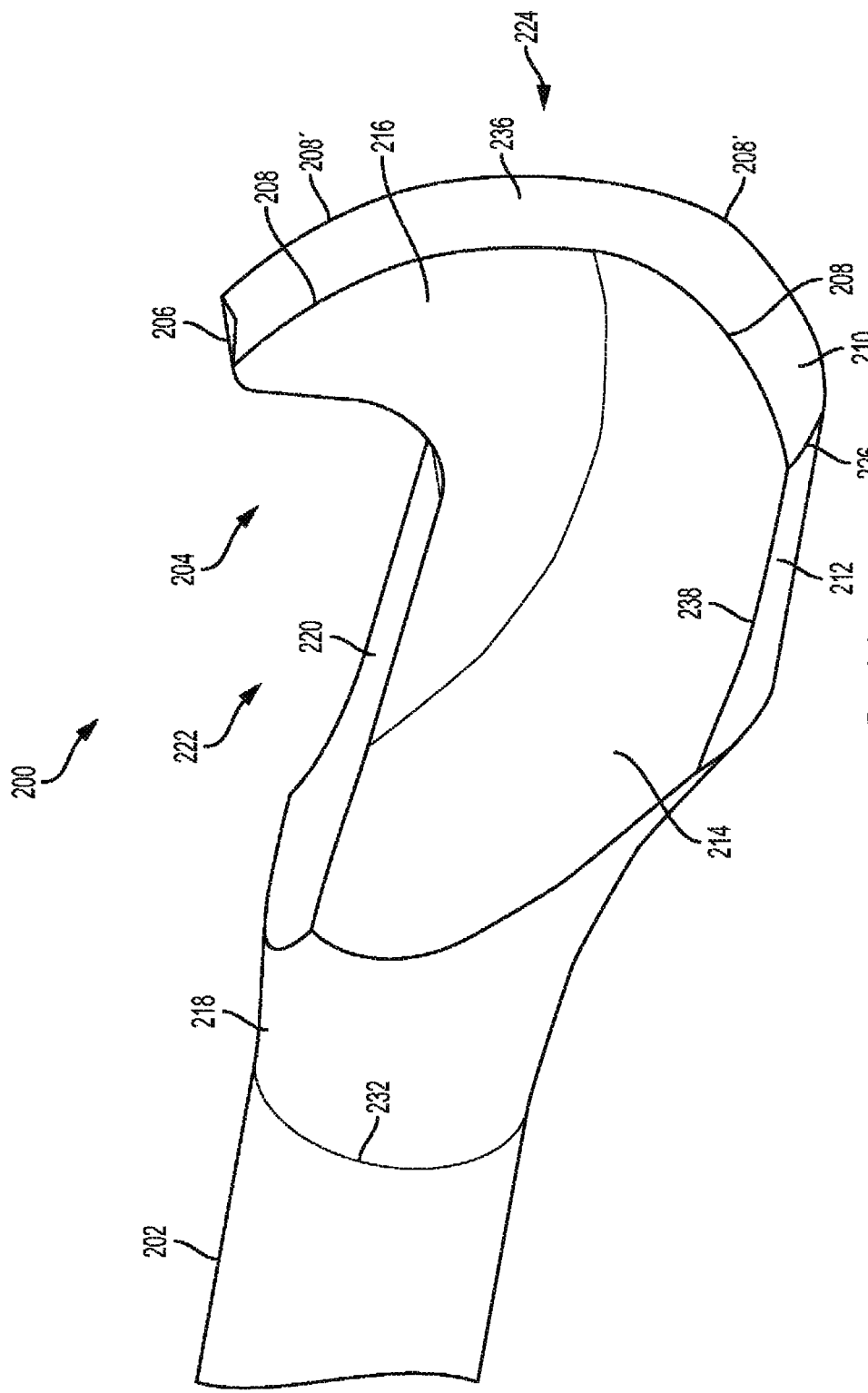
FIG. 33 is perspective view of the ultrasonic surgical blade, according to one embodiment.
Figure 34:
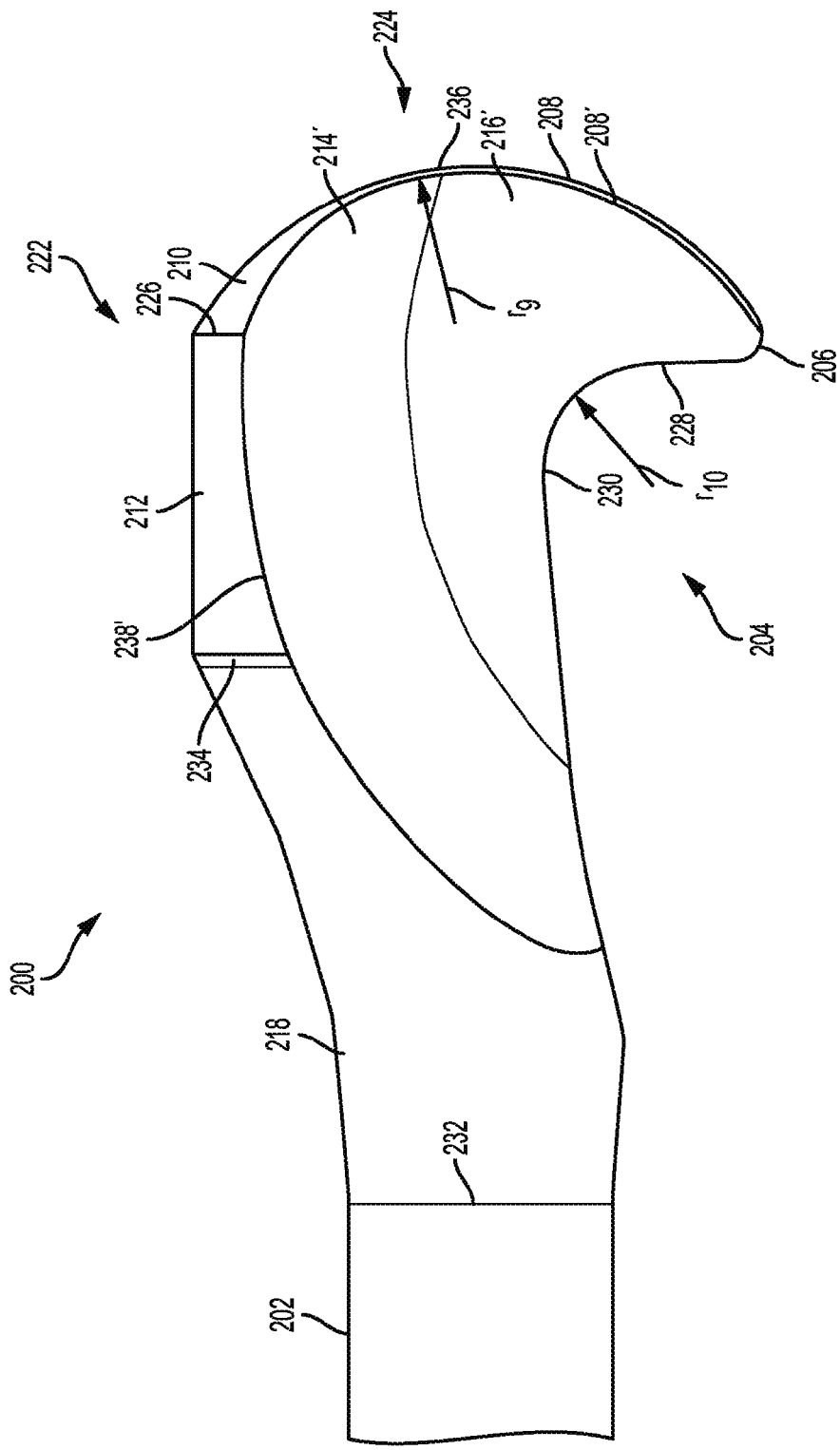
FIG. 34 is a side view of the ultrasonic surgical blade shown in FIG. 33, according to one embodiment.
Figure 35:
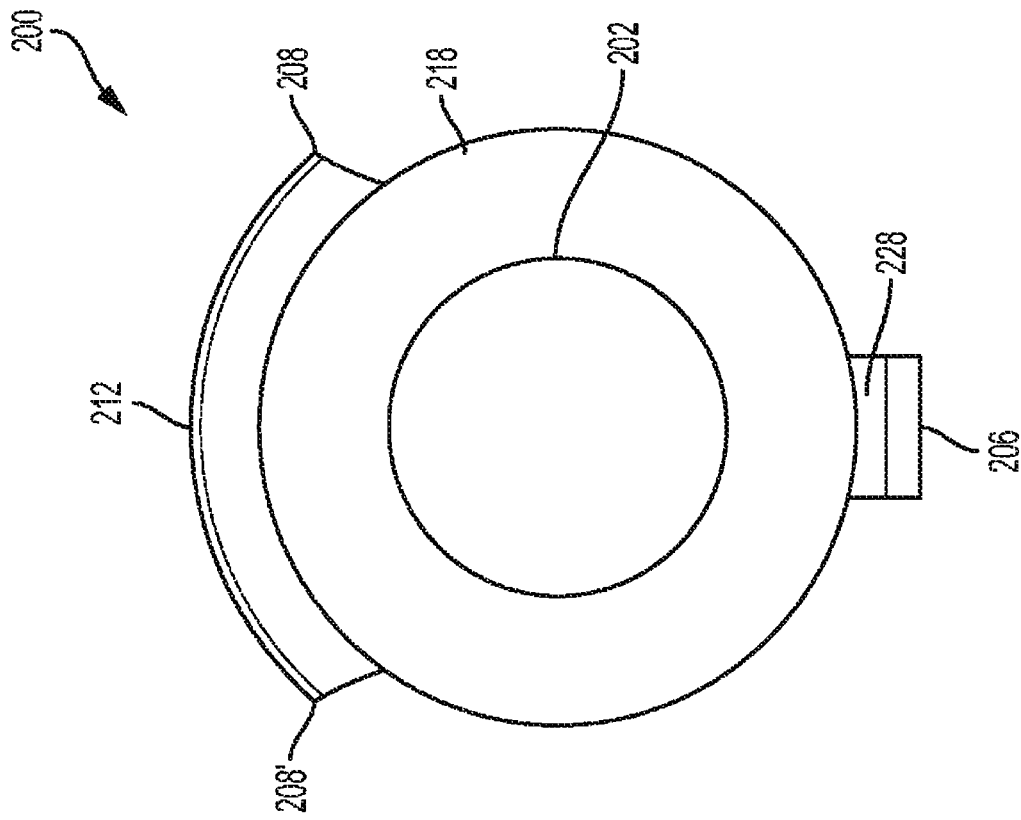
FIG. 35 is an end view of the ultrasonic surgical blade shown in FIG. 33, according to one embodiment.
Figure 36:
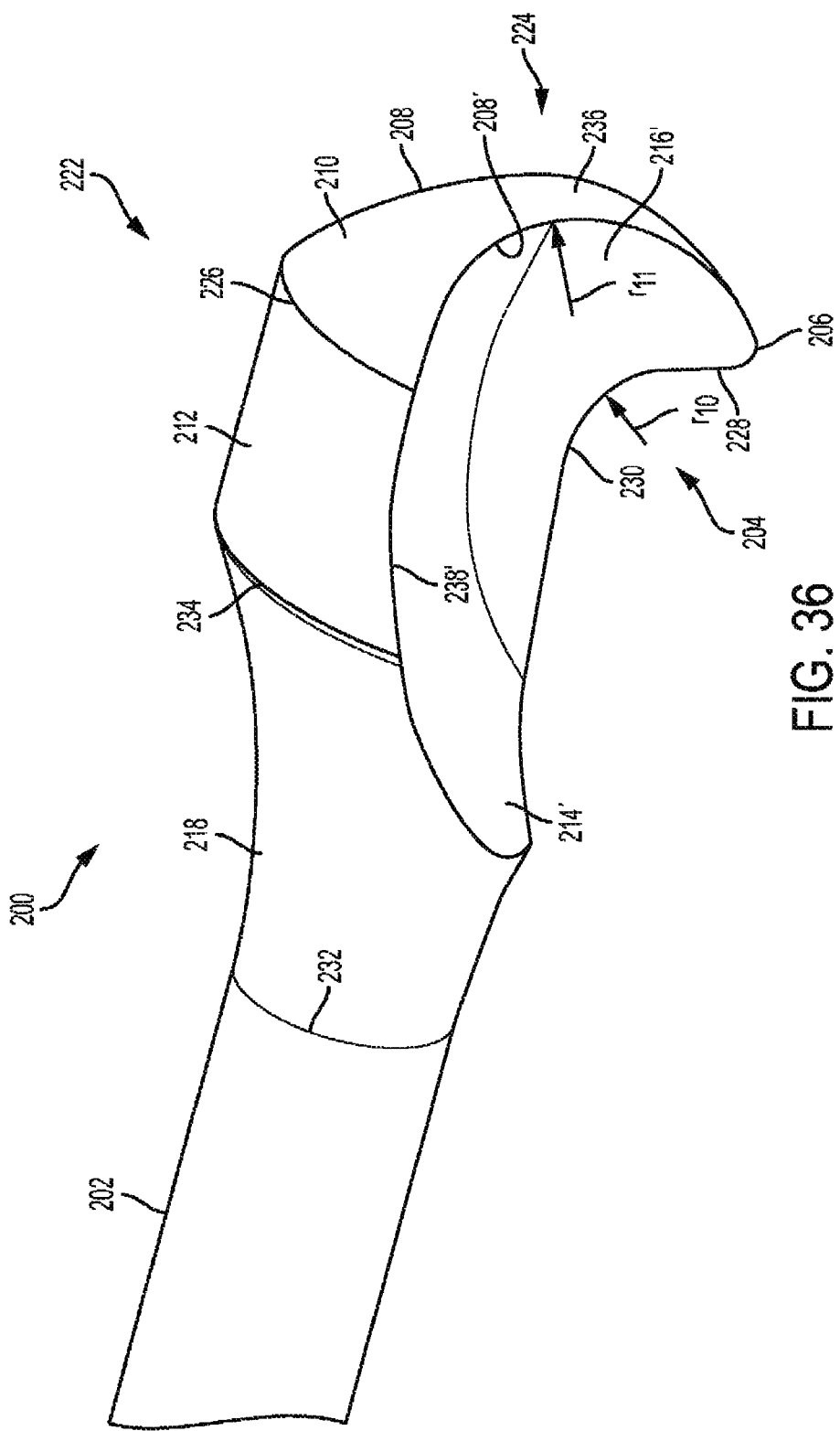
FIG. 36 is another perspective view of the ultrasonic surgical blade shown in FIG. 33, according to one embodiment.
Figure 37:
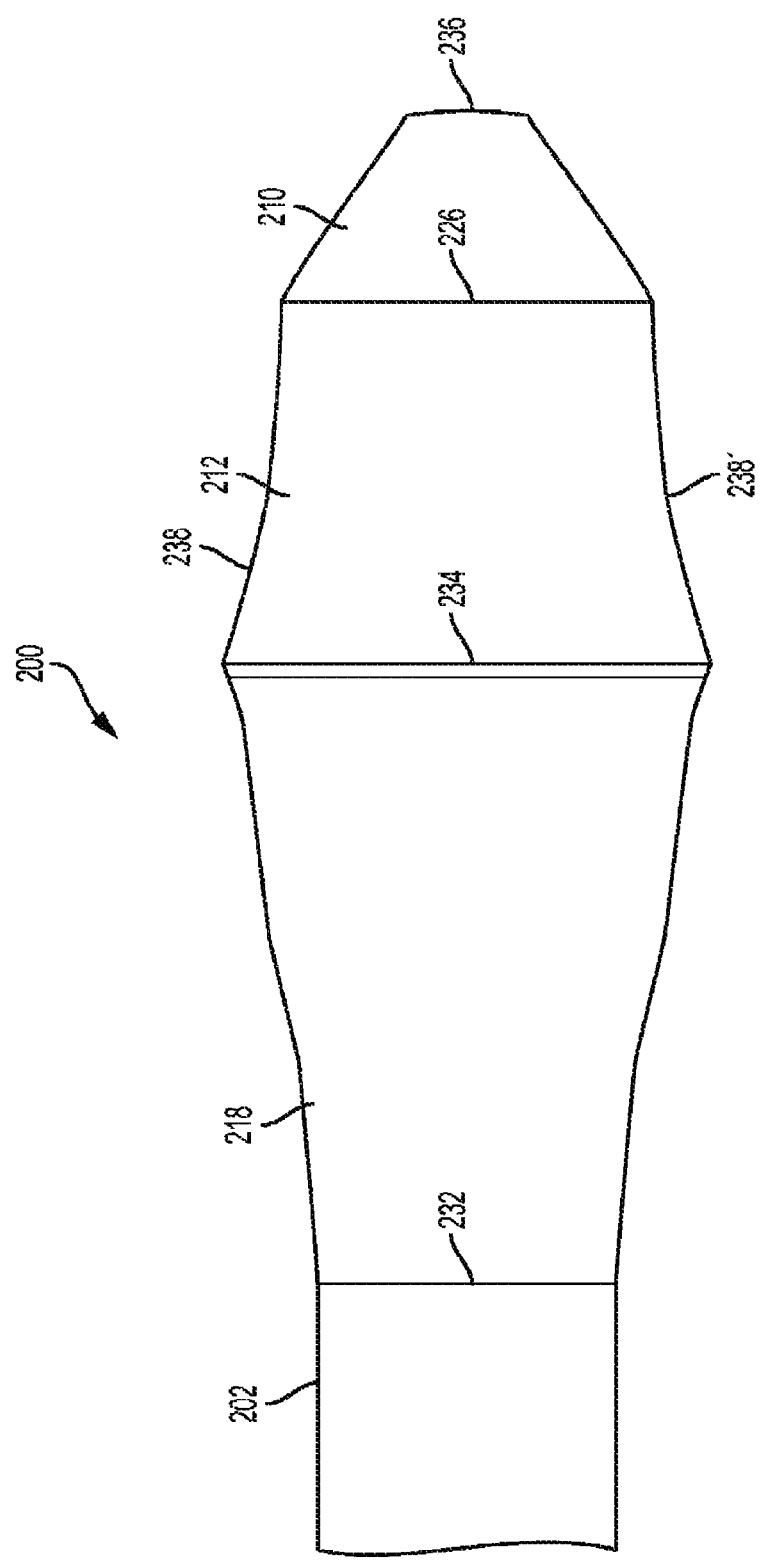
FIG. 37 is a bottom view of the ultrasonic surgical blade shown in FIG. 33, according to one embodiment.

FIG. 33 is perspective view of the ultrasonic surgical blade 200, according to one embodiment. FIG. 34 is a side view of the ultrasonic surgical blade 200 shown in FIG. 33, according to one embodiment. FIG. 35 is an end view of the ultrasonic surgical blade 200 shown in FIG. 33, according to one embodiment. FIG. 36 is another perspective view of the ultrasonic surgical blade 200 shown in FIG. 33, according to one embodiment. FIG. 37 is a bottom view of the ultrasonic surgical blade 200 shown in FIG. 33, according to one embodiment.

With reference now to FIGS. 33-38, in one embodiment, the ultrasonic surgical blade 200 is configured and adapted to operate with the ultrasonic surgical instrument 100 shown and described connection with FIGS. 1-5. Accordingly, the ultrasonic surgical blade 200 comprises a blade body 218 that transitions into a blade neck 202 at surface inflection 232. The blade neck 202 extends proximally to form or couple to an ultrasonic transmission waveguide, having a proximal end configured to acoustically couple to an ultrasonic transducer piezoelectric stack. In the distal direction, the blade body 218 defines several surfaces suitable for cutting and/or pulling tissue, applying hemostasis to the tissue, and/or acoustically balancing the ultrasonic surgical blade 200.

Still with reference to FIGS. 33-38, the ultrasonic surgical blade 200 comprises a longitudinal portion 222 and a transverse portion 224. The longitudinal portion 222 extends distally from the blade body 218 and defines a substantially planar longitudinal surface 220 and multiple lateral surfaces 214, 216 are defined on each lateral portion of the blade body 218. The lateral surfaces 214, 214' extend from the substantially planar longitudinal surface 220 to a proximal hemostasis surface 212 and define sharp cutting edges 238, 238'. A portion of the lateral surfaces 214, 214' extend to the distal hemostasis surface 210 and define sharp cutting edges 208, 208'. The sharp cutting edges 208, 208', 238, 238' aid in fast dissection when using the side of the ultrasonic blade 200 and the distal surface 236. The lateral surfaces 216, 216' extend from the substantially planar longitudinal surface 220 and the transverse hook portion 204 of the ultrasonic surgical blade 200 to the distal surface 236 to define portions of the sharp cutting edges 208, 208'. The sharp cutting edges 208, 208" have a radius of curvature $r_9$ that may vary between 2.45 to 2.75 mm, without departing from the scope of the disclosure.

Still with reference to FIGS. 33-38, the transverse portion 224 of the ultrasonic surgical blade 200 defines the blade hook 204, which is suitable for pulling and cutting tissue and may be configured to access the tissue plane between the gull bladder and the liver. The blade hook 204 comprise a curved surface 230 having a radius of curvature $r_{10}$ extending from the substantially planar longitudinal surface 220 to the inner surface 228. The radius of curvature $r_{10}$ may vary between 0.635 mm to 1.010 mm, without departing from the scope of the disclosure. The inner surface 228 extends to a tip surface 206. The tip surface 206 extends towards the distal surface 236, which extends to the distal hemostasis surface 210. The distal hemostasis surface 210 defines a larger surface area on the bottom and distal side of the ultrasonic surgical blade 200 to aid hemostasis. The distal hemostasis surface 210 transitions to the proximal hemostasis surface 212 at surface inflection 226. The proximal hemostasis surface 212 transitions into the body portion 218 of the ultrasonic surgical blade 200 at surface inflection 234. The blade body 218 eventually transitions into the blade neck 202 at surface inflection 232. Other dimensions of the ultrasonic surgical blade 200 may be similar to the dimensions of the ultrasonic surgical blade 116 shown and described in connection with FIGS. 6-32, although the embodiments are not limited in this context.

Figure 38:
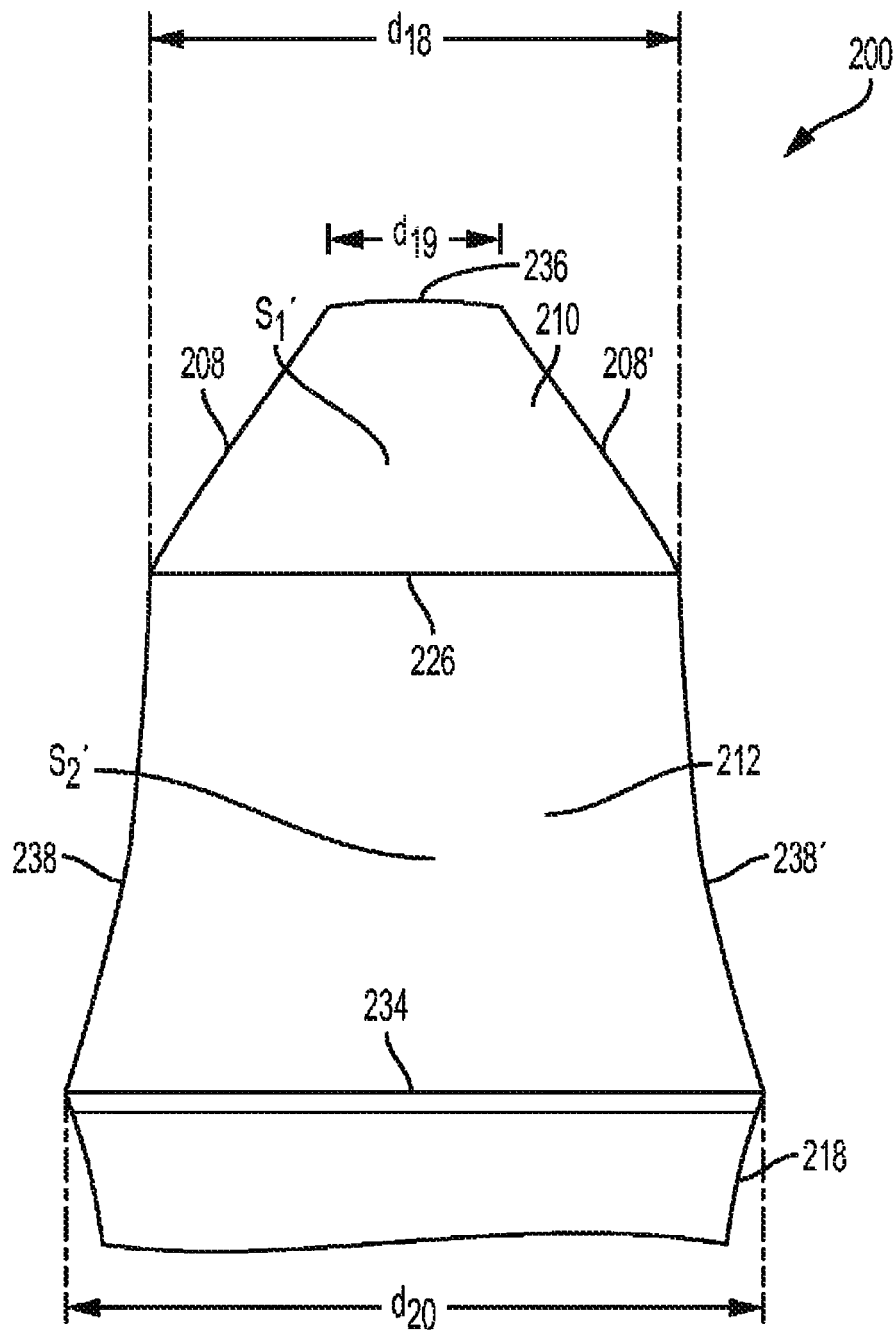
FIG. 38 is an illustration of the distal and proximal hemostasis surface of the ultrasonic surgical blade shown in FIGS. 33-37, according to one embodiment.

FIG. 38 is an illustration of the distal and proximal hemostasis surface 210, 212 of the ultrasonic surgical blade 200 shown in FIGS. 33-37, according to one embodiment. The distal hemostasis surface 210 is continuous with the distal surface 236 and transitions to the proximal hemostasis surface 212 at surface inflection 226. The proximal hemostasis surface 212 transitions into the body portion 218 of the ultrasonic surgical blade 200 at surface inflection 234. The distal hemostasis surface 210 and the proximal hemostasis surface define a surface inflection 226 therebetween. The distal hemostasis surface 210 defines sharp cutting edges 208, 208'. The dimension $d_{18}$ is the maximum width of the distal hemostasis surface 236 and dimension $d_{19}$ is the minimum width of the distal hemostasis surface 212 and the minimum width of the proximal hemostasis surface 210. The dimension of $d_{19}$ may vary according to the particular configuration of this embodiment. The dimension $d_{19}$ is the minimum width of the proximal hemostasis surface 210. The dimension $d_{20}$ is the maximum width of the proximal hemostasis surface 212. The dimension of $d_{20}$ may vary according to the particular configuration of this embodiment. The distal hemostasis surface 210 has an effective surface area S1' of approximately 54.1935 mm$^2$ and may vary over a range of 3.226 mm$^2$ to 105.161 mm$^2$ (0.005 in$^2$ to 0.163 in$^2$). The proximal hemostasis surface 212 defines sharp cutting edges 238, 238'. The proximal hemostasis surface 212 has an effective surface area S2' of approximately 9.6765 mm$^2$ and may vary over a range of 6.45 mm$^2$ to 12.903 mm$^2$ (0.01 in$^2$ to 0.02 in$^2$).

Ultrasonic Blade for Tissue Dissection and Hemostasis (Embodiment 3)

FIGS. 39-52 illustrate one embodiment of an ultrasonic surgical blade 300 configured with edges and surfaces to optimize hemostasis and dissection. In one use, the distal portion allows access to the surface of tissue, such as the liver bed, for efficient hemostasis. Sharp edges disposed on the distal portion of the ultrasonic surgical blade 300 deliver quick dissection. Accordingly, the disclosed ultrasonic blade 300 enables efficient dissection of the gall bladder from the liver bed using proximal and distal surfaces for ease of surgeon technique.

Figure 39:
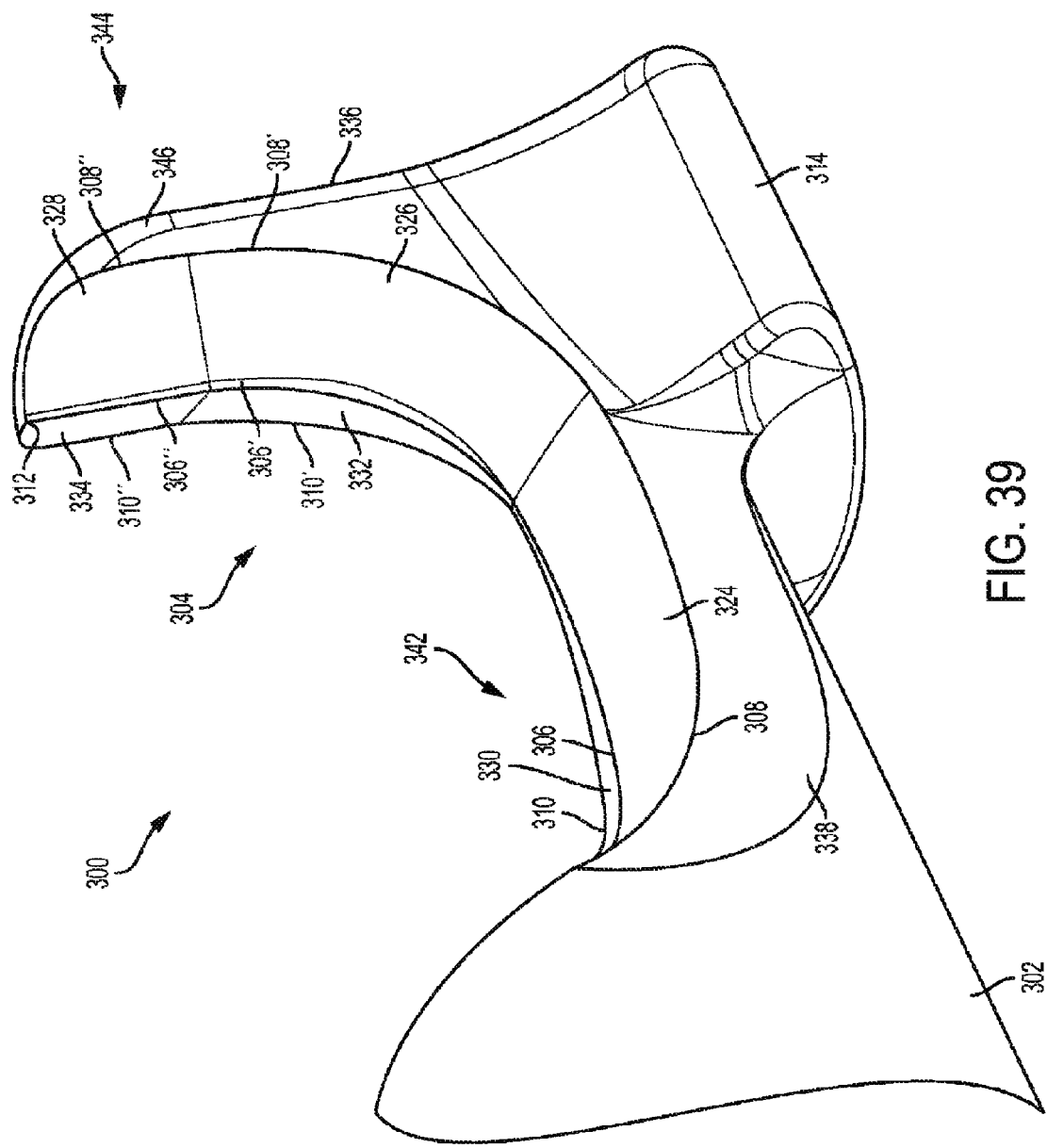
FIG. 39 is a perspective view of the ultrasonic surgical blade shown in FIG. 39, according to one embodiment.
Figure 40:
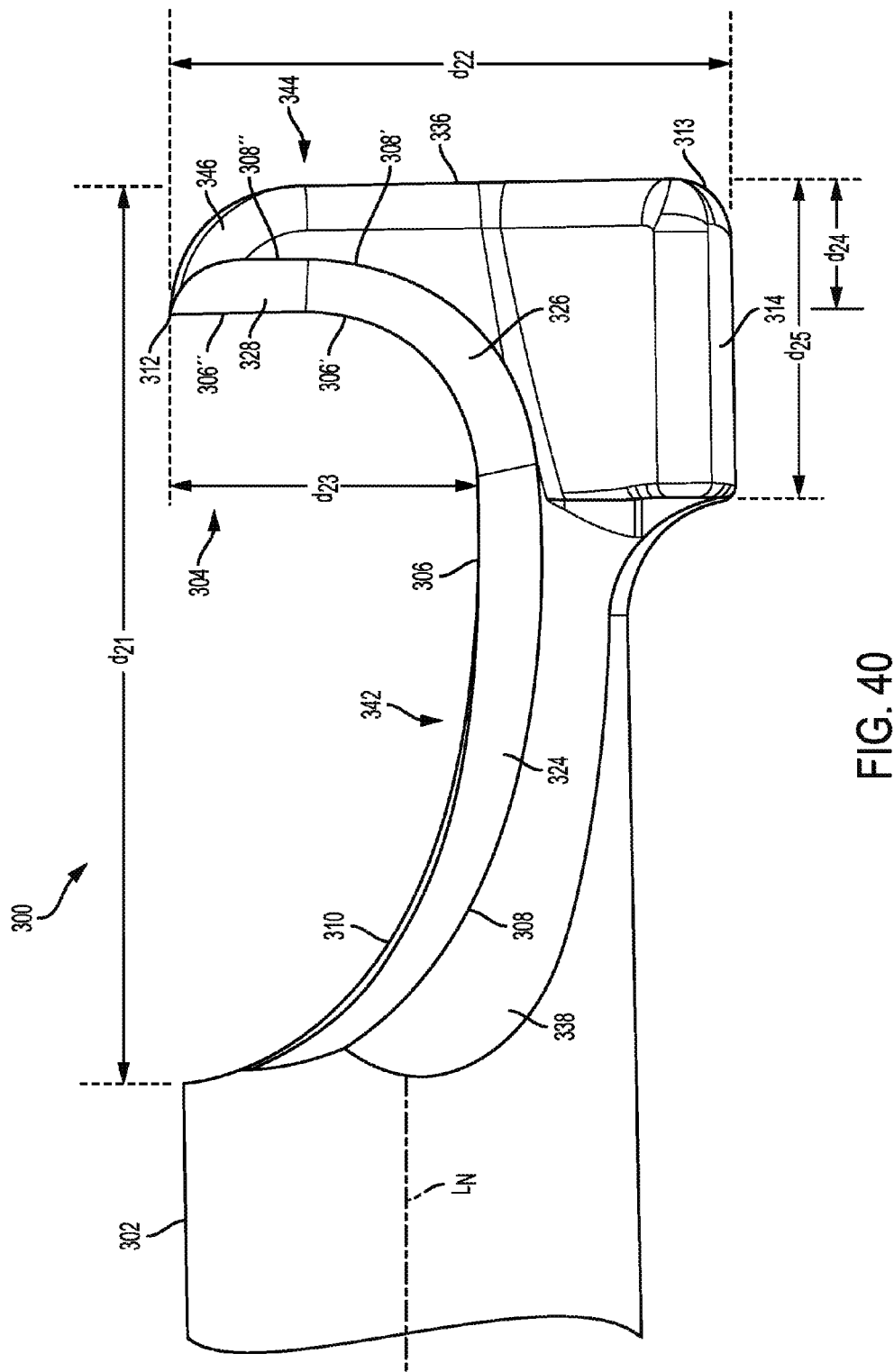
FIG. 40 is a side view of the ultrasonic surgical blade shown in FIG. 39, according to one embodiment.
Figure 41:
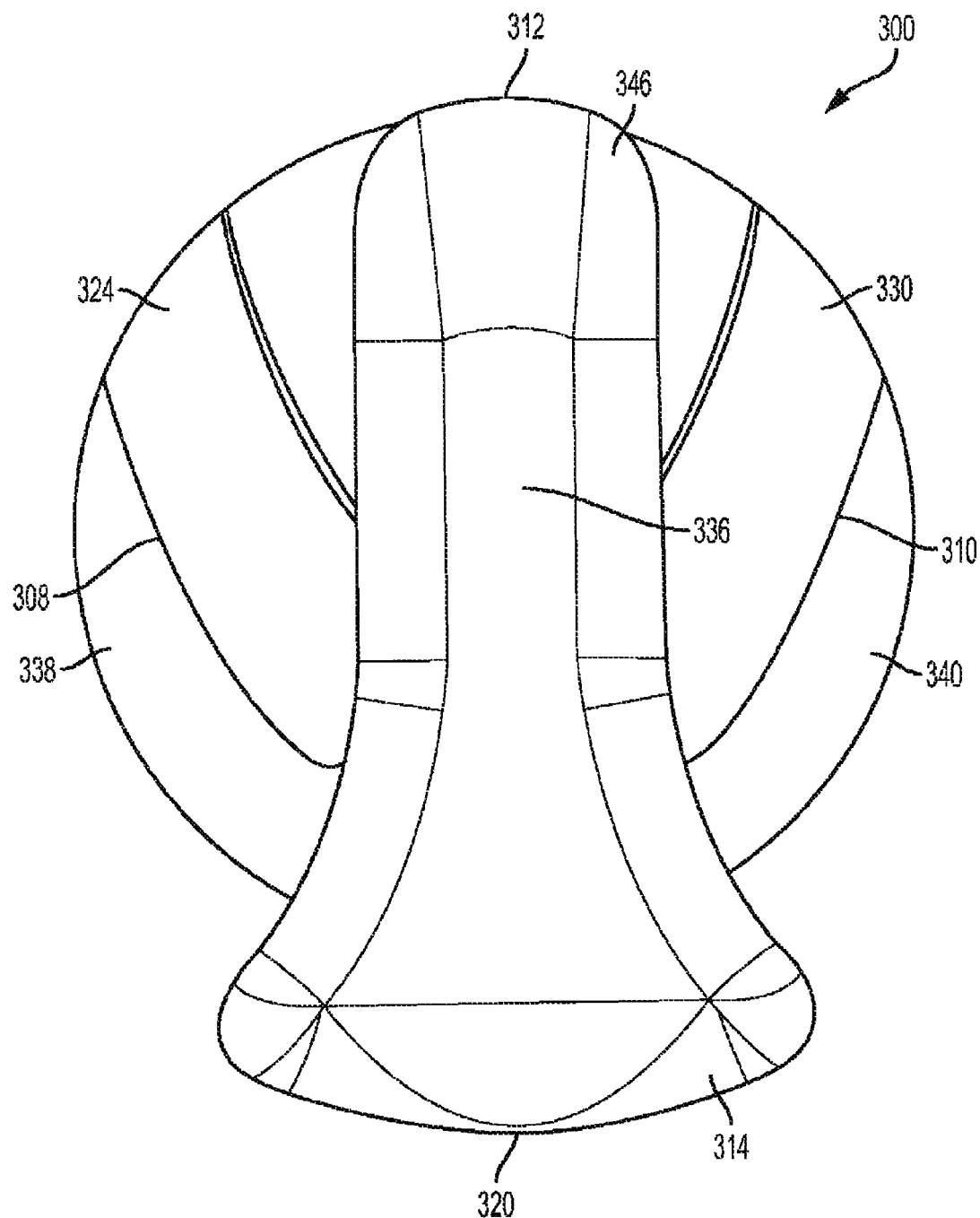
FIG. 41 is an end view of the ultrasonic surgical blade shown in FIG. 39, according to one embodiment.

FIG. 39 is a perspective view of the ultrasonic surgical blade 300 shown in FIG. 39, according to one embodiment. FIG. 40 is a side view of the ultrasonic surgical blade 300 shown in FIG. 39, according to one embodiment. FIG. 41 is an end view of the ultrasonic surgical blade 300 shown in FIG. 39, according to one embodiment.

With reference now to FIGS. 39-41, in one embodiment the ultrasonic surgical blade 300 comprises a neck 302 configured to acoustically couple to an ultrasonic transmission waveguide which is configured and adapted to acoustically couple to a piezoelectric ultrasonic transducer. From the neck 302, the ultrasonic surgical blade 300 extends distally as a substantially longitudinal section 342, defined by dimension $d_{21}$, and transitions to a substantially transverse section 344 to define a blade hook 304. A sharp central ridge comprised of three distinct segments 306, 306', 306" extends from the neck 320 to a tip 312 of the hook 304 of the transverse section 344 defined by dimension $d_{22}$. As best seen in FIG. 40, a proximal segment 306 extends substantially longitudinally but has an arcuate component such that it extends downwardly from the neck 320 to an inflection point with an arcuate intermediate segment 306', which extends to a substantially linear distal segment 306". The substantially linear distal segment 306" extends from the junction of the arcuate intermediate section 306' to the tip 312 of the blade hook 304.

The proximal segment 306 of the sharp central ridge is defined by the junction of two proximal oblique surfaces 324, 330 that extend downwardly and outwardly from the proximal sharp central ridge 306. A first lateral sharp cutting edge 308 is defined by the junction of the proximal oblique surface 324 and the lateral surface 338. On the other side of the blade 300, a second lateral sharp cutting edge 310 is defined by the junction of the proximal oblique surface 330 and the other lateral surface 340 (FIG. 41).

The intermediate arcuate segment 306' of the sharp central ridge is defined by junction of intermediate arcuate oblique surfaces 326, 332 that extend downwardly and outwardly from the intermediate arcuate segment 306' of the sharp central ridge. A sharp cutting edge 308' is defined by the junction of the intermediate arcuate oblique arcuate surface 326 and an end mass 314 that is located below the transverse section 344 of the blade hook 304 and partially below the longitudinal section 342. An arcuate section of a sharp cutting edge 310' is defined by the junction of the intermediate arcuate oblique surface 332 and the end mass 314. The end mass 314 is used to acoustically balanced the ultrasonic surgical blade 300.

The distal linear segment 306" of the sharp central ridge is defined by junction of distal oblique surfaces 328, 334 that extend distally and outwardly from the distal linear segment 306" of the sharp central ridge. A sharp cutting edge 308" is defined by the junction of the distal oblique arcuate surface 328 and a body portion of the blade hook 304. A sharp cutting edge 310" is defined by the junction of the distal oblique surface 334 and a body portion of the blade hook 304.

As shown in FIG. 40, the depth or height of the blade hook 304 of the transverse section 344 defined by dimension $d_{23}$ should be maximized so the surgeon can hook and drag tissue to dissect the tissue along a plane. The dimension $d_{23}$ can be optimized to enable the surgeon to hook and drag to dissect the gall bladder from the liver bad, for example. The dimension $d_{23}$ of the hook 304 is approximately 2.794 mm and may vary between 1.016 mm to 4.572 mm (0.040 in to 0.180 in), without departing from the scope of the disclosure. The dimension $d_{21}$ of the longitudinal section 342 of the blade 300 is approximately 10.414 mm and may vary between 1.778 mm to 19.050 mm (0.070 in to 0.750 in), without departing from the scope of the disclosure. The end mass 314 extends proximally from the distal surface 336 of the hook 304 and has a dimension $d_{25}$. The dimension $d_{25}$ of the end mass 314 is approximately 5.207 mm and may vary between 0.889 mm to 9.525 mm (0.035 in to 0.375 in), without departing from the scope of the disclosure. The dimension $d_{22}$ of the transverse portion 344 of the blade hook 304 is approximately 4.2545 mm (0.1675 in) and may vary from 3.4036 mm to 5.1054 mm (0.1340 in to 0.2010 in). The dimension $d_{24}$ is approximately 0.9525 mm (0.0375 in) and can vary from 0.762 mm to 1.143 mm (0.0300 in to 0.0450 in). A straight line segment extending from the tip 312 of the blade hook 304 to a point 313 toward the distal end of the end mass 314 has a dimension of approximately 4.3510 mm (0.1713 in) and can vary from 3.4808 mm to 5.2200 mm (0.1370 in to 0.2055 in).

Figure 42:
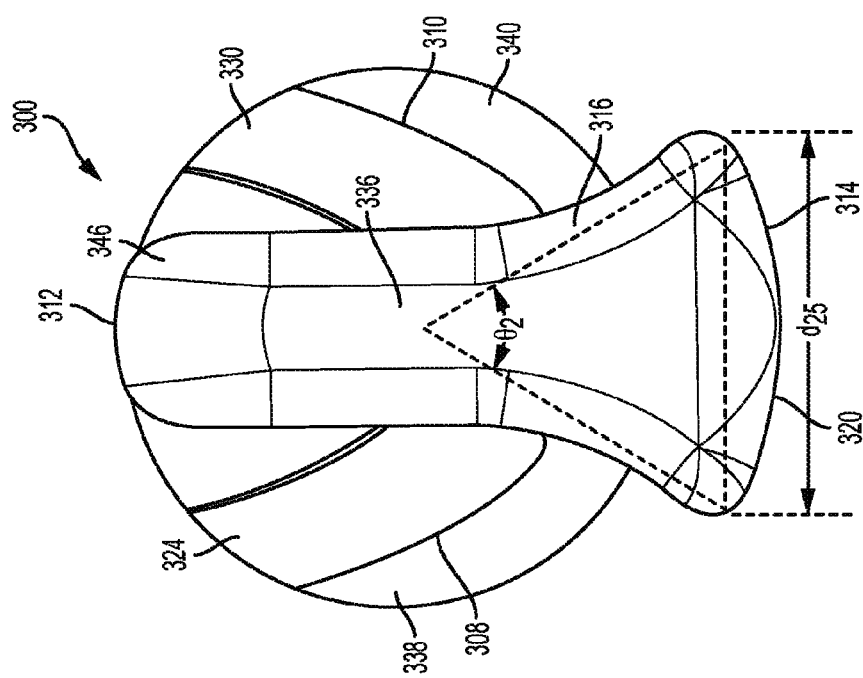
FIG. 42 is an end view of the ultrasonic surgical blade shown in FIGS. 39-41 illustrating a triangle shaped end mass, according to one embodiment.

FIG. 42 is an end view of the ultrasonic surgical blade 300 shown in FIGS. 39-41 illustrating a triangle shaped end mass 314, according to one embodiment. With reference now to FIGS. 40 and 42, the depth of the blade hook 304 of the transverse section 344 defined by transverse dimension $d_{23}$ and longitudinal dimension $d_{21}$ of the longitudinal section 342 creates a large overhung mass relative to the neutral axis $L_N$ of the ultrasonic transmission waveguide that extends proximally from the neck section 302 of the ultrasonic surgical blade 300. To counteract the unbalancing effects of the large overhung mass, a local balance element is provided. In the illustrated embodiments, the local balance element is provided by the end mass 314. In one embodiment, balance is achieved locally via a triangle 316 shaped end mass 314 that extends proximally by a dimension of $d_{25}$. In one embodiment, the triangle 316 shaped end mass 314 is define by an angle $\theta_2$. Increasing or decreasing the angle $\theta$ changes the local mass and thus alters the balance of the blade 300. Accordingly, the balance of the blade 300 can be adjusted by changing the angle $\theta_2$. It will be appreciated that the balance end mass 314 element adjusts the acoustic balance of the ultrasonic surgical blade 300.

Figure 43:
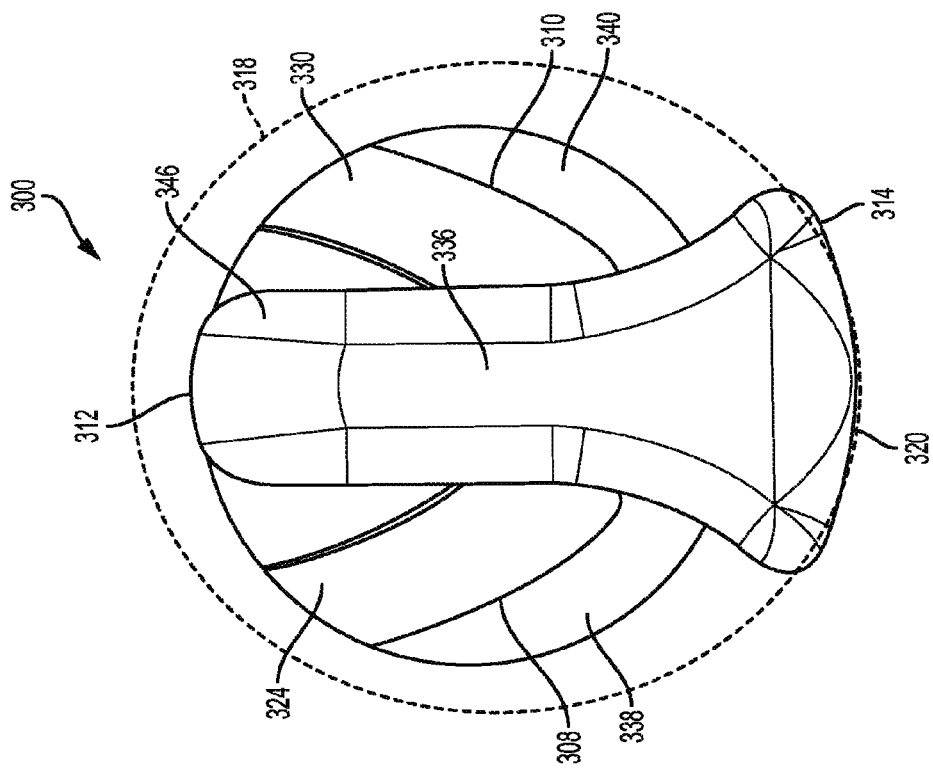
FIG. 43 is an end view of the ultrasonic surgical blade shown in FIGS. 39-41 illustrating a suitable diameter for trocar entry, according to one embodiment.

FIG. 43 is an end view of the ultrasonic surgical blade 300 shown in FIGS. 39-41 illustrating a suitable diameter 318 for trocar entry, according to one embodiment. As shown in FIG. 43, the total outer diameter 318 of the ultrasonic blade 300 is sized and configured to be slidably received in a trocar. In one embodiment, the maximum diameter 318 is about 5 mm fro trocar entry.

Figure 44:
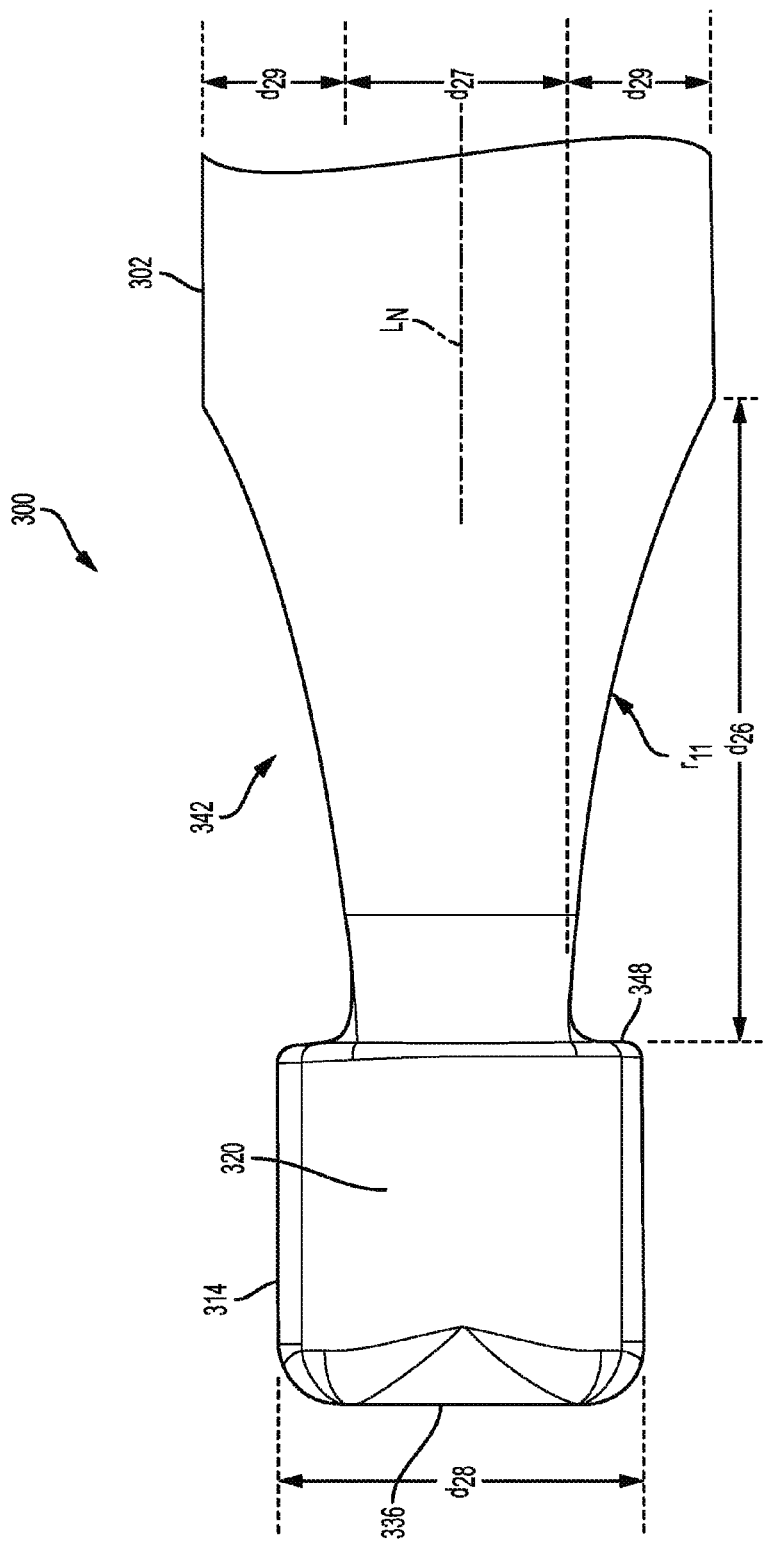
FIG. 44 is a bottom view of the ultrasonic surgical blade shown in FIG. 39 in compression mode, according to one embodiment.

FIG. 44 is a bottom view of the ultrasonic surgical blade 300 shown in FIG. 39 in compression mode, according to one embodiment. The bottom surface 320 of the end mass 314 can be employed as a spot coagulation surface, otherwise referred to as a hemostasis surface. Only about a 3% amplitude drop in ultrasonic vibration amplitude has been observer across the face of the coagulation surface 320. The illustrated geometry of the end mass 314 and the coagulation surface 320 provides positive tissue effects. When the blade 300 is excited by ultrasonic energy, it oscillates between a compression mode and an tension mode repeatedly. Such oscillation between compression and tension modes creates the displacement necessary to provide the desired tissue effects such as cutting and coagulating tissue. In compression mode, the blade 300 defines its most compact form along the longitudinal axis $L_N$. As shown in FIG. 44, in the compression mode, the blade 300 illustrated in FIG. 44 can be characterized by several dimensions. For example, in compression mode, the blade 300 defines length $d_{26}$ between the neck section 302 and a proximal wall 348 of the end mass 314. The longitudinal section 342 of the blade 300 over the dimension $d_{26}$ defines a radius of curvature $r_{11}$. The width of the longitudinal section 342 where it meets the proximal wall 348 of the end mass 314 is defined by dimension $d_{27}$ and the width of the end mass 314 is defined by dimension $d_{28}$. The dimension $d_{29}$ is the distance between the narrowest portion of the longitudinal section 342 to the outer diameter of the longitudinal section 342.

Figure 45:
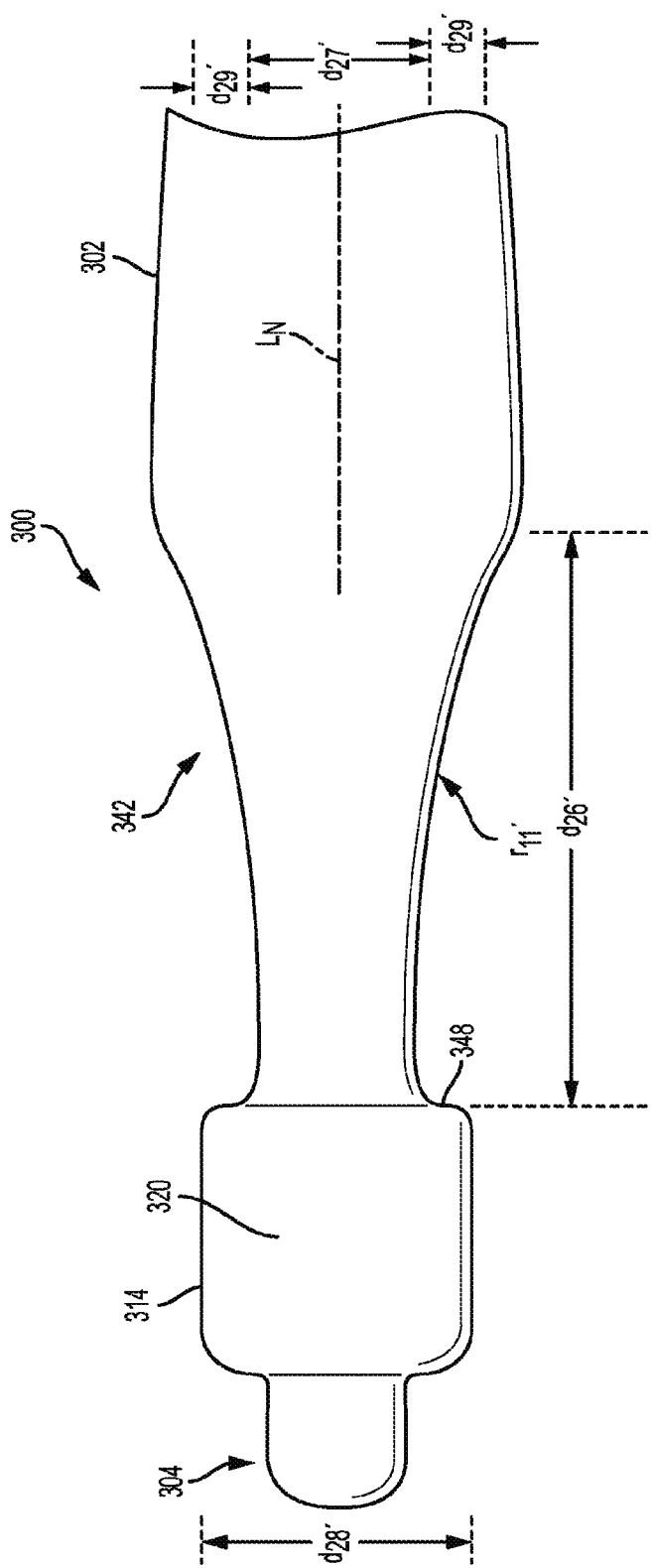
FIG. 45 is a bottom view of the ultrasonic surgical blade shown in FIG. 39 in tension mode, according to one embodiment.

FIG. 45 is a bottom view of the ultrasonic surgical blade 300 shown in FIG. 39 in tension mode, according to one embodiment. The dimensions of the surgical blade 300 in tension mode are labeled by a prime (') as compared to the dimensions of the blade 300 in compression mode as shown in FIG. 44. As will be appreciated, when the blade 300 is in tension mode it defines its most elongated form along the longitudinal axis $L_N$. As shown in FIG. 45, in the tension mode, the blade 300 illustrated in FIG. 45 can be characterized by several dimensions. For example, in tension mode, the blade 300 defines length $d_{26}'$ between the neck section 302 and the proximal wall 348 of the end mass 314. The longitudinal section 342 of the blade 300 over the distance defined by $d_{26}'$ defines a radius of curvature $r_{11}'$. The width of the longitudinal section 342 where it meets the proximal wall 348 of the end mass 314 is defined by dimension $d_{27}'$ and the width of the end mass 314 is defined by dimension $d_{28}'$. As the blade 300 transitions for the compression mode to the tension mode the dimensions of the blade 300 decrease in width and increase in length. Accordingly, with reference to FIGS. 44 and 45, the length $d_{26} < d_{26}'$ and $r_{11} < r_{11}'$. However, dimensions $d_{29} > d_{29}'$, $d_{27} > d_{27}'$, and $d_{28} > d_{28}'$.

Figure 46:
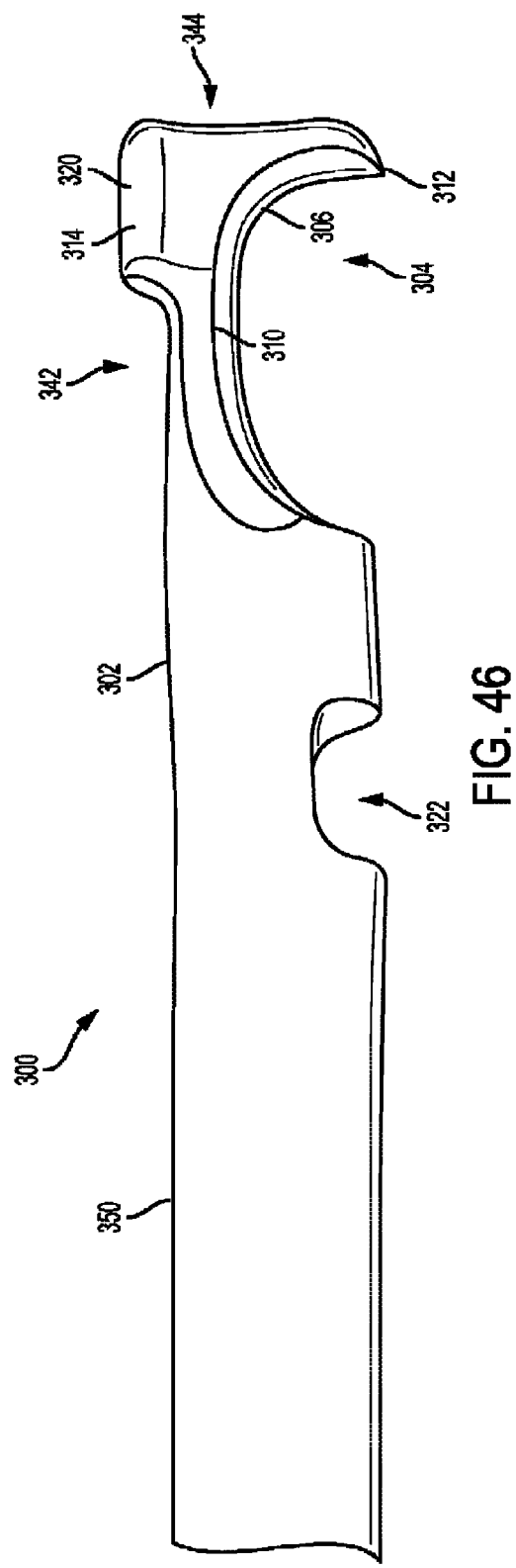
FIG. 46 illustrates the ultrasonic surgical blade shown in FIG. 39 in a neutral unexcited state.
Figure 47:
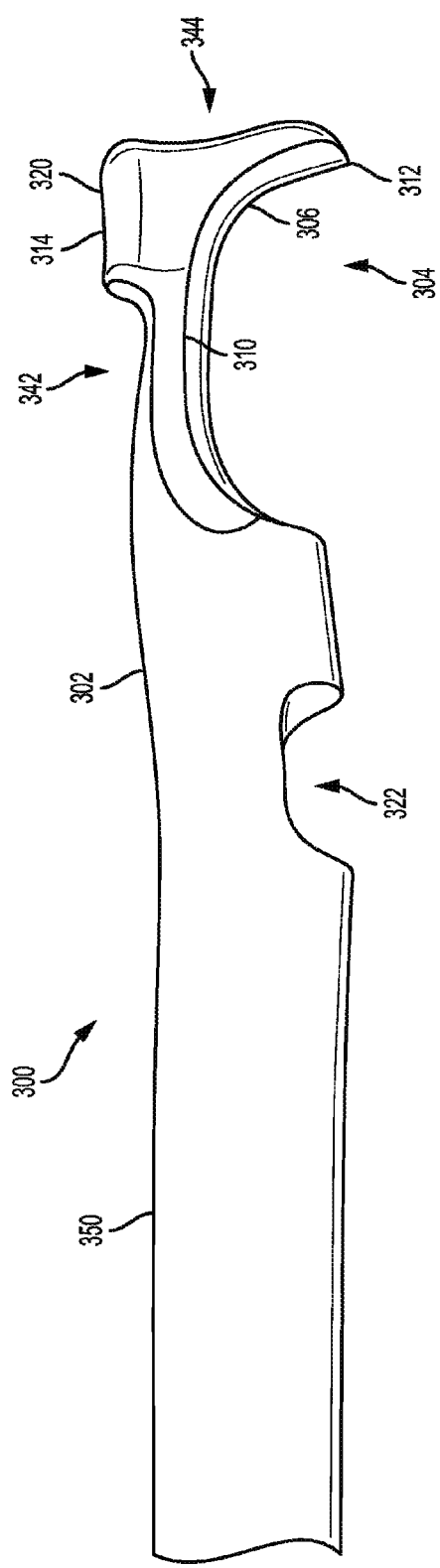
FIG. 47 illustrates the ultrasonic surgical blade shown in FIG. 46, as the vibration process initiates, where the blade hook is displaced distally under tension mode and the gap defined by the balance feature expands.
Figure 48:
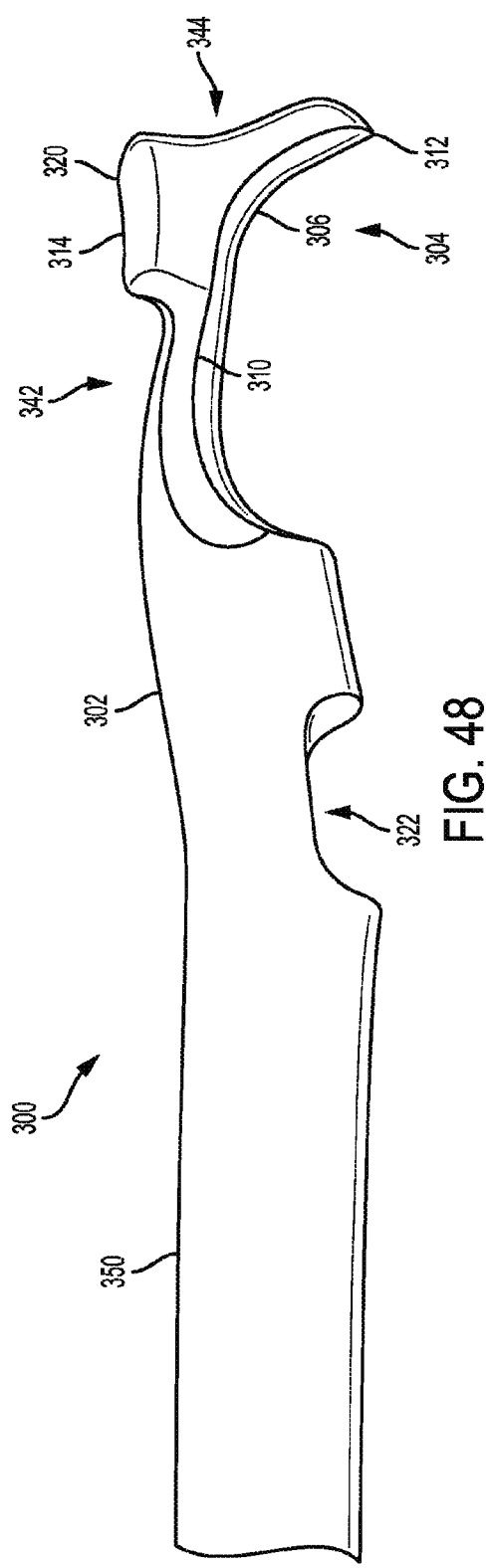
FIG. 48 illustrates the ultrasonic surgical blade shown in FIG. 47 as the blade continues to be displaced distally under tension until it reaches a point of maximum displacement under tension.
Figure 49:
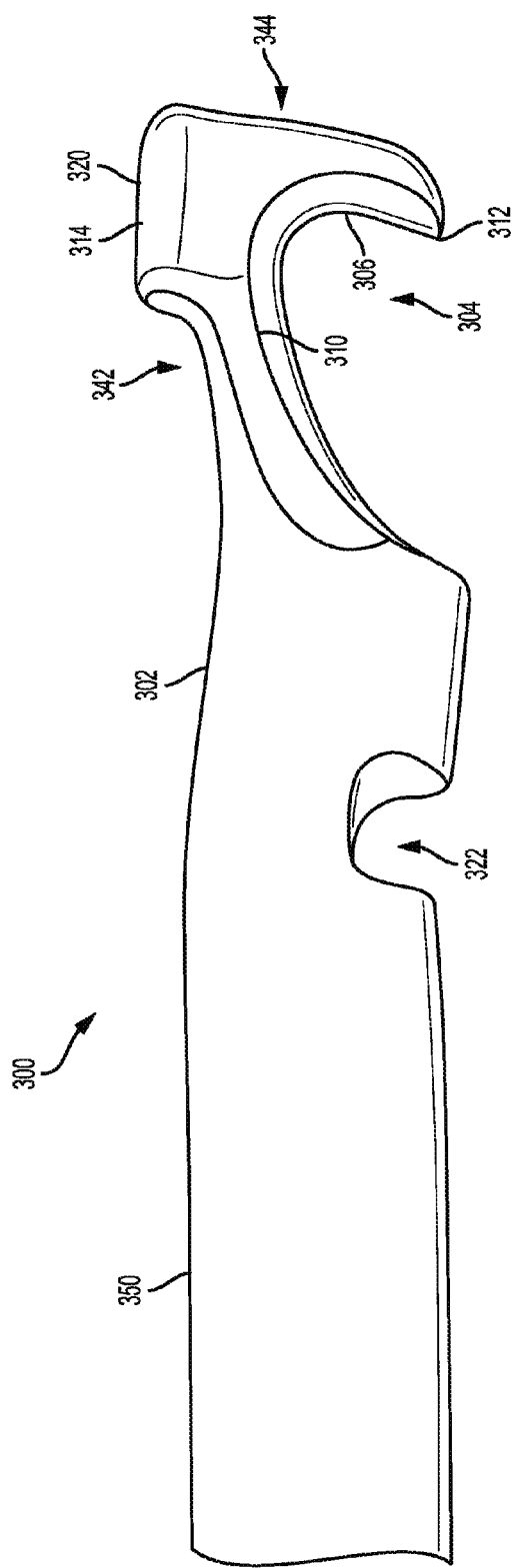
FIG. 49 illustrates the ultrasonic surgical blade shown in FIG. 48 as the blade is now in compression mode and has begun to contract.
Figure 50:
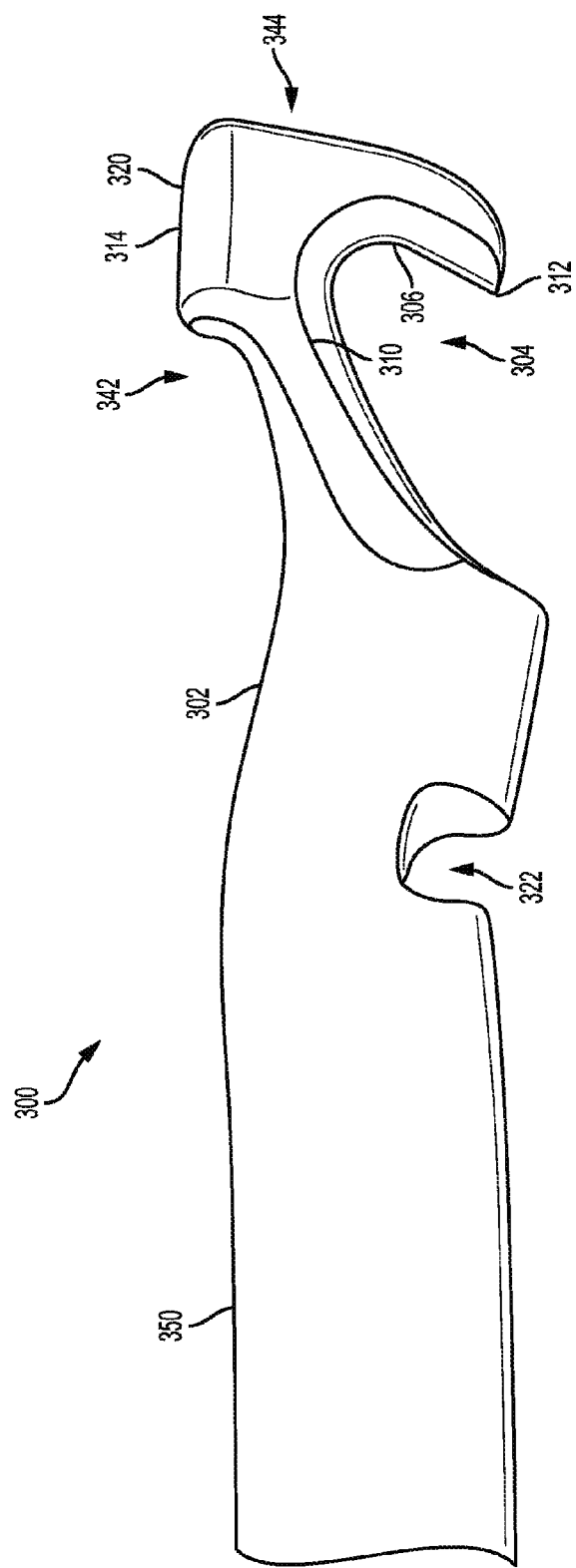
FIG. 50 illustrates the ultrasonic surgical blade shown in FIG. 49 as the blade has reached a point of maximum compression where its overall displacement is at a minimum and the gap defined by the balance feature is at a minimum.

FIGS. 46-50 illustrate a displacement cycle of the ultrasonic surgical blade 300, according to one embodiment. FIG. 46 illustrates the ultrasonic surgical blade shown in FIG. 39 in a neutral unexcited state. The longitudinal section 342 and the transverse section 344 are in a neutral state. A balance feature 322 is defined as a cutout portion in the ultrasonic transmission waveguide 350 to facilitate the expansion and contraction of the ultrasonic transmission waveguide 350 and the blade 300 during the vibratory process. As shown in FIG. 47, as the vibration process initiates, the blade 300 hook 304 is displaced distally under tension mode and the gap defined by the balance feature 322 expands. The blade 300 continues to be displaced distally under tension until it reaches a point of maximum displacement under tension as shown in FIG. 48. The diameter dimensions are at their minimum dimension, the length of the blade 300 is at a maximum or highest displacement, and the gap defined by the balance feature 322 is at a maximum. Once the blade 300 reaches the point of maximum displacement in tension mode as shown in FIG. 48, the blade 300 transitions to compression mode and begins to contract. As shown in FIG. 49, the blade 300 is now in compression mode and has begun to contract. The gap defined by the balance feature 322 has decreased in size to facilitate the compression process. As shown in FIG. 50, the blade 300 has reached a point of maximum compression where its overall displacement is at a minimum and the gap defined by the balance feature 322 is at a minimum. FIGS. 48 and 50 provide a good visual representation of the maximum and minimum longitudinal displacement of the blade hook 304 and how the blade hook 304 can be effectively used for dissecting tissue. Also, the longitudinal displacement of the blade 300 also displaces the end mass 314 to enable the coagulation surface 320 of the end mass 314 to be used to effectively coagulate tissue.

Figure 51:
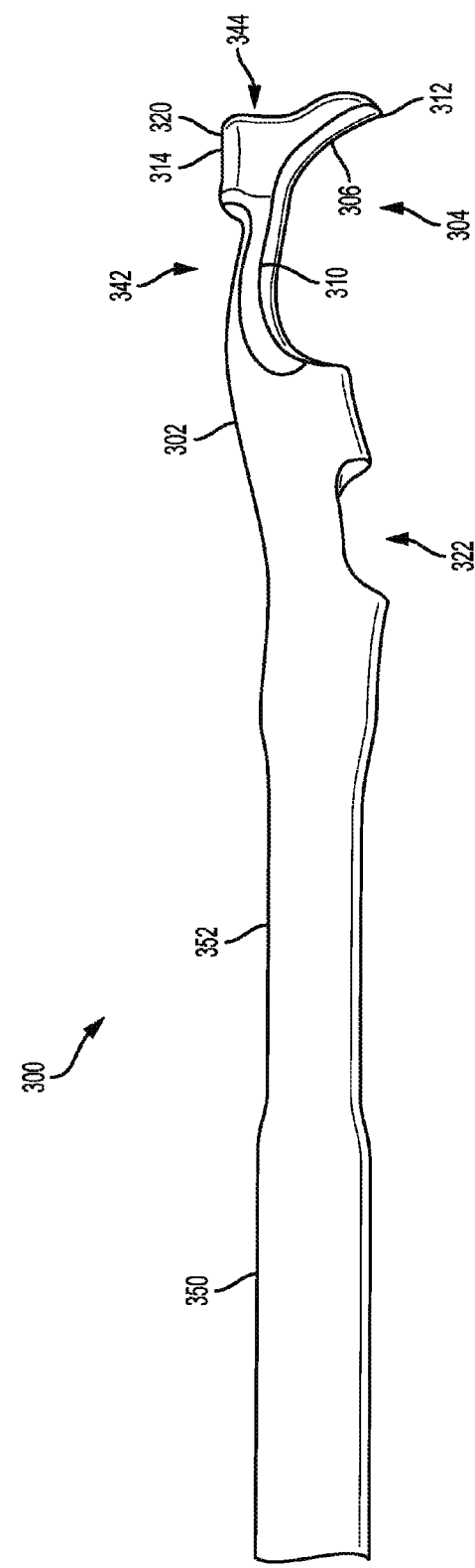
FIG. 51 illustrates a point of maximum displacement of the ultrasonic surgical blade shown in FIG. 39, according to one embodiment.

FIG. 51 illustrates a point of maximum displacement of the ultrasonic surgical blade 300, according to one embodiment. As shown in FIG. 51, the tip 312 of the blade hook 304 is at its point of maximum longitudinal displacement and the gap defined by the balance feature 322 is maximally expanded. A distal section 352 of the ultrasonic waveguide 350 has a reduced diameter.

Figure 52:
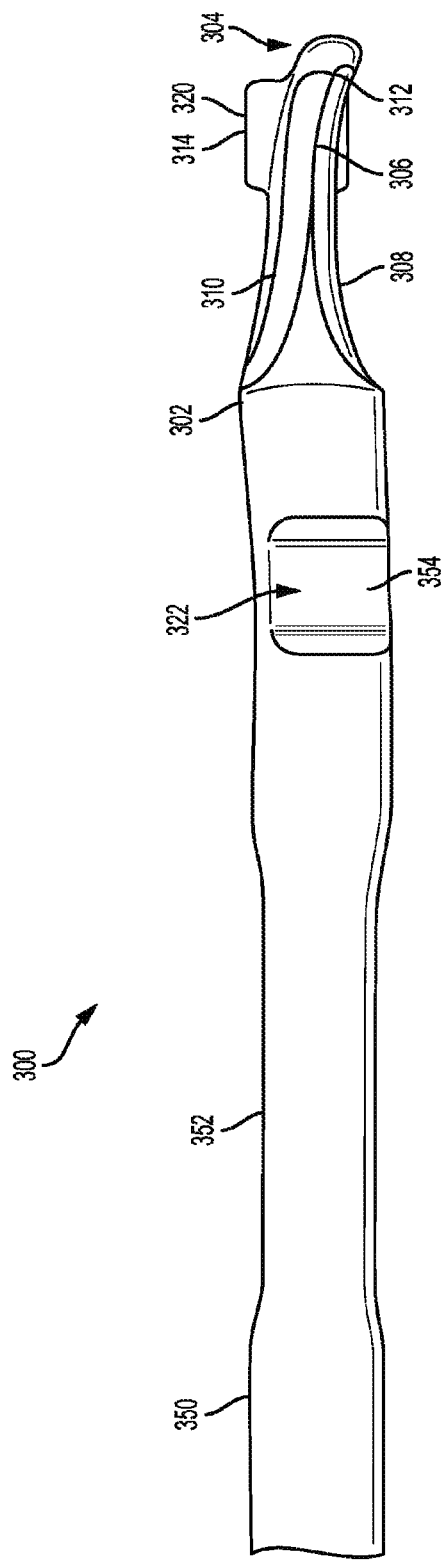
FIG. 52 illustrates a bottom view of the ultrasonic surgical blade shown in FIG. 51 under maximum displacement, according to one embodiment.

FIG. 52 illustrates a bottom view of the ultrasonic surgical blade 300 shown in FIG. 51 under maximum displacement, according to one embodiment. As shown in FIG. 52, the maximum stress area 354 is located in the balance feature 322 of the ultrasonic transmission waveguide 350. In use, the balance feature 322 should be protected by the outer sheath of the instrument.

Right Angle Ultrasonic Surgical Blades
(Embodiment 4)

The present disclosure now turns to various embodiments of an ultrasonic surgical blade comprising a right angle or near right angle bend near the distal end to provide advantages in tissue access and visibility. As previously discussed in connection with the foregoing embodiments, the challenges with a right angle ultrasonic blade or a hook-type ultrasonic blade include stress and balance. The embodiments disclosed in FIGS. 53-60 provide an ultrasonic blade with a mass distributed in such a manner that the blade behaves in a balanced fashion and is sufficiently strong to withstand the stresses.

FIG. 53. Illustrates one embodiment of a right angle balance blade 400. The right angle balance blade 400 comprises a longitudinal section 418 and a transverse section 412. The transverse section 412 of the blade 400 may be at or close to 90° relative to the longitudinal section 418. The longitudinal section 418 extends longitudinally along an ultrasonic waveguide section 402 of the blade 400. A centerline is defined along the longitudinal axis $L_N$ of the blade 400. The distal end of the blade 400 defines a transverse section 412 relative to the longitudinal section 418. The distal end includes a working side defining a thin elongated right angle member 404 section and back side 414 defining a mass 406. A tip 408 having a relatively small surface area is employed for tissue dissection and a rounded end 410 having a larger surface area is employed for coagulation.

In the illustrated embodiment, the right angle balanced blade 400 comprises a mass distributed such that, at the distal end 412, the back side 414 of the blade 400 has a large mass 406 distributed relatively close to a centerline $L_4$ of the blade 400. The working side 416 of the blade 400 has a mass distributed in a relatively long, thin section right angle member 404 section when compared to the back side 414 mass 406. This may resemble some designs of golf putters, for example. Additionally, if necessary, balance features may be added, such as notches, to reduce the transverse motion accompanying the desired longitudinal mode.

FIG. 54 is an illustration of a balanced displacement plot 420 of a right angle balanced blade, similar to the blade 400 shown FIG. 53, in a maximum displacement state, according to one embodiment. As shown, the area of maximum stress 422 occurs at the tip of the blade 400 whereas the areas of minimum stress occur at the blade neck section 424 and the transition section 426 from the blade 400 to the ultrasonic transmission waveguide 402.

With reference to FIGS. 53 and 54, the right angle balanced blade 400 provides a waveguide 402 with the blade tip 408 extending at a right angle or near right angle relative to the longitudinal section 418. The blade 400 provides the same utility as derived from a simple monopolar RF hook. The technical challenges with the right angle balanced blade 400 includes transmitting longitudinal motion around the corner 428, defined as the point where the transverse section 412 extends from the longitudinal section 418, without creating transverse motion. The transverse motion in the distal right-angle end effector can be used to create hemostasis using the surface area 410 of the back end 414 of the blade 400.

In one embodiment, rather than driving the waveguide 402 in longitudinal motion and compensating for the ensuing transverse motion, the waveguide 402 is driven in transverse motion, and the whipping motion of the end drive the right angle member 404 section in longitudinal motion as shown in FIG. 54. One way to illustrate this concept is by analogy to a transversely vibrating rod with a free end such as end 408. In a transversely vibrating rod with a freed end, the end "whips" up and down and the slope of the end is relatively high. If a concentrated mass, such as mass 406, is added to the tip 408, it weighs down the free-end. If the mass is zero, the end acts as a free end, and for example has a positive slope. If the mass 406 is infinite, it acts as a pinned condition and the corresponding slope would be negative. A mass 406 can be selected such that the slope is zero, and then the end 408 moves up and down with near zero slope. If the right angle member 404 works as that mass, where the waveguide 402 and the right angle member 404 join at the corner 428, the loaded end 408 just pushes the right angle member 404 up and down in a longitudinal motion. In another aspect, when the right angle member 404 is a half wave resonator, it presents zero dynamic load (i.e., zero driving point impedance), so the end of the waveguide 403 just pulls the right angle member 404 up and down with it, because it experiences no load.

FIG. 55 illustrates a right angle balanced ultrasonic blade 430 driven in transverse mode to produce longitudinal motion at an end effector 434 section, according to one embodiment. The right angle balanced ultrasonic blade 430 comprises a longitudinal waveguide section 432 and a right angle end effector member 434 positioned transverse to the longitudinal waveguide section 432. As described above, driving the waveguide section 432 in transverse mode causes the transverse right angle end effector member 434 to be displaced from a proximal end to a distal end to effectively create longitudinal motion suitable for dissecting tissue with the tip 436 of the transverse right angle end effector member 434.

FIGS. 56-60 illustrate several embodiments of right angle balanced ultrasonic surgical blades. FIG. 56 illustrates one configuration of a right angle balanced ultrasonic surgical blade 440. The right angle balanced ultrasonic surgical blade 440 comprises a longitudinal waveguide section 442, a corner section 446, and an end effector section 444 positioned transverse to the longitudinal waveguide section 442 extending from the corner section 446. A tip section 448 is used to dissect tissue. The tip section 448 moves longitudinally as the waveguide section 442 is excited transversely.

FIG. 57 illustrates one configuration of a right angle balanced ultrasonic surgical blade 450. The right angle balanced ultrasonic surgical blade 450 comprises a longitudinal waveguide section 452, a corner section 456, and an end effector section 454 positioned transverse to the longitudinal waveguide section 452 extending from the corner section 456. A balance feature 453 is positioned along the waveguide section 452 between the waveguide section 452 and the corner section 456. In the right angle balanced ultrasonic surgical blade 450, the balance feature 453 is a reduced mass portion of the longitudinal waveguide section 452. A tip section 458 is used to dissect tissue. The tip section 458 moves longitudinally as the waveguide section 452 is excited transversely.

FIG. 58 illustrates one configuration of a right angle balanced ultrasonic surgical blade 460. The right angle balanced ultrasonic surgical blade 460 comprises a longitudinal waveguide section 462, a corner section 466, and an end effector section 464 positioned transverse to the longitudinal waveguide section 462 extending from the corner section 466. A balance feature 463 is positioned along the waveguide section 462 between the waveguide section 462 and the corner section 466. In the right angle balanced ultrasonic surgical blade 460, the balance feature 463 is an increased mass portion of the longitudinal waveguide section 462. The tip section 468 is used to dissect tissue. The tip section 468 moves longitudinally as the waveguide section 462 is excited transversely.

FIG. 59 illustrates one configuration of a right angle balanced ultrasonic surgical blade 470. The right angle balanced ultrasonic surgical blade 470 comprises a longitudinal waveguide section 472, a corner section 476, and an end effector section 474 positioned transverse to the longitudinal waveguide section 472 extending from the corner section 476. A balance feature 473 is positioned on the end effector section 474 between the corner section 476 and the tip section 478. In the right angle balanced ultrasonic surgical blade 470, the balance feature 473 is a reduced mass portion of the end effector section 474. The tip section 478 is used to dissect tissue. The tip section 478 moves longitudinally as the waveguide section 472 is excited transversely.

FIG. 60 illustrates one configuration of a right angle balanced ultrasonic surgical blade 480. The right angle balanced ultrasonic surgical blade 480 comprises a longitudinal waveguide section 482, a corner section 486, and an end effector section 484 positioned transverse to the longitudinal waveguide section 482 extending from the corner section 486. A balance feature 483 is positioned on the end effector section 484 between the corner section 486 and the tip section 488. In the right angle balanced ultrasonic surgical blade 480, the balance feature 483 is an increased mass portion of the end effector section 484. The tip section 488 is used to dissect tissue. The tip section 488 moves longitudinally as the waveguide section 482 is excited transversely.

As discussed herein, any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The invention claimed is:

1. An ultrasonic surgical blade, comprising:
   a solid body;
   a longitudinal portion having a proximal end configured to couple to an ultrasonic transmission waveguide and a distal end configured to dissect and coagulate tissue, the longitudinal portion comprising:
   a substantially planar longitudinal surface; and
   a distal hemostasis surface located opposite of the substantially planar longitudinal surface, the distal hemostasis surface having a surface area S1 defined by a distal surface inflection, a first proximal surface inflection, and first and second lateral cutting edges extending from the distal surface inflection to the first proximal surface inflection, wherein the distal surface inflection defines a minimum width of the distal hemostasis surface and the first proximal surface inflection defines a maximum width of the distal hemostasis surface;
   a transverse portion extending crosswise from the distal end of the longitudinal portion, the transverse portion defining a hook extending above the ultrasonic transmission waveguide having a free end configured to pull and dissect tissue, the transverse portion comprising:
   a curved section extending from a distal end of the substantially planar longitudinal surface;
   a tip surface defined at the free end;
   a substantially planar proximal inner surface extending from the curved section to the tip surface; and
   an outer concave distal surface extending from the tip surface to the distal hemostasis surface; and
   a distal dissection edge defined at a surface inflection of the outer concave distal surface and the distal hemostasis surface.

2. The ultrasonic surgical blade of claim 1, wherein the longitudinal portion comprises a proximal hemostasis surface located opposite of the substantially planar longitudinal surface, the proximal hemostasis surface having a surface area S2 defined by the first proximal surface inflection defining a junction of the distal hemostasis surface and the proximal hemostasis surface, a second proximal surface inflection, and third and fourth lateral cutting edges extending from the first proximal surface inflection to the second proximal surface inflection.

3. The ultrasonic surgical blade of claim 2, wherein the depth of the transverse portion measured from the tip surface to the proximal hemostasis surface is selected from a range of 1.8 mm to 3.0 mm.

4. The ultrasonic surgical blade of claim 2, wherein the surface area S2 is selected from a range of 6.45 mm$^2$ to 12.90 mm$^2$.

5. The ultrasonic surgical blade of claim 2, wherein the third and fourth lateral cutting edges define a maximum width of the proximal hemostasis surface at a location between the first and second proximal surface inflections.

6. The ultrasonic surgical blade of claim 1, wherein the surface area S1 is selected from a range of 3.226 mm$^2$ to 6.45 mm$^2$.

7. The ultrasonic surgical blade of claim 1, further comprising a beveled edge defined between the tip surface and the substantially planar proximal inner surface.

8. The ultrasonic surgical blade of claim 1, further comprising an oblique tip surface extending from the tip surface to the outer concave distal surface.

9. An ultrasonic surgical blade, comprising:
a solid body;
a longitudinal portion having a proximal end and a distal end, the longitudinal portion comprising:
   a substantially planar longitudinal surface; and
   a distal hemostasis surface located opposite of the substantially planar longitudinal surface, the distal hemostasis surface having a surface area S1 defined by a distal surface inflection, a first proximal surface inflection, and first and second lateral cutting edges extending from the distal surface inflection to the first proximal surface inflection, wherein the distal surface inflection defines a minimum width of the distal hemostasis surface and the first proximal surface inflection defines a maximum width of the distal hemostasis surface;
a transverse portion extending crosswise from the distal end of the longitudinal portion, the transverse portion defining a hook having a free end, the transverse portion comprising:
   a curved section extending from a distal end of the substantially planar longitudinal surface;
   a tip surface defined at the free end;
   a proximal inner surface extending from the curved section to the tip surface; and
   an outer concave distal surface extending from the tip surface to the distal hemostasis surface.

10. The ultrasonic surgical blade of claim 9, wherein the longitudinal portion comprises a proximal hemostasis surface located opposite of the substantially planar longitudinal surface, the proximal hemostasis surface having a surface area S2 defined by the first proximal surface inflection defining a junction of the distal hemostasis surface and the proximal hemostasis surface, a second proximal surface inflection, and third and fourth lateral cutting edges extending from the first proximal surface inflection to the second proximal surface inflection.

11. The ultrasonic surgical blade of claim 10, wherein the depth of the transverse portion measured from the tip surface to the proximal hemostasis surface is selected from a range of 1.8 mm to 3.0 mm.

12. The ultrasonic surgical blade of claim 10, wherein the surface area S2 is selected from a range of 6.45 mm$^2$ to 12.90 mm$^2$.

13. The ultrasonic surgical blade of claim 10, wherein the third and fourth lateral cutting edges define a maximum width of the proximal hemostasis surface at a location between the first and second proximal surface inflections.

14. The ultrasonic surgical blade of claim 9, wherein the surface area S1 is selected from a range of 3.226 mm$^2$ to 6.45 mm$^2$.

* * * * *